(12) United States Patent
Kubanek

(10) Patent No.: US 12,329,566 B2
(45) Date of Patent: Jun. 17, 2025

(54) SYSTEMS AND METHODS FOR MODULATION OF DEEP BRAIN CIRCUITS

(71) Applicant: UNIVERSITY OF UTAH RESEARCH FOUNDATION, Salt Lake City, UT (US)

(72) Inventor: Jan Kubanek, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 224 days.

(21) Appl. No.: 18/093,220

(22) Filed: Jan. 4, 2023

(65) Prior Publication Data

US 2023/0210493 A1  Jul. 6, 2023

Related U.S. Application Data

(60) Provisional application No. 63/296,252, filed on Jan. 4, 2022.

(51) Int. Cl.
*A61B 8/08* (2006.01)
*A61N 7/00* (2006.01)
*A61N 7/02* (2006.01)

(52) U.S. Cl.
CPC .............. *A61B 8/0808* (2013.01); *A61N 7/00* (2013.01); *A61N 7/02* (2013.01);
(Continued)

(58) Field of Classification Search
CPC .......... A61B 8/0808; A61N 7/00; A61N 7/02; A61N 2007/0021; A61N 2007/0026; A61N 2007/0078; A61N 2007/0095
See application file for complete search history.

(56) References Cited

U.S. PATENT DOCUMENTS 5,142,649 A  8/1992  O'Donnell
6,612,988 B2  9/2003  Maor et al.
(Continued)

FOREIGN PATENT DOCUMENTS

CN  113260857 A   8/2021
EP   1381430 B1   5/2009
(Continued)

OTHER PUBLICATIONS

Airan, Raag D., et al. "Noninvasive targeted transcranial neuromodulation via focused ultrasound gated drug release from nanoemulsions." Nano letters 17.2 (2017): 652-659. (Year: 2017).*
(Continued)

*Primary Examiner* — Sean D Mattson
(74) *Attorney, Agent, or Firm* — Michael Best & Friedrich LLP

(57) ABSTRACT

Systems and methods for applying therapeutic ultrasound to the brain to compensate for attenuation and dephasing of ultrasound by each individual's head. The compensation is based on relative ultrasound through-transmit measurements, which are performed using a set of ultrasonic emitters over one side of the head and a set of receivers on the other side. The measurements are performed with the head absent and present. Based on the difference between these measurements, the set of ultrasound waves is adjusted to compensate for attenuations and dephasing caused by the ultrasound wave passing into the head through the scalp and skull. The adjusted set of ultrasound waves provides intended, deterministic ultrasound intensity at the target location. The deterministic delivery enables safe and effective ultrasonic neuromodulation, local drug release from nanoparticle carriers, and microbubble-based disruption of blood-brain barrier for the delivery of drugs, genes, and stem cells across the blood-brain barrier.

15 Claims, 29 Drawing Sheets

(29 of 29 Drawing Sheet(s) Filed in Color)

(52) U.S. Cl.
CPC ............... *A61N 2007/0021* (2013.01); *A61N 2007/0026* (2013.01); *A61N 2007/0078* (2013.01); *A61N 2007/0095* (2013.01)

(56) References Cited

U.S. PATENT DOCUMENTS

| | | | |
|---|---|---|---|
| 7,727,156 | B2 | 6/2010 | Angelsen et al. |
| 8,088,067 | B2 | 1/2012 | Vortman et al. |
| 8,613,714 | B2 | 12/2013 | Alleman et al. |
| 8,958,882 | B1 | 2/2015 | Hagedorn |
| 9,042,201 | B2 | 5/2015 | Tyler et al. |
| 9,061,133 | B2 | 6/2015 | Wurster et al. |
| 9,295,444 | B2 | 3/2016 | Schwartz et al. |
| 9,333,334 | B2 | 5/2016 | Jeffery et al. |
| 9,630,029 | B2 | 4/2017 | Wurster et al. |
| 9,636,133 | B2 | 5/2017 | Hall et al. |
| 9,729,252 | B2 | 8/2017 | Tyler et al. |
| 10,130,828 | B2 | 11/2018 | Vortman et al. |
| 10,285,593 | B2 | 5/2019 | O'reilly et al. |
| 10,349,917 | B2 | 7/2019 | Boctor et al. |
| 10,396,905 | B2 | 8/2019 | Tyler et al. |
| 10,413,757 | B2 | 9/2019 | Sato et al. |
| 10,512,794 | B2 | 12/2019 | Wurster |
| 10,575,816 | B2 | 3/2020 | Prus et al. |
| 11,199,625 | B2 | 12/2021 | Robert et al. |
| 11,400,306 | B2 | 8/2022 | Dolgoff |
| 11,458,337 | B2 | 10/2022 | Ebbini et al. |
| 2002/0111552 | A1* | 8/2002 | Maor ............... A61B 8/0816 600/443 |
| 2007/0083120 | A1 | 4/2007 | Cain et al. |
| 2008/0249419 | A1 | 10/2008 | Sekins et al. |
| 2012/0083717 | A1* | 4/2012 | Alleman ............ A61B 8/546 601/2 |
| 2012/0165670 | A1* | 6/2012 | Shi ............... A61B 5/6814 600/442 |
| 2013/0131495 | A1* | 5/2013 | Konofagou ........ A61B 5/0036 600/407 |
| 2013/0197401 | A1* | 8/2013 | Sato ............... A61N 7/00 601/2 |
| 2014/0058293 | A1 | 2/2014 | Hynynen et al. |
| 2015/0258352 | A1 | 9/2015 | Lin et al. |
| 2017/0232277 | A1 | 8/2017 | Hall et al. |
| 2018/0177491 | A1 | 6/2018 | Hynynen et al. |
| 2018/0206824 | A1 | 7/2018 | Taniguchi |
| 2019/0021666 | A1 | 1/2019 | Hynynen |
| 2020/0367862 | A1 | 11/2020 | Taniguchi |
| 2021/0146126 | A1 | 5/2021 | Waldstreicher et al. |
| 2021/0219952 | A1 | 7/2021 | Huang et al. |
| 2021/0393991 | A1* | 12/2021 | Miskovic ........... A61N 7/00 |
| 2022/0126120 | A1 | 4/2022 | Zachar |
| 2022/0233890 | A1 | 7/2022 | Hynynen et al. |
| 2023/0210493 | A1 | 7/2023 | Kubanek |

FOREIGN PATENT DOCUMENTS

| | | | |
|---|---|---|---|
| WO | 2020167992 | A1 | 8/2020 |
| WO | 2023211898 | A1 | 4/2023 |

OTHER PUBLICATIONS

Ahrnsbrak, R. et al. Key substance use and mental health indicators in the United States: Results from the 2016 National Survey on Drug Use and Health. Center for Behavioral Health Statistics and Quality, Substance Abuse and Mental Health Services Administration: Rockville, MD, USA, 2017 (86 pages).

Al, L., et al. "Effects of transcranial focused ultrasound on human primary motor cortex using 7T fMRI: a pilot study." BMC neuroscience 19.1 (2018): 1-10.

Al, L., et al. "Transcranial focused ultrasound for BOLD fMRI signal modulation in humans." 2016 38th Annual International Conference of the IEEE Engineering in Medicine and Biology Society (EMBC). IEEE, 2016.

Airan, R. D. et al. Noninvasive targeted transcranial neuromodulation via focused ultrasound gated drug release from nanoemulsions, Nano Letters 17 (2) (2017) 652-659.

Alexander, L. et al. "A focus on the functions of area 25." Brain sciences 9.6 (2019): 129.

Al-Harbi, K. S.. "Treatment-resistant depression: therapeutic trends, challenges, and future directions." Patient preference and adherence (2012): 369-388.

Almquist, S., et al. Rapid full-wave phase aberration correction method for transcranial high-intensity focused ultrasound therapies. J. Ther. Ultrasound 4, 1-11, (2016).

Anastasiadis, P., et al. Focused ultrasound-mediated blood-brain barrier disruption for enhanced drug delivery to brain tumors. In Nanotherapy for Brain Tumor Drug Delivery, 205-223 (Springer, 2021).

Aureva Transcranial Ultrasound Device With tPA in Patients With Acute Ischemic Stroke—Full Text View. (n.d.). Last update posted Nov. 30, 2018. Retrieved from https://clinicaltrials.gov/ct2/show/NCT03519737 (12 pages).

Badran, B.W., et al. "Sonication of the anterior thalamus with MRI-Guided transcranial focused ultrasound (tFUS) alters pain thresholds in healthy adults: A double-blind, sham-controlled study." Brain stimulation 13.6 (2020): 1805-1812.

Bailey, B., et al. Enhancement of axial resolution in fluorescence microscopy by standing-wave excitation. Nature 366, 44-48 (1993).

Bakker, R. et al. "The scalable brain atlas: instant web-based access to public brain atlases and related content." Neuroinformatics 13 (2015): 353-366.

Bergey, G. et al. Long-term treatment with responsive brain stimulation in adults with refractory partial seizures. Neurology, 84(8):810-817, 2015.

Bewersdorf, J., et al. Comparison of i5m and 4pi-microscopy. J. microscopy 222, 105-117 (2006).

Biase, L. D., et al. (2019). Transcranial Focused Ultrasound (tFUS) and Transcranial Unfocused Ultrasound (tUS) Neuromodulation: From Theoretical Principles to Stimulation Practices. Frontiers in Neurology, 10, 1-12.

Bishop, S. J. "Neurocognitive mechanisms of anxiety: an integrative account." Trends in cognitive sciences 11.7 (2007): 307-316.

Blackmore, J., et al. Ultrasound neuromodulation: A review of results, mechanisms and safety. Ultrasound medicine & biology 45, 1509-1536 (2019).

Bloom, De et al. The global economic burden of non-communicable diseases, Geneva: World Economic Forum, 2011, 1-48.

Braun, U., et al. "From maps to multi-dimensional network mechanisms of mental disorders." Neuron 97.1 (2018): 14-31.

Brinker, S. T. et al. Focused Ultrasound Platform for Investigating Therapeutic Neuromodulation Across the Human Hippocampus. Ultrasound Medicine Biol. 46, 1270-1274, (2020).

Bystritsky, A. "Treatment-resistant anxiety disorders." Molecular psychiatry 11.9 (2006): 805-814.

caregiver.org. Incidence and Prevalence of the Major Causes of Brain Impairment. Version dated Oct. 27, 2021. https://web.archive.org/web/20211027121715/https://www.caregiver.org/resource/incidence-and-prevalence-major-causes-brain-impairment/ (6 pages).

Carpentier, A. et al. Clinical trial of blood-brain barrier disruption by pulsed ultrasound. Science translational medicine, 8(343):343re2-343re2, 2016.

Casarotto, R. A., et al. Coupling Agents in Therapeutic Ultrasound: Acoustic and Thermal Behavior. Arch. Phys. Medicine Rehabil. 85, 162-165 (2004).

Cerevast. Stroke. Version dated Jul. 25, 2021. Retrieved from https://web.archive.org/web/20210725143548/https://cerevast.com/programs/stroke/ (3 pages).

Cerevast. Transcranial Ultrasound Neuromodulation. Version dated Jun. 15, 2021. Retrieved from https://web.archive.org/web/20210615120954/https://cerevast.com/science/neuromodulation/ (2 pages).

Chang, W. S. et al Factors associated with successful magnetic resonance-guided focused ultrasound treatment: efficiency of acoustic energy delivery through the skull. Journal of neurosurgery, 124(2):411-416, 2016.

(56) References Cited

OTHER PUBLICATIONS

Chen, G., et al. Superoscillation: from physics to optical applications. Light. Sci. & Appl. 8, 1-23 (2019).
Chen, K.-T. et al. "Theranostic strategy of focused ultrasound induced blood-brain barrier opening for CNS disease treatment." Frontiers in pharmacology 10 (2019): 86.
Chen, Y. et al. Engineering the phase front of light with phase-change material based planar lenses. Sci. Reports 5, 1-7, (2015).
Chim, S. S. et al. Three-dimensional image realization in interference microscopy. Appl. optics 31, 2550-2553 (1992).
Clement, G. T. et al. Micro-receiver guided transcranial beam steering. IEEE Transactions on Ultrason. Ferroelectr. Freq. Control. 49, 447-453, (2002).
Clennell, B., et al. "Transient ultrasound stimulation has lasting effects on neuronal excitability." Brain Stimulation 14.2 (2021): 217-225.
Dallapiazza, R. F. et al. Noninvasive neuromodulation and thalamic mapping with low-intensity focused ultrasound. J. Neurosurg. 1-10 (2017).
Dandekar, M. P., et al. "Deep brain stimulation for treatment-resistant depression: an integrative review of preclinical and clinical findings and translational implications." Molecular psychiatry 23.5 (2018): 1094-1112.
Davidson, R. J. "Anxiety and affective style: role of prefrontal cortex and amygdala." Biological psychiatry 51.1 (2002): 68-80.
Deffieux, T. et al. Low-intensity focused ultrasound modulates monkey visuomotor behavior. Curr. Biol. 23, 2430-2433 (2013).
Deng, L., et al. A multi-frequency sparse hemi-spherical ultrasound phased array for microbubble-mediated transcranial therapy and simultaneous cavitation mapping. Phys. Medicine & Biol. 61, 8476 (2016).
Deng, L., et al. A Noninvasive Ultrasound Resonance Method for Detecting Skull Induced Phase Shifts May Provide a Signal for Adaptive Focusing. IEEE transactions on bio-medical engineering 67, 2628-2637, (2020).
Dougherty, D. D., et al. "A randomized sham-controlled trial of deep brain stimulation of the ventral capsule/ventral striatum for chronic treatment-resistant depression." Biological psychiatry 78.4 (2015): 240-248.
Douglas, D. J., et al. "Linear ion traps in mass spectrometry." Mass spectrometry reviews 24.1 (2005): 1-29.
Eames, MDC, et al. "Trans-cranial focused ultrasound without hair shaving: feasibility study in an ex vivo cadaver model." Journal of therapeutic ultrasound 1.1 (2014): 1-6.
Eaton, S. M. et al. Quantum micro-nano devices fabricated in diamond by femtosecond laser and ion irradiation. Adv. Quantum Technol. 2, 1900006 (2019).
Elias, W. J. et al. A pilot study of focused ultrasound thalamotomy for essential tremor. New England Journal of Medicine, 369(7):640-648, 2013.
Escoffre, J.-M. et al. Therapeutic ultrasound, vol. 880, 33 pages, (Springer, 2015).
Exablate Transcranial MR Guided Focused Ultrasound for the Treatment of Essential Tremors—Full Text View. Version dated Sep. 23, 2021. Retrieved from https://web.archive.org/web/20210923222617/https://www.clinicaltrials.gov/ct2/show/NCT01827904?term=NCT01827904 (7 pages).
Falardeau, T. et al. Ultrasound tomography in bone mimicking phantoms: Simulations and experiments. The J. Acoust. Soc. Am. 144, 2937-2946, (2018).
FDA, Marketing clearance of diagnostic ultrasound systems and transducers, Food and Drug Administration FDA-2017-D-5372 (Jun. 27, 2019) 64 pages.
Feng, B., et al. A review on ultrasonic neuromodulation of the peripheral nervous system: enhanced or suppressed activities? Appl. Sci. 9, 1637 (2019).
Ferguson J.M. Ssri antidepressant medications: adverse effects and tolerability. Primary care companion to the Journal of clinical psychiatry, 3(1):22-27, 2001.
International Search Report and Written Opinion for Application No. PCT/US2023/010095 dated Oct. 17, 2023 (22 pages).
Younan, Y. et al. Influence of the pressure field distribution in transcranial ultrasonic neurostimulation. Medical physics, 40(8):082902, 2013.
Zhang, H., et al. Multifrequency and broadband optical antennas. In Micro-and Nanotechnology Sensors, Systems, and Applications IV, vol. 8373, 725-730 (SPIE, 2012).
Zhang, Z. et al. Paul trap mass analyzer consisting of opposing microfabricated electrode plates. Anal. Chem. 81, 5241-5248, (2009).
Zhang, Z., et al. Optimization of axial resolution in ultrasound elastography. Sensors & Transducers 174, 240-245 (2014).
Zhong, Q. et al. Polymeric perfluorocarbon nanoemulsions are ultrasound-activated wireless drug infusion catheters. Biomaterials 206, 73-86 (2019).
Pouget, P., et al. "Neuronavigated repetitive transcranial ultrasound stimulation induces long-lasting and reversible effects on oculomotor performance in non-human primates." Frontiers in Physiology 11 (2020): 1042.
Premarket Approval (PMA): EXABLATE. Version dated Jul. 9, 2021. Retrieved from https://web.archive.org/web/20210709182431/https://www.accessdata.fda.gov/scripts/cdrh/cfdocs/cfpma/pma.cfm?id=P150038 (5 pages).
Price, J. L., et al. "Neural circuits underlying the pathophysiology of mood disorders." Trends in cognitive sciences 16.1 (2012): 61-71.
Prieto, M. L., et al. "Activation of Piezo1 but not NaV1. 2 channels by ultrasound at 43 MHz." Ultrasound in medicine & biology 44.6 (2018): 1217-1232.
Pringsheim, T., Fiest, K., & Jette, N. (2014). The international incidence and prevalence of neurologic conditions: How common are they? Neurology, 83(18), 1661-1664.
Product Classification. Version dated Oct. 21, 2021. Retrieved from https://web.archive.org/web/20211021190214/https://www.accessdata.fda.gov/scripts/cdrh/cfdocs/cfPCD/classification.cfm?id=3933 (3 pages).
Pulkkinen, A. et al. Simulations and measurements of transcranial low-frequency ultrasound therapy: Skull-base heating and effective area of treatment, Physics in Medicine and Biology 56 (15) (2011) 4661-4683.
Rapoport, N. Drug-loaded perfluorocarbon nanodroplets for ultrasound-mediated drug delivery. In Therapeutic Ultrasound, 221-241 (Springer, 2016).
Raymond, S. B. et al. Acoustic transmission losses and field alterations due to human scalp hair. IEEE Transactions on Ultrason. Ferroelectr. Freq. Control. 52, 1415-1419, (2005).
Reportlinker. The Global Deep Brain Stimulation Devices Market size is expected to reach $2.3 billion by 2025, rising at a market growth of 16.1% CAGR during the forecast period. (Apr. 17, 2020). Retrieved from https://www.globenewswire.com/news-release/2020/04/17/2018084/0/en/The-Global-Deep-Brain-Stimulation-Devices-Market-size-is-expected-to-reach-2-3-billion-by-2025-rising-at-a-market-growth-of-16-1-CAGR-duringthe- forecast-period.html (9 pages).
Reznik, S. J., et al. "A double-blind pilot study of transcranial ultrasound (TUS) as a five-day intervention: TUS mitigates worry among depressed participants." Neurology, Psychiatry and Brain Research 37 (2020): 60-66.
Rief, W. et al Assessing general side effects in clinical trials: reference data from the general population, Pharmacoepidemiology and drug safety 20 (4) (2011) 405-415.
Riis, T. & Kubanek, J. Effective ultrasonic stimulation in human peripheral nervous system. IEEE Transactions on Biomed. Eng. (2021) 1-9.
Riis, T. et al. "Multifrequency-based sharpening of focal volume." Scientific Reports 12.1 (2022): 22049.
Riis, T. et al. Acoustic properties across the human skull. bioRxiv, 2021, 1-7.
Riis, T. et al. Controlled delivery of ultrasound through the head for effective and safe therapies of the brain, bioRxiv (2022.12.16. 520788) (2022).

(56) References Cited

OTHER PUBLICATIONS

Rodriguez-Cano, E. et al. Evidence for structural and functional abnormality in the subgenual anterior cingulate cortex in major depressive disorder, Psychological medicine 44 (15) (2014) 3263-3273.
Rust, M. J., et al. Sub-diffraction-limit imaging by stochastic optical reconstruction microscopy (storm). Nat. methods 3, 793-796 (2006).
Sanguinetti, J. L. et al. Transcranial focused ultrasound to the right prefrontal cortex improves mood and alters functional connectivity in humans, Frontiers in Human Neuroscience 14 (2020) 52.
Sato, T. et al. "Ultrasonic neuromodulation causes widespread cortical activation via an indirect auditory mechanism." Neuron 98.5 (2018): 1031-1041.
Scangos, K. W., et al. "State-dependent responses to intracranial brain stimulation in a patient with depression." Nature medicine 27.2 (2021): 229-231.
Schlaepfer, T. E., et al. "Deep brain stimulation of the human reward system for major depression—rationale, outcomes and outlook." Neuropsychopharmacology 39.6 (2014): 1303-1314.
Science Daily. Institute for Basic Science. (Oct. 8, 2019). How can ultrasonic brain stimulation cure brain diseases? The mechanism of neuromodulation by ultrasound is elucidated at the molecular level in astrocytes. ScienceDaily. Retrieved from www.sciencedaily.com/releases/2019/10/191008115918.htm (3 pages).
Shah, B., et al. "Unilateral Focused Ultrasound Thalamotomy in Essential Tremor: 3 year safety and efficacy data (P5.279)." (2015).
Sharifi, M. S. (2013). Treatment of Neurological and Psychiatric Disorders with Deep Brain Stimulation; Raising Hopes and Future Challenges. Basic and Clinical Neuroscience, 4(3), 266-270.
Shen, Y.-X. et al. Ultrasonic super-oscillation wave-packets with an acoustic meta-lens. Nat. communications 10, 1-7 (2019).
Shortell, M., et al. Combining Ultrasound Pulse-Echo and Transmission Computed Tomography for Quantitative Imaging the Cortical Shell of Long-Bone Replicas. Front. Mater. 4, 40, (2017).
Sinai, A., et al. "Magnetic resonance-guided focused ultrasound thalamotomy for essential tremor: a 5-year single-center experience." Journal of neurosurgery 133.2 (2019): 417-424.
Soulioti, D. E., et al. Super-Resolution Imaging through the Human Skull. IEEE Transactions on Ultrason. Ferroelectr. Freq. Control. 67, 25-36, (2020).
Thomas, J. L. & Fink, M. A. Ultrasonic beam focusing through tissue inhomogeneities with a time reversal mirror: application to transskull therapy. IEEE Transactions on Ultrason. Ferroelectr. Freq. Control. 43, 1122-1129, (1996).
Thut G. et al. A review of combined tms-eeg studies to characterize lasting effects of repetitive tms and assess their usefulness in cognitive and clinical neuroscience. Brain topography, 22(4):219-232, 2010.
Timbie, K. F., et al. (2015). Drug and gene delivery across the blood-brain barrier with focused ultrasound. Journal of Controlled Release, 219, 61-75.
Tonge, M., et al. "A detailed analysis of intracerebral hemorrhages in DBS surgeries." Clinical neurology and neurosurgery 139 (2015): 183-187.
Tufail, Y. et al. Transcranial pulsed ultrasound stimulates intact brain circuits. Neuron, 66(5):681-694, 2010.
Tye, K. M., et al. "Amygdala circuitry mediating reversible and bidirectional control of anxiety." Nature 471.7338 (2011): 358-362.
Tyler, W. J. et al Ultrasonic modulation of neural circuit activity. Current opinion in neurobiology, 50:222-231, 2018.
Velling, V. et al. Modulation of the functional state of the brain with the aid of focused ultrasonic action. Neurosci. behavioral physiology 18, 369-375 (1988).
Verhagen, L. et al. Offline impact of transcranial focused ultrasound on cortical activation in primates. Elife 8, e40541 (2019).
Viessmann, O., et al. Acoustic super-resolution with ultrasound and microbubbles. Phys. Medicine & Biol. 58, 6447 (2013).
Vignon, F., et al. Adaptive focusing for transcranial ultrasound imaging using dual arrays. The J. Acoust. Soc. Am. 120, 2737-2745, (2006).
Wang, J.B. et al. Noninvasive ultrasonic drug uncaging maps whole-brain functional networks. Neuron, 100(3):728-738, 2018.
Webb, T. D. et al. Measurements of the relationship between ct hounsfield units and acoustic velocity and how it changes with photon energy and reconstruction method. IEEE transactions on ultrasonics, ferroelectrics, frequency control 65, 1111-1124 (2018).
Webb, T. D., et al. "Platform for Incisionless, Focal, and Multisite Brain Interventions." bioRxiv (2021): 2021.05.05.442844 (12 pages).
Webb, T. D., et al. "Remus: System for remote deep brain interventions." iScience 25.11 (2022) (13 pages).
White, P. J., et al. Longitudinal and shear mode ultrasound propagation in human skull bone. Ultrasound medicine & biology 32, 1085-1096 (2006).
Widge A. et al. Deep brain stimulation for treatment-refractory mood and obsessive-compulsive disorders. Current Behavioral Neuroscience Reports, 2(4):187-197, 2015.
Williams, JBW. "A structured interview guide for the Hamilton Depression Rating Scale." Archives of general psychiatry 45.8 (1988): 742-747.
Wilson, MG et al. "Effective drug release from safe ultrasound-triggered nanocarriers." bioRxiv (2021): 2021-12 (15 pages).
World Health Organization. Pharmacological treatment of mental disorders in primary health care. World Health Organization, 2009 (82 pages).
Yoo, S.-S., et al. "Focused ultrasound modulates region-specific brain activity." Neuroimage 56.3 (2011): 1267-1275.
Kuhn, J. et al. Deep brain stimulation as a new therapeutic approach in therapy-resistant mental disorders: ethical aspects of investigational treatment. European Archives of Psychiatry and Clinical Neuroscience, 259(2):135-141, 2009.
Lancet. Life, death, and disability in 2016. The Lancet, 390(10100):1083, 2017.
Andhuis, E. Ultrasound for the brain. Nature 551, 257-259 (2017).
Larson, P. S. "Deep brain stimulation for movement disorders." Neurotherapeutics 11 (2014): 465-474.
Lea-Banks, H., et al. Ultrasound-responsive droplets for therapy: A review. J. Control. Release 293, 144-154, (2019).
Lee, S.-H., et al. Counting single photoactivatable fluorescent molecules by photoactivated localization microscopy (palm). Proc. Natl. Acad. Sci. 109, 17436-17441 (2012).
Lee, W. et al Transcranial focused ultrasound stimulation of human primary visual cortex, Scientific Reports 6 (2016) (12 pages).
Lee, W. et al. Evaluation of polyvinyl alcohol cryogel as an acoustic coupling medium for low-intensity transcranial focused ultrasound. International journal of imaging systems and technology, 24(4):332-338, 2014.
Lee, W. et al. Image-guided transcranial focused ultrasound stimulates human primary somatosensory cortex. Scientific reports, 5, 2015 (10 pages).
Lee, W. et al. Transcranial focused ultrasound stimulation of motor cortical areas in freely-moving awake rats. BMC neuroscience, 19(1):1-14, 2018.
Legon, W. et al. Neuromodulation with single-element transcranial focused ultrasound in human thalamus. Human brain mapping, 39(5):1995-2006, 2018.
Legon, W. et al. Transcranial focused ultrasound modulates the activity of primary somatosensory cortex in humans. Nature Neuroscience, 17(2):322-329, 2014.
Legon, W. et al. Transcranial focused ultrasound neuromodulation of the human primary motor cortex. Scientific reports, 8(1):1-14, 2018.
Lerosey, G., et al. Focusing beyond the diffraction limit with far-field time reversal. Science 315, 1120-1122 (2007).
Leung, S. A. et al. "A rapid beam simulation framework for transcranial focused ultrasound." Scientific reports 9.1 (2019): 7965.
Leung, S. A. et al. Transcranial focused ultrasound phase correction using the hybrid angular spectrum method. Sci. reports 11, 1-13 (2021).
Li, C., et al. In vivo Breast Sound-Speed Imaging with Ultrasound Tomography. Ultrasound Medicine Biol. 35, 1615-1628, (2009).

(56) References Cited

OTHER PUBLICATIONS

Li, Y. et al. A Magnetic Resonance-Guided Focused Ultrasound Neuromodulation System With a Whole Brain Coil Array for Nonhuman Primates at 3 T., IEEE transactions on medical imaging 39 (12) (2020) 4401-4412.

Lindenmayer J.-P. Treatment refractory schizophrenia. Psychiatric Quarterly, 71(4):373-384, 2000.

Lindsey, B. D. et al. Pitch-catch phase aberration correction of multiple isoplanatic patches for 3-D transcranial ultrasound imaging. IEEE Transactions on Ultrason. Ferroelectr. Freq. Control. 60, 463-480, (2013).

Lipsman, N. et al. Blood-brain barrier opening in alzheimer's disease using mr-guided focused ultrasound. Nat. communications 9, 1-8 (2018).

Lisanby, S. H. "Electroconvulsive therapy for depression." New England Journal of Medicine 357.19 (2007): 1939-1945.

Ma, T. et al. Multi-frequency intravascular ultrasound (ivus) imaging. IEEE transactions on ultrason-ics, ferroelectrics, frequency control 62, 97-107 (2015).

Magnin, P. A., et al. Frequency compounding for speckle contrast reduction in phased array images. Ultrason. imaging 4, 267-281 (1982).

Maimbourg, G., et al. 3d-printed adaptive acoustic lens as a disruptive technology for transcranial ultrasound therapy using single-element transducers. Phys. Medicine & Biol. 63, 025026 (2018).

Malone Jr, D. A., et al. "Deep brain stimulation of the ventral capsule/ventral striatum for treatment-resistant depression." Biological psychiatry 65.4 (2009): 267-275.

Mayberg, H. S. et al. Deep brain stimulation for treatment-resistant depression, Neuron 45 (5) (2005) 651-660.

Mayo Clinic. Deep brain stimulation. Version dated Sep. 17, 2021. Retrieved from https://web.archive.org/web/20210917020752/https://www.mayoclinic.org/tests-procedures/deep-brain-stimulation/about/pac-20384562?p=1 (5 pages).

McDannold, N., et al. Elementwise approach for simulating transcranial mri-guided focused ultrasound thermal ablation. Phys. Rev. Res. 1, 033205 (2019).

Medeiros, L. F., et al Neurobiological effects of transcranial direct current stimulation: a review, Frontiers in psychiatry 3 (2012) 110.

Meng, Y. et al. Applications of focused ultrasound in the brain: From thermoablation to drug delivery. Nat. Rev. Neurol. 1-16 (2020).

Meng, Y. et al. Current and emerging brain applications of mr-guided focused ultrasound, Journal of therapeutic ultrasound 5 (1) (2017) 26, 1-9.

Menz, M. D., et al. Precise neural stimulation in the retina using focused ultrasound. The J. Neurosci. 33, 4550-4560 (2013).

Mitchell, K. T., et al. "Benefits and risks of unilateral and bilateral ventral intermediate nucleus deep brain stimulation for axial essential tremor symptoms." Parkinsonism & Related Disorders 60 (2019): 126-132.

Moosa S. et al. "Essential Tremor: Lesions." Stereotactic and Functional Neurosurgery: Principles and Applications (2020): 297-310.

Morris, L. S., et al. "Ketamine normalizes subgenual cingulate cortex hyper-activity in depression." Neuropsychopharmacology 45.6 (2020): 975-981.

Mueller, J. et al. Numerical evaluation of the skull for human neuromodulation with transcranial focused ultrasound. Journal of neural engineering, 14(6):066012, 2017.

Munoz, F. et al. Long term study of motivational and cognitive effects of low-intensity focused ultrasound neuromodulation in the dorsal striatum of nonhuman primates, Brain Stimulation 15 (2022) 360-372.

Nanou E. et al. Calcium channels, synaptic plasticity, and neuropsychiatric disease. Neuron, 98(3):466-481, 2018.

Naor, O. et al. "Ultrasonic neuromodulation." Journal of neural engineering 13.3 (2016): 031003.

Nicolo, P. et al. "Variability of behavioural responses to transcranial magnetic stimulation: Origins and predictors." Neuropsychologia 74 (2015): 137-144.

O'Reilly, M. A. et al. A super-resolution ultrasound method for brain vascular mapping. Med. Phys. 40, 1-7, (2013).

Oh, S.-J. et al. Ultrasonic neuromodulation via astrocytic TRPA1. Curr. Biol. 29, 3386-3401 (2019).

Ozcelik, A. et al. Acoustic tweezers for the life sciences. Nat. Methods 15, 1021-1028, (2018).

Pal, S. (Jan. 19, 2018). Incidence and Prevalence of Major Neurologic Disorders. Retrieved from https://www.uspharmacist.com/article/incidence-and-prevalence-of-major-neurologic-disorders (4 pages).

Pei, Y. et al. High resolution imaging beyond the acoustic diffraction limit in deep tissue via ultrasound-switchable nir fluorescence. Sci. reports 4, 1-7 (2014).

Perlmutter J. et al. Deep brain stimulation. Annu. Rev. Neurosci., 29:229-257, 2006.

Phipps, M. A., et al. "Considerations for ultrasound exposure during transcranial MR acoustic radiation force imaging." Scientific reports 9.1 (2019): 16235.

Plaksin, M. et al. "Cell-type-selective effects of intramembrane cavitation as a unifying theoretical framework for ultrasonic neuromodulation." eneuro 3.3 (2016) 1-16.

Posse, P.R. et al. "The problem of treatment-resistant psychiatric disorders." Management of treatment-resistant major psychiatric disorders (2012): 3-22.

Ferrera, V. P., et al. (Feb. 1, 2018). Focused ultrasound for noninvasive brain stimulation. Accessed on Mar. 29, 2023. Retrieved from https://grantome.com/grant/NIH/R01-MH112142-02 (4 pages).

Focused Ultrasound Foundation. Overview webpage. Version dated Nov. 18, 2021. Retrieved from https://web.archive.org/web/20211118073849/https://www.fusfoundation.org/the-foundation/overview (9 pages).

Folloni, D. et al. Manipulation of subcortical and deep cortical activity in the primate brain using transcranial focused ultrasound stimulation. Neuron 101, 1109-1116 (2019).

Fomenko, A. et al. Low-intensity ultrasound neuromodulation: An overview of mechanisms and emerging human applications, Brain stimulation (2018) 1209-1217.

Fomenko, A. et al. Systematic examination of low-intensity ultrasound parameters on human motor cortex excitability and behavior. Elife, 9:e54497, 2020.

Fouragnan, E. F. et al. The macaque anterior cingulate cortex translates counterfactual choice value into actual behavioral change. Nature neuroscience, 22(5):797-808, 2019.

Freire, R.C., et al. "Treatment-resistant panic disorder: a systematic review." Expert opinion on pharmacotherapy 17.2 (2016): 159-168.

Frinking, PJA, et al. "Scattering properties of encapsulated gas bubbles at high ultrasound pressures." The Journal of the Acoustical Society of America 105.3 (1999): 1989-1996.

Fry F.J. et al. Acoustical properties of the human skull. The Journal of the Acoustical Society of America, 63(5):1576-1590, 1978.

Fry F.J. et al. Ultrasonic diagnostic system for interactive interrogation of adult brain through intact skull. Investig. radiology 17, 463-469, (1982).

Fymat, A. L. (2018). Neurological Disorders and the Blood Brain Barrier: 2. Parkinson and Other Movement Disorders. Current Opinions in Neurological Science, 2(1), 362-383.

Gâteau, J. et al. Transcranial ultrasonic therapy based on time reversal of acoustically induced cavitation bubble signature. IEEE Transactions on Biomed. Eng. 57, 134-144, (2010).

Gavrilov, L. Focused ultrasound stimulation of the peripheral nervous system: Physical basis and practical applications. Int. J. Mod. Physics: Adv. Theory Appl. 1, 45-118 (2016).

Gavrilov, L. R., et al. A study of reception with the use of focused ultrasound. i. effects on the skin and deep receptor structures in man. Brain research 135, 265-277 (1977).

George, M. S., et al. "A controlled trial of daily left prefrontal cortex TMS for treating depression." Biological psychiatry 48.10 (2000): 962-970.

Ghanouni, P. et al. Transcranial MRI-guided focused ultrasound: a review of the technologic and neurologic applications. Am. J. Roentgenol. 205, 150-159 (2015).

(56) References Cited

OTHER PUBLICATIONS

Gibson, B. C., et al. "Increased excitability induced in the primary motor cortex by transcranial ultrasound stimulation." Frontiers in neurology (2018): 1007.

Giordano, M., et al. "Comparison between deep brain stimulation and magnetic resonance-guided focused ultrasound in the treatment of essential tremor: a systematic review and pooled analysis of functional outcomes." Journal of Neurology, Neurosurgery & Psychiatry 91.12 (2020): 1270-1278.

Gooch, C. L., et al. (2017). The burden of neurological disease in the United States: A summary report and call to action. Annals of Neurology, 81(4), 479-484.

Goodman, W. K. et al Deep brain stimulation for intractable obsessive compulsive disorder: pilot study using a blinded, staggered-onset design. Biological psychiatry, 67(6):535-542, 2010.

Grasin, E. et al. Realistic sham tms, Brain Stimulation: Basic, Translational, and Clinical Research in Neuromodulation 12 (2) (2019) 418.

Green, A. (Ed.). (Jul. 2018). Deep Brain Stimulation: A Way to Rebalance Neural Circuits. Retrieved from https://www.neuromodulation.com/deep-brain-stimulation (2 pages).

Guasch, L., et al. Full-waveform inversion imaging of the human brain. npj Digit. Medicine 3, 1-12, (2020).

Guo, H. et al. Ultrasound produces extensive brain activation via a cochlear pathway, Neuron (2018): 1020-1030.

Gustafsson, M. G. Surpassing the lateral resolution limit by a factor of two using structured illumina-tion microscopy. J. microscopy 198, 82-87 (2000).

Gustafsson, M. G., et al. I5m: 3d widefield light microscopy with better than 100nm axial resolution. J. microscopy 195, 10-16 (1999).

Guy, A. W., et al. Therapeutic applications of electromagnetic power. Proc. IEEE 62, 55-75 (1974).

Hall, J. F-number, numerical aperture, and depth of focus. In Encyclopedia of Optical and Photonic Engineering, Second Edition, 1-4 (CRC Press, 2015).

Hamner, M. B., et al. "Treatment-resistant posttraumatic stress disorder: strategies for intervention." CNS spectrums 9.10 (2004): 740-752.

Hansen, P. C. Discrete Inverse Problems: Insight and Algorithms, 95-98 (SIAM, 2010).

Harary, M., et al. "Volumetric analysis of magnetic resonance-guided focused ultrasound thalamotomy lesions." Neurosurgical focus 44.2 (2018): E6.

Hell, S. W. et al. Breaking the diffraction resolution limit by stimulated emission: stimulated-emission-depletion fluorescence microscopy. Opt. letters 19, 780-782 (1994).

Herrmann, C. S., et al. "Transcranial alternating current stimulation: a review of the underlying mechanisms and modulation of cognitive processes." Frontiers in human neuroscience 7 (2013): 279.

Holtzheimer, P. E., et al. "Subcallosal cingulate deep brain stimulation for treatment-resistant depression: a multisite, randomised, sham-controlled trial." The Lancet Psychiatry 4.11 (2017): 839-849.

Huang, Y. et al. Measurements and models of electric fields in the in vivo human brain during transcranial electric stimulation. elife, 6:e18834, 2017.

Ingram, A. et al. Cognitive side effects of brief pulse electroconvulsive therapy: a review, The journal of ECT 24 (1) (2008) 3-9.

INSIGHTEC. Exablate Neuro overview page. Version dated Jun. 9, 2020. Retrieved from https://web.archive.org/web/20200609052833/https://www.insightec.com/us/products/exablate-neuro/overview (4 pages).

Jaffe, D. H., et al. "The humanistic and economic burden of treatment-resistant depression in Europe: a cross-sectional study." BMC psychiatry 19 (2019): 1-11.

Jensen, JA et al. "Calculation of pressure fields from arbitrarily shaped, apodized, and excited ultrasound transducers." IEEE transactions on ultrasonics, ferroelectrics, and frequency control 39.2 (1992): 262-267.

Jo, Y. et al. "Microelectromechanical systems-based neurotools for non-invasive ultrasound brain stimulation." Chronobiology in Medicine 1.2 (2019): 55-59.

Johansen-Berg, H. et al. Anatomical connectivity of the subgenual cingulate region targeted with deep brain stimulation for treatmentresistant depression, Cerebral cortex 18 (6) (2008) 1374-1383.

Karakatsani, M. E., et al. (2019). Amelioration of the nigrostriatal pathway facilitated by ultrasound-mediated neurotrophic delivery in early Parkinsons disease. Journal of Controlled Release, 303, 289-301.

Kessler, S. K., et al. "Differences in the experience of active and sham transcranial direct current stimulation." Brain stimulation 5.2 (2012): 155-162.

Khalighinejad, N. et al. A basal forebrain-cingulate circuit in macaques decides it is time to act. Neuron 105, 370-384 (2020).

Kim, H. et al. Focused ultrasound-mediated non-invasive brain stimulation: examination of sonication parameters. Brain stimulation, 7(5):748-756, 2014.

Klucinec, B., et al. "Transmissivity of coupling agents used to deliver ultrasound through indirect methods." Journal of Orthopaedic & Sports Physical Therapy 30.5 (2000): 263-269.

Kubanek, J. et al. Remote, brain region-specific control of choice behavior with ultrasonic waves, Science Advances 6 (21) (2020) eaaz4193.

Kubanek, J. et al. Ultrasound elicits behavioral responses through mechanical effects on neurons and ion channels in a simple nervous system. Journal of Neuroscience, pp. 1458-17, 2018.

Kubanek, J. et al. Ultrasound modulates ion channel currents. Scientific Reports, 6:24170, Apr. 2016.

Kubanek, J. Neuromodulation with transcranial focused ultrasound. Neurosurg. Focus. 44, E14 (2018).

Foiret J, et al. Improving plane wave ultrasound imaging through real-time beamformation across multiple arrays. Sci. Rep. 2022; 12:1-14.

Goss SA, et al. Sparse random ultrasound phased array for focal surgery. IEEE Trans. Ultrason. Ferroelectr. Freq. Control. 1996;43:1111-1121.

International Search Report and Written Opinion for Application No. PCT/US2023/019759 dated Aug. 17, 2023 (8 pages).

Kim H, et al. Miniature ultrasound ring array transducers for transcranial ultrasound neuromodulation of freely-moving small animals. Brain Stimul. 2019;12:251-255.

Kim S, et al. Transcranial focused ultrasound stimulation with high spatial resolution. Brain Stimul. 2021;14:290-300.

Mehić E, et al. Increased anatomical specificity of neuromodulation via modulated focused ultrasound. PLOS ONE. 2014;9:1-13.

Peralta, L., et al. "Impact of aperture, depth, and acoustic clutter on the performance of coherent multi-transducer ultrasound imaging." Applied Sciences 10.21 (2020): 7655.

Riis, T., et al. Acoustic properties across the human skull. Ultrasonics 119, 106591, (2022).

Sumi, C. et al. "Effective ultrasonic virtual sources which can be positioned independently of physical aperture focus positions." Reports in Medical Imaging (2010): 45-59.

Sutton J, et al. Design, characterization, and performance of a dual aperture, focused ultrasound system for microbubble-mediated, non-thermal ablation in rat brain. J. Acoust. Soc. Am. 2015; 138:1821-1821.

\* cited by examiner

SYSTEMS AND METHODS FOR MODULATION OF DEEP BRAIN CIRCUITS

CROSS-REFERENCE TO RELATED APPLICATIONS

This application is a non-provisional of and claims the benefit of U.S. Provisional Patent Application No. 63/296,252, filed on Jan. 4, 2022, the contents of which are incorporated herein by reference.

FIELD

The present disclosure relates to systems and methods for applying and regulating ultrasound to a specified target in the human brain.

BACKGROUND

Approximately one third of patients across mental and neurological conditions are treatment-resistant. Neuromodulation has the potential to provide a targeted reset of the malfunctioning circuits. However, current neuromodulation approaches have been limited by two major barriers. First, the exact neural circuits involved in mental and neurological disorders are poorly understood and appear to vary from individual to individual. This uncertainty has limited robust applications of deep brain stimulation to such patients. Second, common conditions such as depression-, anxiety-, and pain-related disorders involve neural networks situated deep in the brain, including the limbic, basal ganglia, and brain stem networks. These deep brain sources complicate treatments using current noninvasive neuromodulation approaches. For instance, electroconvulsive therapy modulates the deep brain structures using large currents that induce brain-wide seizures. This broad activation often results in cognitive side effects such as memory loss. Transcranial magnetic stimulation can likely modulate deep brain networks via connections with the stimulated cortical regions, but this indirect engagement has contributed to variable response.

Ultrasound-based neuromodulation has the potential to modulate deep brain targets selectively and at high spatiotemporal resolution.

Compared with studies in small animal models, ultrasound-based neuromodulation has shown limited effectiveness when applied through the head of humans. It was determined that the intensity of neuromodulatory ultrasound is attenuated by human skull alone by a factor of 4.5-64, depending on skull segment and individual. This enormous variability in the attenuation factor makes it impossible to provide a confident estimate on the delivered intensity. As a consequence, studies in humans—to mitigate the risk of harm to the brain—are forced to take a "worst-case scenario" approach, assuming the least possible attenuation. This conservative approach, necessary for safety, has stifled effectiveness.

Moreover, effective and safe treatments of brain disorders require selective delivery of ultrasound into circumscribed brain regions or individual nuclei. Current single-element transducers used for neuromodulation only provide a cigar-shaped beam that commonly extends over several centimeters, thus providing only limited spatial specificity. In addition, these solutions do not have the precision and flexibility of phase arrays, which complicates selective delivery, fine-tuning of the targeting, and systematic applications to multiple targets. The lack of precision and flexibility limit the use of existing solutions to patients with disorders of deep brain circuits.

Accordingly, a device that compensates for the human skull and delivers ultrasound into specified deep brain targets at high spatiotemporal resolution is desired.

SUMMARY

Transcranial focused ultrasound provides noninvasive and reversible approaches for precise and personalized manipulations of brain circuits, with the potential to transform understanding of brain function and treatments of brain dysfunction. Ultrasound can be focused through the intact skull and scalp into specified deep brain regions that can span a few millimeters in diameter.

Because ultrasound reaches a target in microseconds, ultrasonic arrays have the capacity to stimulate multiple sites simultaneously or in fine temporal sequences. The precise focusing on command opens unique new possibilities to systematically modulate malfunctioning circuits in each individual. In addition, arrays of transducers can focus ultrasound into specified brain targets programmatically, without moving the device or the subject.

However, as noted above, the effectiveness and safety of these approaches have been limited by the human head, which attenuates and distorts ultrasound strongly and unpredictably. This barrier is due to the strong and unpredictable attenuation of ultrasound by the head and limited targeting precision of existing devices. To address these issues, an ultrasonic phased-array device has been developed that compensates for the ultrasound distortions by the head and delivers ultrasound into specified target/s at high spatiotemporal resolution. The device can validate target engagement inside MM and can be repeatedly used outside of Mill.

To address the ultrasound attenuation issue, a "Relative Through-Transmit" (RTT) approach that directly measures and compensates for the attenuation and distortion of a given skull and scalp has been developed. RTT has been implemented in hardware and demonstrated that it accurately restores the operator's intended intensities inside ex-vivo human skulls. Moreover, this functionality enabled effective and intensity-dependent transcranial modulation of nerves and effective release of defined doses of propofol inside the skull. Accordingly, the present disclosure provides a tool to noninvasively and effectively modulate specific neural circuits deep in the human brain to provide treatment options to the millions of people who are resistant to current treatments.

A device, as disclosed herein, provides diagnostic information to guide deep brain stimulation implants, furthers the understanding of the function of the human brain, and provides new means to induce a durable circuit reset in treatment-resistant patients.

In some implementations, the systems and methods described herein provide high-precision ultrasonic treatments that can be used, for example, in mental health or neurological clinics. In some implementations, the systems provide mechanisms for controlling the ultrasound dose delivered through the head to produce predictable effects in the target regions. In some implementations, the systems enable multi-focal operation that predictably modulates specific brain regions based on the specific needs of a patient.

In some implementations, the system includes a head-worn transducer array device that includes 64 to 1,024 transducer elements that are inserted in a 3D-printed frame with geometry that is optimized for a particular multi-focal operation in a specific individual. The delivery of ultrasound into deep brain targets is possible owing to minimal attenuation of ultrasound by brain tissue. The head and the skull in particular, however, de-phase and attenuate ultrasound waves. Accordingly, in some implementations, the systems and methods described herein use ultrasound itself to correct (also referred to as "compensate") for the aberration of ultrasound by the head. This way, the head aberration is measured directly and accurately and does not require additional head scans such as CT or MM. In particular, the method performs ultrasound RTT measurements through each respective segment of the given head. This provides the phase and amplitude values that are used to correct for the aberrations of each segment of the particular head. The amplitudes of the respective ultrasonic transducers are scaled and the phases shifted such as to deliver undistorted, deterministic intensity into the treatment target. In some implementations, specific features of the through-transmit waveform may be optimized to maximize the accuracy of the detection of the ultrasound energy delivered through the head and, thus, the accuracy of the correction for the head.

In some implementations, the systems and methods described herein are configured and adapted for treatment of anxiety and depression-related disorders, including post-traumatic stress disorder. These disorders involve aberrant connectivity of two deep brain regions—the subgenual cingulate and the amygdala—with neighboring circuits. A few dozens of seconds of low-intensity ultrasound aimed into the cingulate and the amygdala can induce durable changes in the associated circuits. In some implementations, the systems and methods described herein are configured to target those regions (e.g., using human cadavers as a model).

In some implementations, the systems and methods described herein are configured and adapted for treatment of thalamic nuclei such as those involved in pain. These disorders involve aberrant connectivity of thalamic nuclei insular cortex, cingulate cortex, the nucleus accumbens, and the ventral tegmental area. A few dozens of seconds of ultrasound aimed into these circuits modulate pain thresholds. In some implementations, the systems and methods described herein are configured to target those regions (e.g., using human cadavers as a model).

In some implementations, the targeting of these regions can be validated using fMRI BOLD (Blood-Oxygen-Level-Dependent imaging), MM thermometry or MRI acoustic radiation force imaging. These imaging sequences visualize the region impacted by the ultrasound and thus can increase the reproducibility of the ultrasonic therapies and minimize potential off-target effects.

In some implementations, Mill may be used to establish subject-specific anatomy of the head and the brain.

In one embodiment, the disclosure provides a method of applying transcranial ultrasound to a target brain location. At least one transmitting ultrasound transducer is driven to generate ultrasound waves to achieve an intended ultrasound energy at a target location in a free field volume, which corresponds to the target brain location. Ultrasound waves exiting the free field volume are measured by at least one receiving ultrasound transducer positioned at a fixed distance and orientation relative to the at least one transmitting ultrasound transducer on a opposite side of the free field volume. The head is then positioned between the transmitting and receiving ultrasound transducers and the transmitting ultrasound transducers are again driven to generate the same ultrasound waves into the head and the receiving ultrasound transducers measure the ultrasound waves exiting the head, which are altered due at least in part to a presence of a head in an ultrasound path between the transmitting ultrasound transducers and the receiving ultrasound transducers. One or more adjusted ultrasound waveforms are then determined based on differences between the measured ultrasound waves through the free field volume and the measured altered ultrasound waves through the head, wherein the adjusted ultrasound waves compensate for the attenuation and phase shift due to obstacles in the ultrasound path in order to deliver the actual ultrasonic stimulation energy at the target brain location to approach the intended ultrasonic stimulation energy at the target location. The transmitting ultrasound transducers are then driven to generate the adjusted ultrasound waves into the head.

In another embodiment, the disclosure provides an ultrasound-based neurostimulation system that includes a head-worn device and a controller. The head-worn device includes at least one array of ultrasound transducers including ultrasound transducers positioned on opposite sides of the head. The controller is configured to determine a set of ultrasound waves to be transmitted by the ultrasound transducers to achieve an intended ultrasonic stimulation energy at a target location within the volume. The controller drives the first set of ultrasound transducers and captures the propagating ultrasound waves using a second set of ultrasound transducers on an opposite side of the volume. This is performed twice: once in free field while the head-worn device is not applied to the head, and once while the head-worn device is applied to the head. The controller compares the free field measurements and the through-transmit measurements to determine attenuation and phase shift in the ultrasound waves due at least in part to a presence of a skull in the ultrasound path. The controller determines an adjusted set of ultrasound waves that compensates for the determined attenuation and the determined phase shift in order to achieve the intended ultrasonic stimulation energy at the target location within the volume while the head-worn device is applied to the head. The controller drives both sets of transducers according to the determined adjusted set of ultrasound waves while the head-worn device is applied to the head.

In yet another embodiment, the disclosure provides a method for applying deterministic ultrasound dose into a target brain location by driving an ultrasound transducer array to perform through-transmit ultrasound measurements through a subject's head and without a subject's head. Based on the through-transmit ultrasound measurements, the attenuation and phase shift of the ultrasound due to the head, compared to the head absent, are determined. The corrected amplitude and phase values are determined for each ultrasound transducer, and the ultrasound transducer array is then driven based on the adjusted amplitude and phase values to achieve an intended ultrasonic stimulation energy at a target brain location within the skull.

Other aspects of the invention will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The systems and methods presented in the examples below provide a noninvasive ultrasound-based neuromodulatory device that may be used, for example, for treatment and/or diagnosis of neurological and mental disorders. The device is worn on the head and is coupled at several points around the skull. This positioning allows the device to deliver ultrasonic waves from transducers into specified deep brain targets. The device is controlled by an operator who can select specific brain areas to target with the ultrasound waves. A treatment plan for the patient may be generated to automatically control which transducer(s) deliver the ultrasonic wave(s) to the deep brain target(s). The device performs a compensation procedure to correct for the ultrasound obstacles, which commonly include the skull, hair, and ultrasound coupling, and emits from the individual transducer arrays waves with amplitude and timing such that the ultrasound reaches the defined target with the intended intensity.

In some implementations, the systems are configured to correct for the ultrasound aberration of the skull by using the ultrasound itself and of the same frequency as that used for the therapies. The device takes a direct measurement of the skull, as opposed to an estimate, which allows for a more accurate, safer, and more effective treatments. The device obtains this measurement by measuring actual attenuation and de-phasing of the ultrasound via relative through-transmit measurements through the skull. The system then takes these measured attenuation and phase values and compensates for them by adjusting the amplitude and phase for each of its elements. The measurements of the ultrasound skull aberrations using ultrasound itself provide accurate compensation for the delivered ultrasound intensity into specified brain targets, sharpen the ultrasound focus, and so lead to more precise, safer, and more effective treatments.

In some implementations, the head-worn device includes 256 transducer elements that are attached to a custom, patient-specific 3-D printed frame. This modular design allows for the targeting of specific brain regions in each patient.

Figure 1:
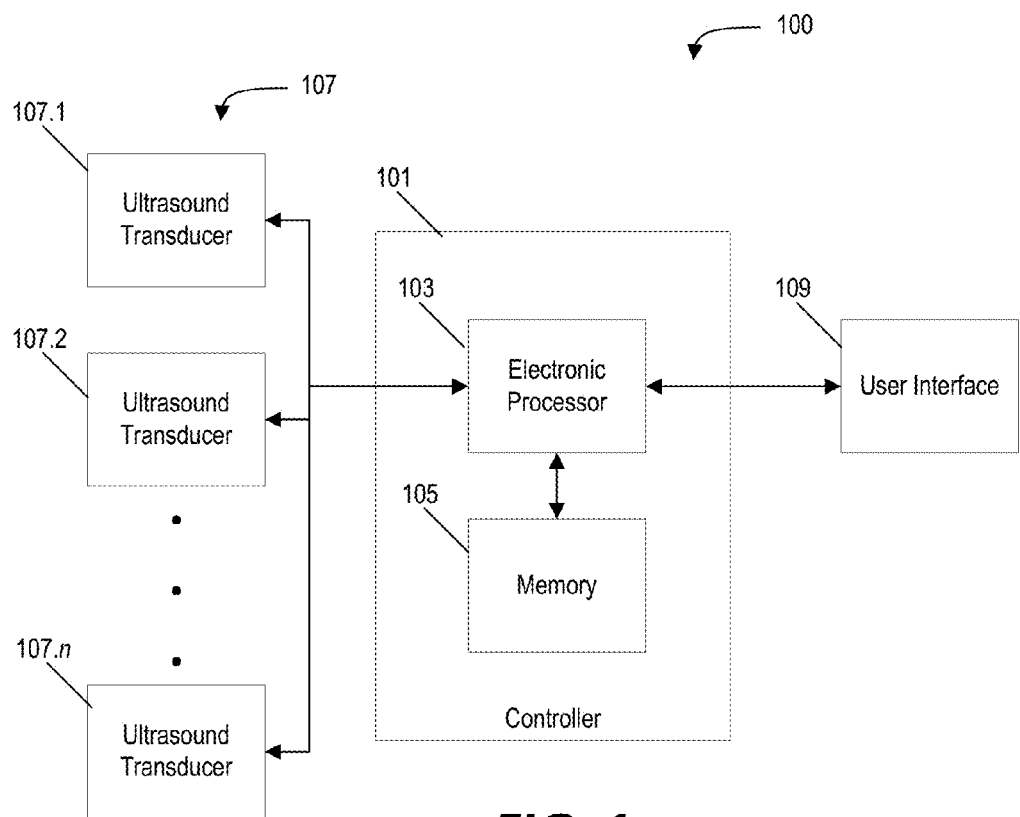
FIG. 1 is a block diagram of a system for applying an ultrasonic stimulus according to one implementation.

FIG. 1 illustrates an example of an ultrasound-based neurostimulation system 100 for deep brain therapy. The system 100 includes a controller 101, which includes an electronic processor 103 and a non-transitory computer-readable memory 105. The electronic processor 103 is communicatively coupled to the memory 105 and configured to store data to the memory 105 and access stored data from the memory 105. The memory 105 also stores computer-executable instructions that, when executed by the electronic processor 103, provide the functionality of the controller 101 including, for example, the functionality described herein. Although the example of FIG. 1 illustrates only one memory 105 in other implementations, the system may utilize multiple different memory modules including, for example, a local memory, an external storage device, and/or a remote or cloud-based memory system. Similarly, in different implementations, the system 100 may utilize one or more electronic processors implemented in one or more different computing devices. In some implementations, the controller 101 may be implemented as an application specific controller device while, in other implementations, the controller 101 may be provided as a desktop, laptop, or tablet computer. In still other implementations, the controller

101 may include multiple different control devices including, for example, an electronic controller incorporated into or directly coupled to the head-worn device described below and a computer communicatively coupled to the electronic controller. Accordingly, unless otherwise specified, the controller 101 may include one or more computing devices and/or control circuits, one or more electronic processors, and one or more memories.

As illustrated in the example of FIG. 1, the controller 101 is communicatively coupled to a plurality of ultrasound transducers 107 including ultrasound transducers 107.1, 107.2, and 107.*n*. In the specific examples described herein, the plurality of ultrasound transducers 107 includes 256 ultrasound transducers arranged in one or more arrays, which are incorporated into a head-worn device.

As described in further detail below, the controller 101 is configured to selectively and controllably cause the ultrasound transducers 107 in the array(s) to transmit an ultrasound wave and to define/control the parameters of the transmitted ultrasound wave. The controller 101 is also configured to receive output data from other ultrasound transducers in the array. In this way, the ultrasound transducers 107 are operated by the controller 101 to transmit and receive ultrasound waves. In some implementations, the controller 101 is configured to electronically communicate with each ultrasound transducer 107 directly while, in other implementations, the controller 101 is indirectly coupled to the plurality of ultrasound transducers 107 through a data acquisition and/or signal routing device (not pictured) that is either incorporated into the controller 101 or provided as a separate additional device.

Figure 2:
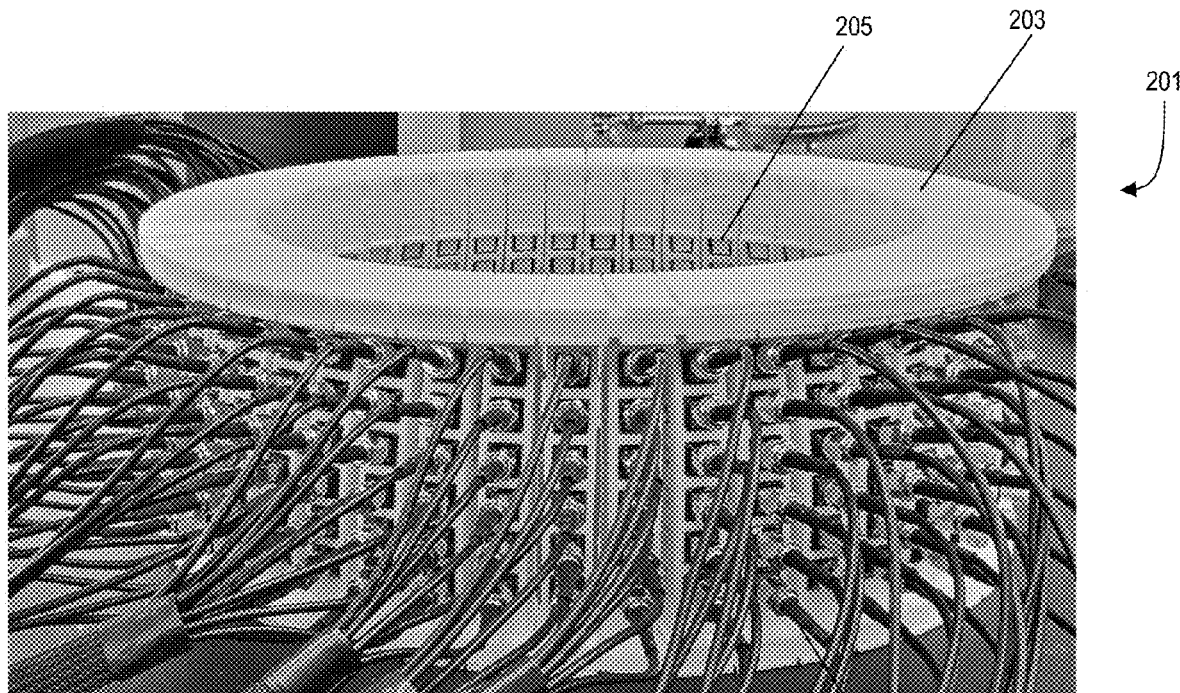
FIG. 2 is a perspective view of one example of a head worn transducer array device of the system of FIG. 1.

FIG. 2 illustrates a first example of a head-worn transducer array device 201. The head-worn device 201 includes a 3D printed frame 203 that is sized to fit around the upper portion of a head of a subject. In this example, the 3D printed frame 203 is generally tubular in shape and supports a plurality of ultrasound transducers 205 arranged in an array around the interior circumference of the 3D printed frame 203 such that the ultrasound transducer array encircles the head of the subject when worn. Each ultrasound transducer 205 is communicatively coupled to the controller 101 (of FIG. 1) via a cable 207 attached to the rear of the ultrasound transducer 205. In some implementations, the 3D printed frame 203 may be custom-sized according to the anatomical dimensions of the intended subject. Additionally or alternatively, the position and orientation of the ultrasound transducers 205 supported by the 3D printed frame 203 may be adjusted to target one or more specific locations in a brain of the intended subject. In some implementations, this may be done by adjusting the position of the ultrasound transducers 205 manually to adjust a relative angle of the ultrasound transducer 205 while, in other implementations, the 3D printed frame 203 is configured to receive and support each ultrasound transducer 205 in a position and orientation specific to the one or more target locations in the brain of the intended subject. Also, in some implementations, the relative angle of each transducer in the transducer array is known such that different target locations can be stimulated by selected different combinations of ultrasound transducers that will intersect at the target location (as discussed below). Accordingly, in some implementations, near-arbitrary brain regions can be targeted by selecting different combinations of ultrasound transducers to transmit the ultrasound waves into the brain tissue.

Figure 3:
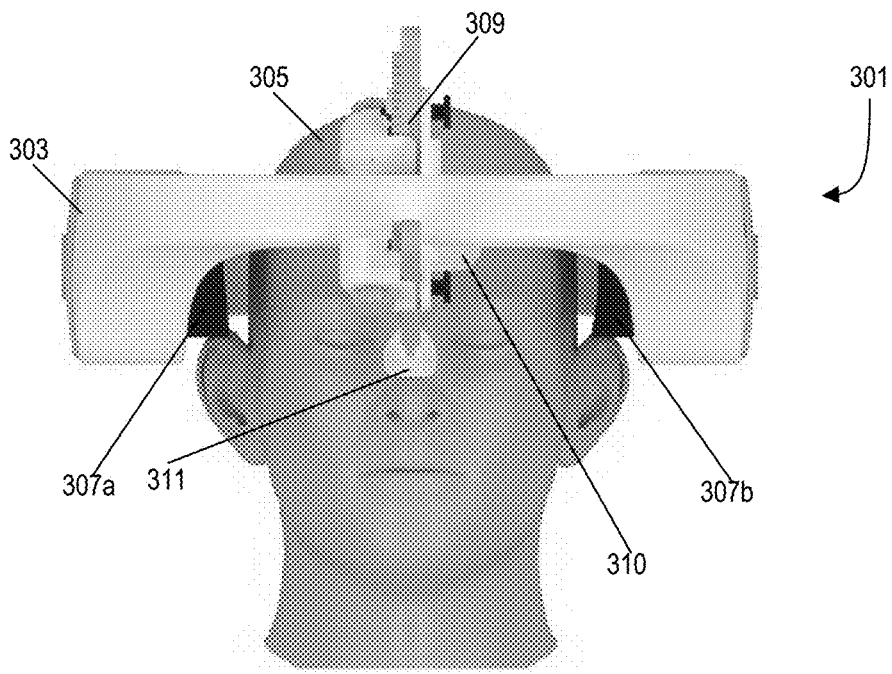
FIG. 3 is a perspective view of another example of a head worn transducer array device of the system of FIG. 1.
Figure 4:
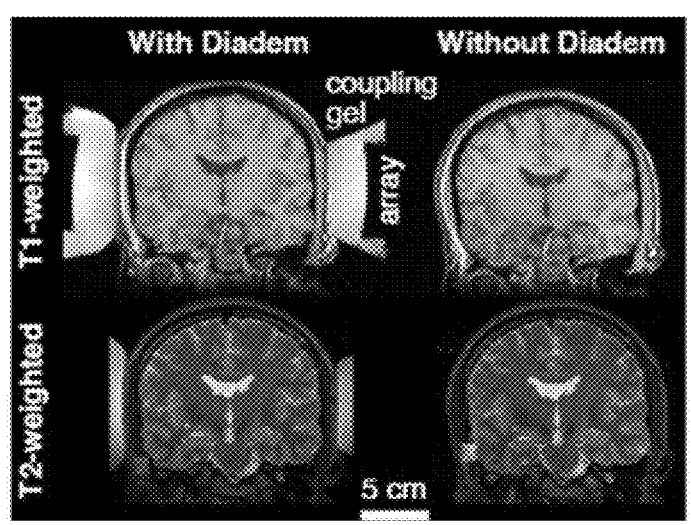
FIG. 4 is a series of MRI images captured of a subject wearing the head worn transducer array device of FIG. 3 and without wearing the head-worn transducer array device.

FIG. 3 illustrates an alternative example of a head-worn transducer array device 301. In this example, the head-worn device includes a frame 303 sized to be worn around the head 305 of the subject and includes two separate transducer arrays 307*a*, 307*b* positioned on opposite sides of the 3D printed frame. As shown in FIG. 3, the ultrasound transducer arrays 307*a*, 307*b* are positioned on opposite sides of the head 305 of the subject when the head-worn device 301 is worn by the subject. In the example of FIG. 3, the head-worn device 301 also includes an adjustable support mechanism 309 that is configured for adjustable positioning of a forehead support pad 310 and a nose support pad 311. The forehead support pad 310 and the nose support pad 311 can be adjusted to conform to the anatomical geometry of the head 305 of the intended subject in order to hold the head-worn device 301 in place during use. In some implementations, the head-worn transducer array device (e.g., the head-worn device 201 or the head-worn device 301) is constructed from MRI-compatible materials and cabling, and as illustrated in FIG. 4, the use of the head-worn transducer array during MM does not cause any detectable image distortion in the captured MR images. In addition, in some implementations, the head-worn transducer array device (e.g., the head-worn device 201 or the head-worn device 301) may be waterproof.

In one construction, the device 301 includes two spherical phased array transducers mounted to a plastic, MM compatible frame such that they are positioned opposite to each other and separated by a distance of 187 mm. The array elements are made of PMN-PT material, with surface area of 6 mm×6 mm, and operate at a fundamental frequency of 650 kHz. The two spherically focused arrays have a radius of 165 mm, 126 elements in a 9×14 element grid, with inter-element spacing of 0.5 mm. Each array has a height of 55 mm and a width of 86 mm, spanning an area of 47.3 cm$^2$. These transducers are configured to deliver ultrasound through the parietal and temporal bones of the subject. Specifically, the transducers are orientated in parallel to the left and right sides of the subject's head. The transducers are driven by a programmable system (e.g., Vantage256, Verasonics). The transducers are coupled to the subject with a hydrogel. Standard ultrasound coupling gel can be applied to the interfaces between the transducer and the hydrogel, and the hydrogel and the head. The application of the ultrasound gel was not critical given the presence of the hydrogel but can improve transmission approximately by a factor of 2.

In some implementations, the systems described herein are used to diagnose and treat the neural sources of neurological or mental disorders systematically and in a personalized manner. The head-worn transducer array device 201, 301 is operated to non-invasively modulate specified brain targets at high spatiotemporal resolution and in a multi-focal manner. Additionally, in some implementations, the systems are configured to compensate for the skull and, thereby, deposit into a specified brain target a deterministic dose of ultrasonic energy for effective and safe applications. In some implementations, the system is configured to apply ultrasonic energy to a brain target using superposition of ultrasonic waves as illustrated in the example of FIG. 5A, which uses the head-worn device 301 of FIG. 3.

In some implementations, the systems described herein are used to activate or release biocompatible nanoparticles carrying one or more therapeutics (e.g., propofol) for treatment of neurological or mental disorders of the patient. The head-worn transducer array device 201, 301 is operated to non-invasively modulate specified locations in the skull to allow for the ultrasound waves to activate and release the therapeutic in the specified brain location of the patient. Additionally, in some implementations, the systems are configured to compensate (e.g., by utilizing the RTT method described herein) for the skull and, thereby, provide a therapeutically effective release to the patient when ultrasound is applied through the skull.

Figure 5A:
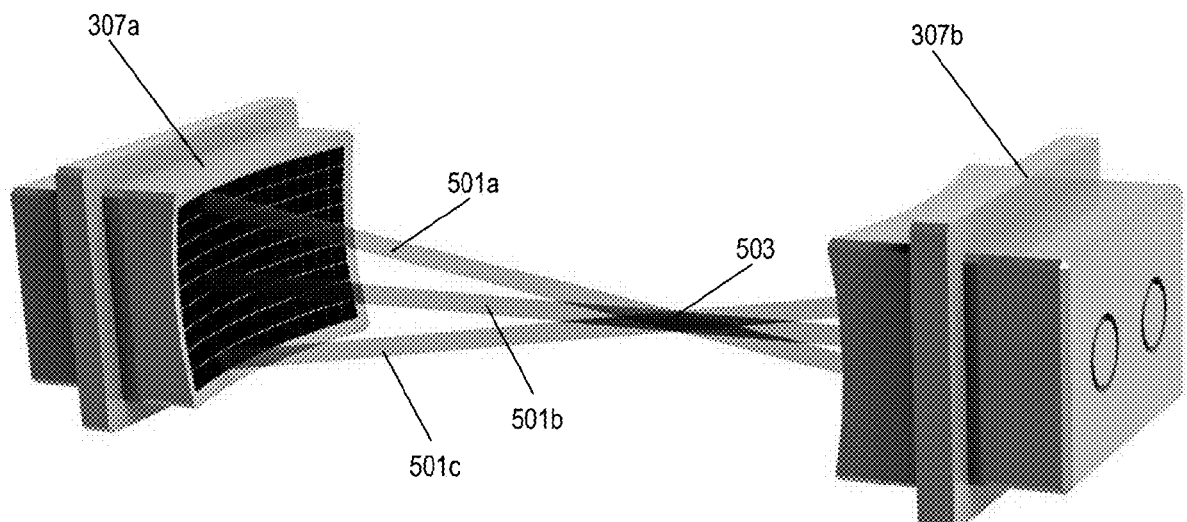
FIG. 5A is a perspective view of the transducer arrays of the head-worn transducer array device of FIG. 3 transmitting ultrasound waves through a free field volume.

In the example of FIG. 5A, the system is operated to transmit ultrasonic waves from three different ultrasound transducers of the first ultrasound transducer array 307a. The ultrasonic waves are emitted at different relative trajectory angles such that the first ultrasound wave 501a, the second ultrasound wave 501b, and the third ultrasound wave 501c all intersect at a target location 503. At the target location 503, the superpositioning of the three ultrasound waves 501a, 501b, 501c results in an intended ultrasonic energy being applied at the target location 503. Once past the target location 503, the three ultrasound waves 501a, 501b, 501c continue along their respective trajectories until they reach the second ultrasound transducer array 307b. The output of the transducers in the second ultrasound transducer array 307b are monitored to determine the delivered intensity of the ultrasound waves 501a, 501b, 501c that reach the second ultrasound transducer array 307b.

Figure 5B:
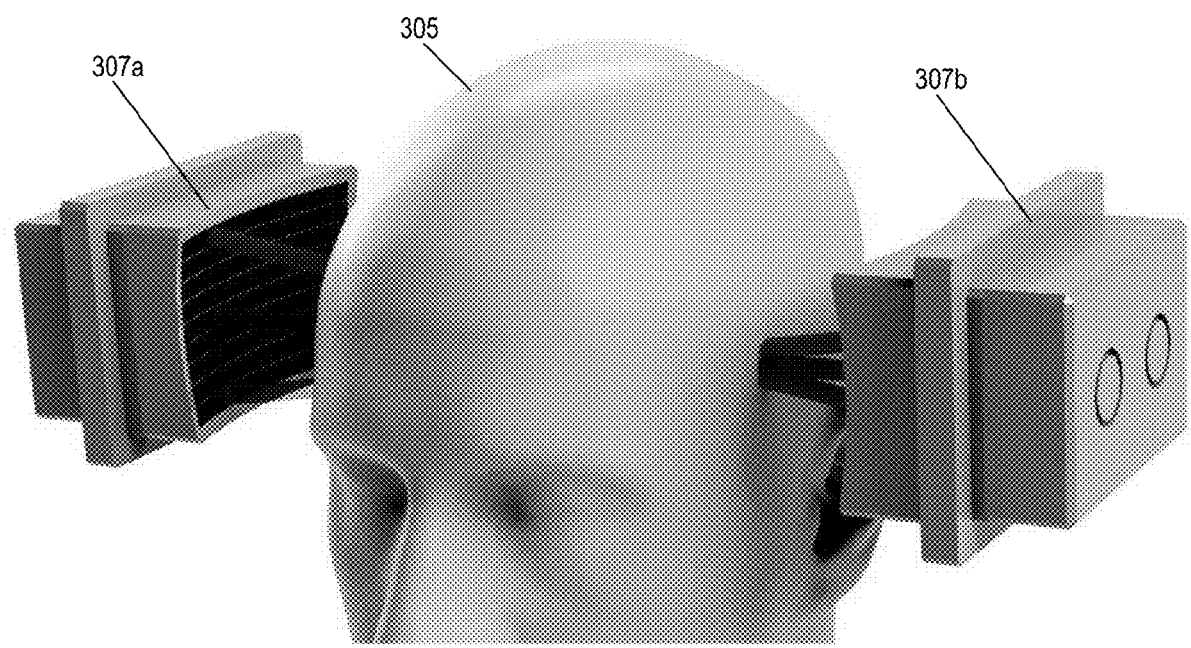
FIG. 5B is a perspective view of the transducer arrays of the head worn transducer array device of FIG. 3 transmitting ultrasound waves through a head of a subject.

FIG. 5A illustrates the operation of the head-worn device 301 in a "free field" area (i.e., where there is only water positioned between the ultrasound transducer arrays 307a, 307b). When the head-worn device 301 is positioned on the head 305, as illustrated in FIG. 5B, the ultrasound waves 501a, 501b, 501c converge at a location (e.g., target location 503) within the brain to apply the ultrasound energy via superpositioning. However, obstacles in the ultrasound path between the first ultrasound transducer array 307a and the second ultrasound transducer array 307b affect the ultrasound waves 501a, 501b, 501c and, in turn, affect the ultrasound energy applied at the target location 503. Obstacles in the ultrasound path during use of the head-worn device 301 may include, for example, anatomical features such as the skull and scalp of the subject, hair, the coupling interface between the head-worn device 301 and the head 305, and bubbles in the coupling interface.

Figure 5C:
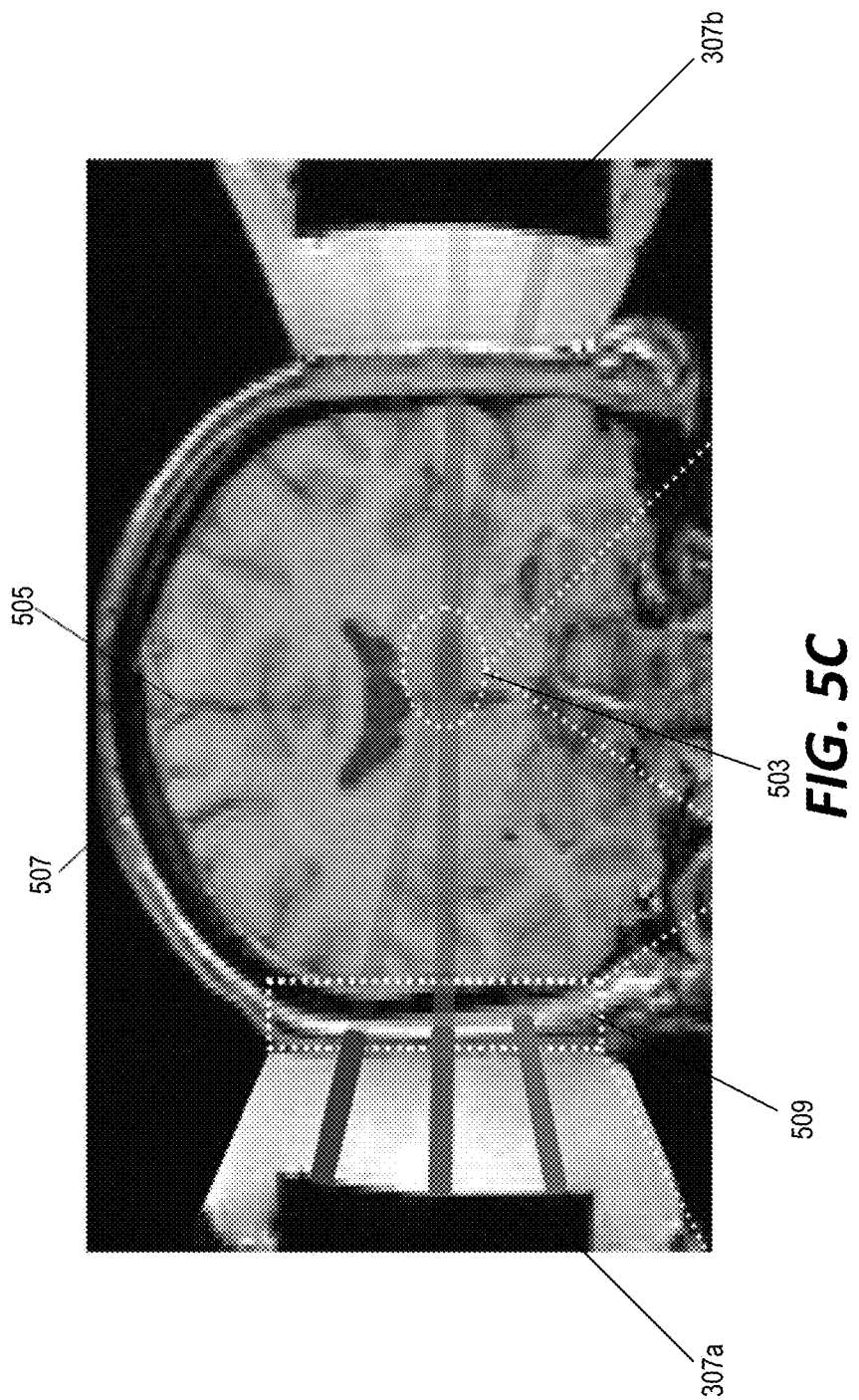
FIG. 5C is superposition of the ultrasonic beams from the transducer arrays on the MRI image.
Figure 6:
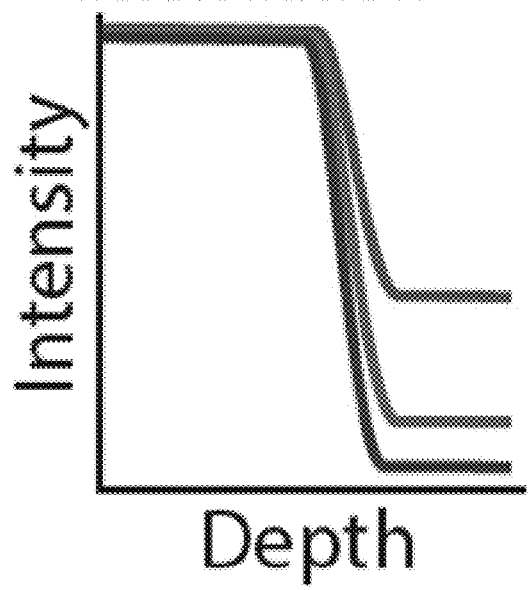
FIG. 6 is a graph of the intensity attenuation by individual segments of the skull.
Figure 7:
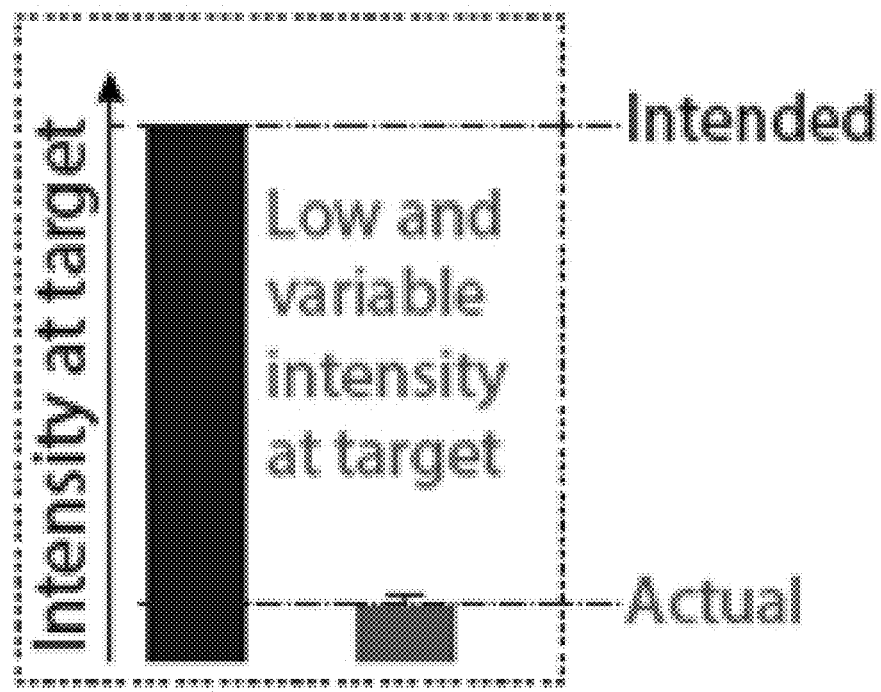
FIG. 7 is a graph of intended intensity and actual intensity of the transmitted ultrasound waves at a target location due to attenuation at the ultrasound target shown in FIG. 5C.
Figure 8:
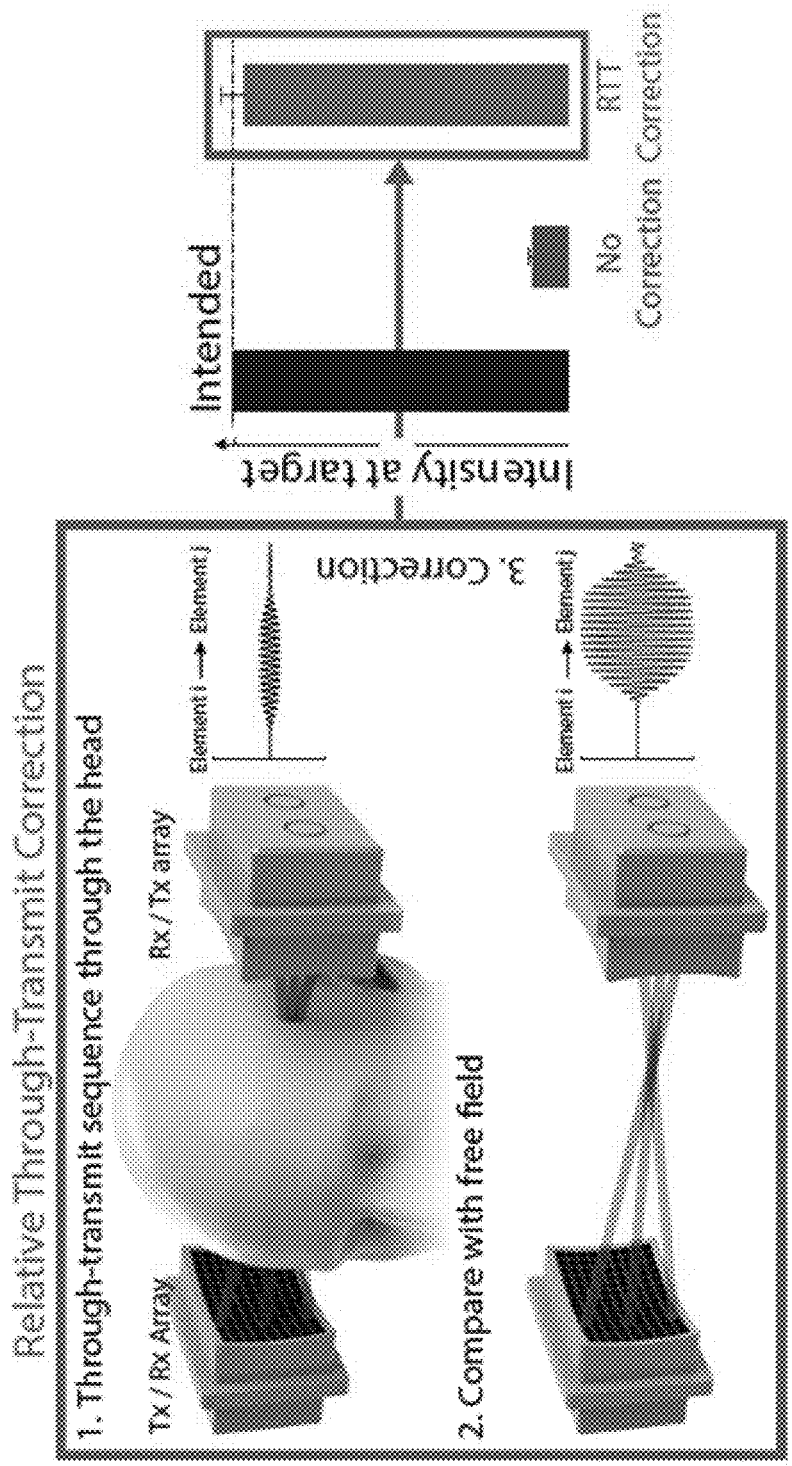
FIG. 8 schematically illustrates a method of measuring ultrasound aberrations by the skull according to an embodiment of the present disclosure.

For example, as shown in FIG. 5C, the ultrasound waves emitted by the first ultrasound transducer array 307a must pass through a portion of the skull 509 before entering the brain and reaching the target location 503 within the brain. FIG. 6 illustrates an example of the relative intensity of the ultrasonic energy of each of the three ultrasound waves as the ultrasound waves pass through the skull at 509. FIG. 7 shows the difference between the "intended intensity" at the target location 503 (i.e., the intensity of the ultrasonic energy at the target location 503 in a free-field area of FIG. 5A) compared to the "actual intensity" at the target location 503 (i.e., the intensity of the ultrasonic energy at the target location 503 when the head-worn device 301 is worn during use). FIG. 8 shows the ultrasonic energy of one of the ultrasound waves projected from a first transducer j of the first ultrasound transducer array 307a as measured by a second transducer i of the second ultrasound transducer array 307b when the head-worn device 301 is worn during use (a shown in FIG. 5B) and with a free-field area (as shown in FIG. 5A). These graphs demonstrate that the presence of the skull and other obstacles along the ultrasound path causes attenuation and dephasing (e.g., speedup) of the ultrasound waves. In fact, in some implementations, the attenuation caused by the human skull prevents the ultrasound waves from generating any significant neurostimulation, example of which can be observed in the red bar in FIG. 12 for which the herein proposed compensation for the skull is not applied. Neurostimulation is recovered when the herein compensation is applied.

To achieve an intended amount of ultrasonic energy at a target location within the brain, the electronic controller 101 in some implementations is configured to determine an appropriate compensation for the effect of the skull and other obstacles in the ultrasound path. In some such implementations, the system measures and compensates for the ultrasound attenuation and dephasing by all obstacles in the ultrasound path directly using ultrasound itself and of the same frequency as that used for the therapy. In some implementations, the necessary compensation values are established relativistically by contrasting the ultrasound arrival times and amplitudes with the head present (FIG. 5B) and with the head absent (FIG. 5A). By using this mechanism to compensate for all obstacles in the ultrasound path (including, for example, the coupling interface of the head-worn device to the head, bubbles, the anatomical structures of the head, skull, brain tissue, etc.) the system is able to deliver ultrasonic energy into a target location at the same intensity as that measured in water (head absent).

Figure 9:
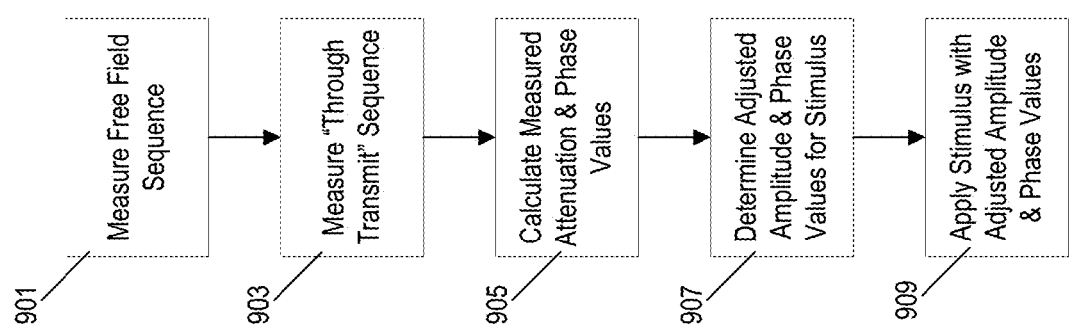
FIG. 9 is a flowchart of a method for applying an ultrasound stimulus to a target location in a brain of a subject after adjusting the stimulus wave to compensate for attenuation and phase alterations caused by the skull of the subject.

FIG. 9 illustrates an example of a method executed by the controller 101 for determining and applying appropriate compensation to the transmitted ultrasound beams to achieve a desired/intended ultrasound energy at a target location within the brain. First, the ultrasound energy is measured via a "free field" sequence (step 901) in which ultrasound waves are transmitted by a first set of transducers through a "free field" area (e.g., only water between the ultrasound transducers) and are measured by a second set of transducers on the opposite end of the ultrasound path. Second, the head-worn device 301 is positioned on the head and a "through transmit" sequence is measured (step 903) in which the same ultrasound waves are transmitted from the same first set of transducers and measured by the same second set of transducers; however, in the "through transmit" sequence, the ultrasound path proceeds through the head/skull of the subject. The measurements from these two sequences are compared to quantify the attenuation and phase value differences (step 905). An appropriate phase and amplitude adjustment is determined based on the attenuation and phase value differences (step 907). Ultrasound waveforms to each transducer are applied using the determined amplitude and phase adjustments (step 909). Additional details around the "through transmit" methodology are described below in EXAMPLE 2.

Relative to the measurements in water (e.g., the free field sequence measurements), the obstacles in the ultrasound path (e.g., the skull) attenuate the beam emitted from each transducer element i by a factor of $A_i$ and speed up the beam by a relative time $\tau_i$. The compensation method of FIG. 9 estimates these values and corrects for them, scaling the amplitude of each ultrasound wave beam by a factor of $$\frac{1}{A_i},$$

and delaying emission by $\tau_i$. In some implementations, the reconstruction of the speedup times $\tau_i$ and attenuation $A_i$ are solved separately.

For attenuation, in some implementations, the controller 101 is configured to solve a system of equations:

$$\ln A_{ij} = k_{ij} \ln A_i + k_{ji} \ln A_j \qquad (1)$$

where $A_{ij}$ are the relative attenuation values measured by the through-transmit method for ultrasound propagating through both sides of the skull. The proportionality constants $k_{ij} =$ $$\frac{1}{\cos(\beta_{ij})}$$

in these equations express the extended path that ultrasound travels through the skull under an angle $\beta$ between transducer elements i and j. The attenuation values through the two opposite segments of the skull are multiplicative—hence, the logarithmic formulation for attenuation. This linear system of equations can be represented in a matrix form as K x=b, where K is a matrix of the $k_{ij}$ coefficients, x is a vector of the sought values x=[$A_1, A_2, \ldots, A_{256}$], and b is a vector of the measured values $A_{ij}$. A solution x minimizes the sum of squared errors (b−Kx)'×(b−Kx).

In some implementations, the controller 101 is configured to calculate phase shifts as follows. For all pairs of tranducers, $h_{ij}(t)$ correspond to the received signal on the $i^{th}$ transducer after a brief pulse is emitted from transducer j. This transmit-receive may be performed for all elements both in water $h_{ij}^W(t)$ (i.e., the free field measurements) and through the skull $h_{ij}^S(t)$ (i.e., the through-transmit measurements). For each receive transducer i of the total transducers, the controller 101 determines the transmit delays in water $\tau_{ij}^W$ (i.e., the free field measurements) that focuses onto element i all transmit-receive waveforms $h_{ij}^W(t)$, $1 \leq j \leq N$.

Let the summation of these waveforms under any vector of timeshifts $\vec{\tau}$ be denoted as:

$$f(h_{i,+}, \vec{\tau}) = \Sigma_j^J h_{ij}(t) \times \delta(t - \vec{\tau}_j) \quad (2)$$

where:

$$h_{i,+} = [h_{i1}(t), h_{i2}(t), \ldots, h_{iN}(t)] \quad (3)$$

The aim is to find delays $\vec{\tau}$ that account for the speed up relative to water. Each wave received at element i in water should be delayed by $\vec{\tau}$ compared to the waves through the skull after applying delays $\vec{\tau}$ to compensate for the speedup in front of the transmitting elements. In some implementations, the controller 101 is configured to identify these delays $\vec{\tau}$ by optimizing the equation:

$$\operatorname*{argmax}_{\vec{\tau}} \sum_i^N \max\left(f(h_{i,*}^W, \vec{\tau}_{i,*}^W) \times f(h_{i,*}^S, \vec{\tau}_{i,*}^W + \vec{\tau} + \vec{1}\vec{\tau}_i)\right) \quad (4)$$

Figure 10:
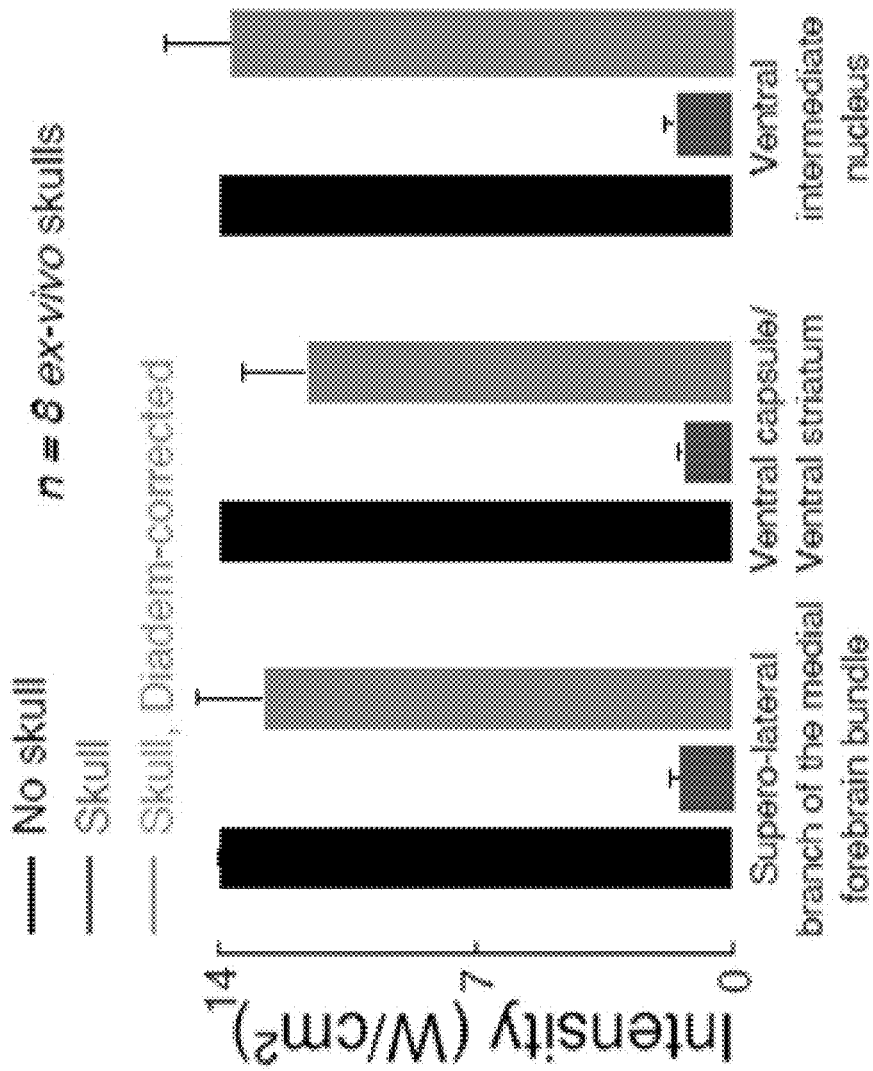
FIG. 10 is a series of graphs illustrating the measured intensity of a transmitted ultrasound beam without a skull present, the measured intensity of the same transmitted ultrasound beam attenuated by human skulls (n=8), and the measured intensity of ultrasound beam through the skull after the correction according to the method of FIG. 9. The bars show how the method of FIG. 9 recovers the intended intensity at deep brain targets.

FIG. 10 illustrates the intensity resulting from the compensation method of FIG. 9 at three different target locations within the brain: the supero-lateral branch of the medial forebrain bundle, the ventral capsule/ventral striatum, and the ventral intermediate nucleus (VIM). For each experiment, the graph illustrates the intensity of the ultrasonic energy at the target location without the skull (i.e., the free field measurements), the intensity at the same target location when the same ultrasound beams are applied through a skull (i.e., the through transmit measurements), and the intensity at the same target location when the compensated ultrasound beams are applied to the head (i.e., the "Diadem-corrected" stimulus measurements). The graphs represent a quantification of the compensation accuracy in eight different specimens, mean+/−s.e.m. As illustrated in these graphs, the intended peak intensity (14 W/cm$^2$) delivered into each target is severely attenuated by the skull for all targets (see the red bar in FIG. 10). However, the compensation method of FIG. 9 is able to accurately recover the intended intensity values (see the green bar in FIG. 10).

Figure 12:
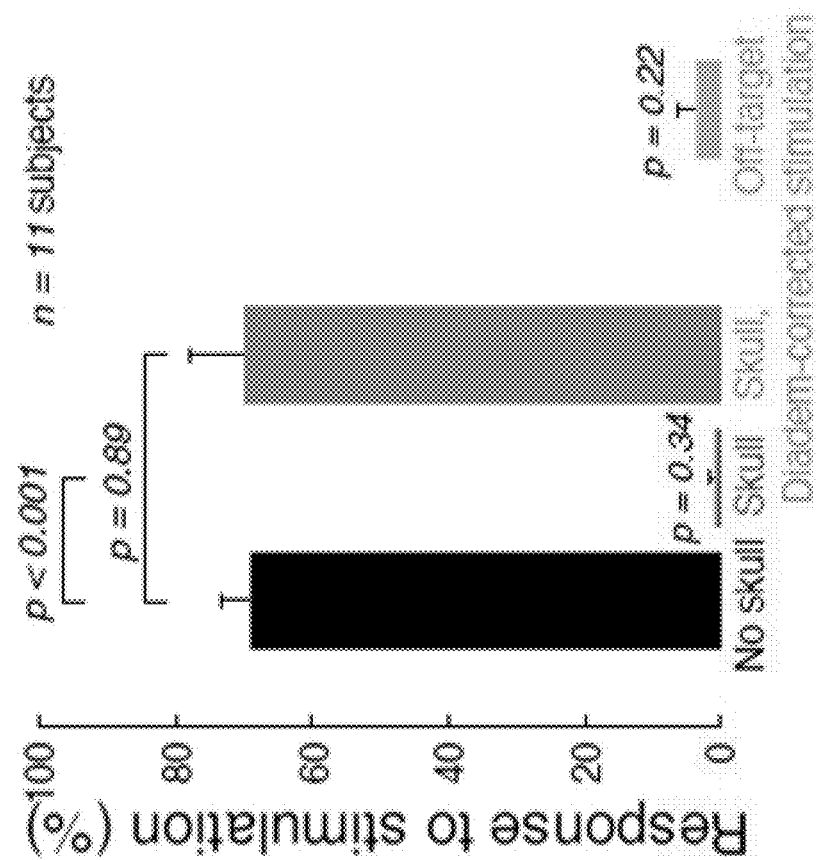
FIG. 12 is a graph illustrating the subjects' response data for the highest ultrasound pressure shown in FIG. 11, separately for the skull absent, skull present, skull present with the ultrasound waves compensated according to the method of FIG. 9, and for stimulation that is 10 mm off target.
Figure 11:
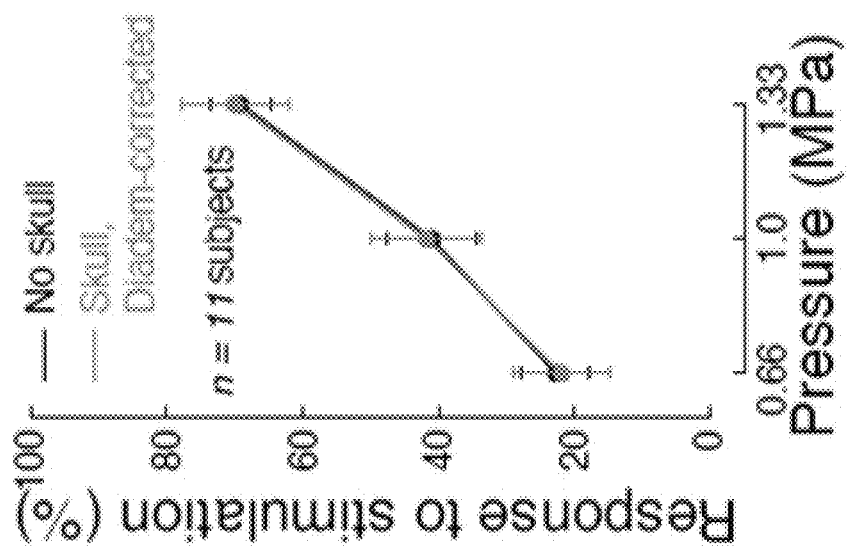
FIG. 11 is a graph illustrating the accuracy of the correction of the method of FIG. 9 with respect to stimulation of subjects' nerves of the thumb positioned inside a skull.

FIGS. 11 and 12 illustrate the results of another set of experiments using the compensation method of FIG. 9. The head-worn device 301 was configured to target nerves and nerve endings of the thumb in 11 participants. The thumb was secured in a position of the VIM inside an ex-vivo skull. The device delivered into the target a 300 ms stimulus at a frequency of 650 kHz. The data were collected without the skull, through the ex-vivo skull, and through the skull after applying the correction for the skull. The experiment also included applying a stimulus 10 mm below the finger (i.e., an "off-target" sham stimulation). Subjects had their eyes closed and wore noise-cancelling headphones. Subjects were blinded to whether the correction, no correction, or sham stimulus was applied, and reported any nociceptive response. A nociceptive response is an indication of stimulation of nerves and nerve endings.

The graph of FIG. 11 illustrates the dose-response relationship of the stimulation. A two-way ANOVA detected a significant modulation by the ultrasound pressure ($F(2,60)=25.11$, $p<0.001$). The correction for the skull was accurate as there was no significant difference ($p=0.96$) between the response to the no-skull stimulus and the response to the skull-corrected stimulus. The graph of FIG. 12 illustrates a quantification of the effects at the highest applied stimulus pressure (1.33 MPa). The p-values provide the significance of respective two-tailed t-tests. As illustrated in FIG. 12, the response percentages were nearly identical for the no-skull stimulus and the skull-corrected stimulus while the response percentage for the uncorrected stimulus applied through the skull was nearly zero. This result explicitly demonstrates the importance of the compensation; without it, there is essentially no neurostimulation. Additionally, the response percentage to the off-target stimulation was also nearly zero—suggesting that stimulation applied by the head-worn device 201, 301 would likely not have discernible stimulation effects outside of the intended target area.

Figure 13:
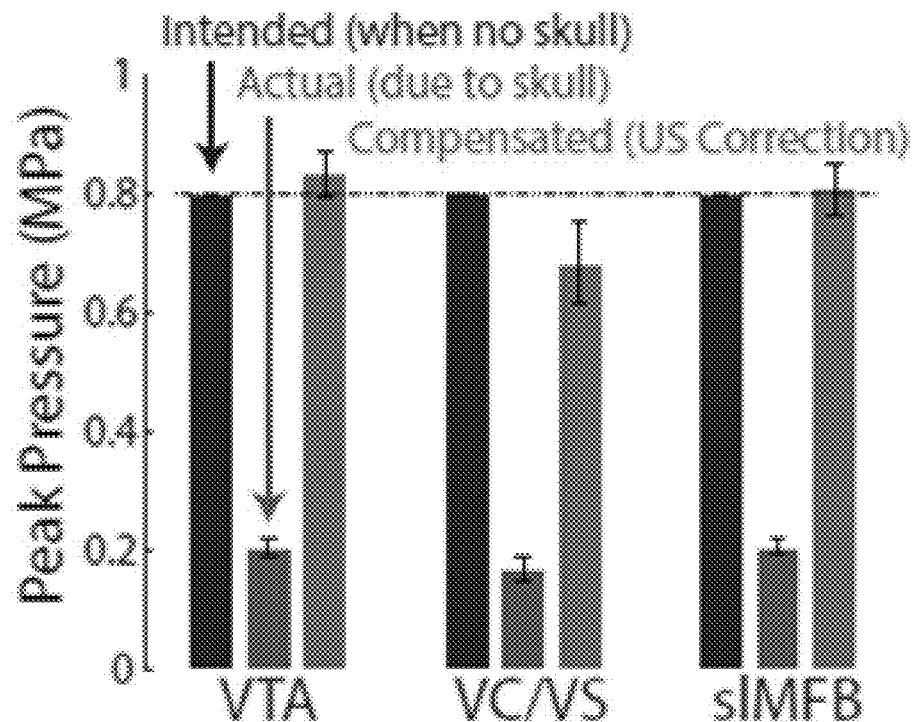
FIG. 13 is a graph illustrating the measured peak pressure for an intended stimulation, an actual stimulation (after attenuation by the skull), and the stimulation compensated according to the method of FIG. 9.
Figure 14:
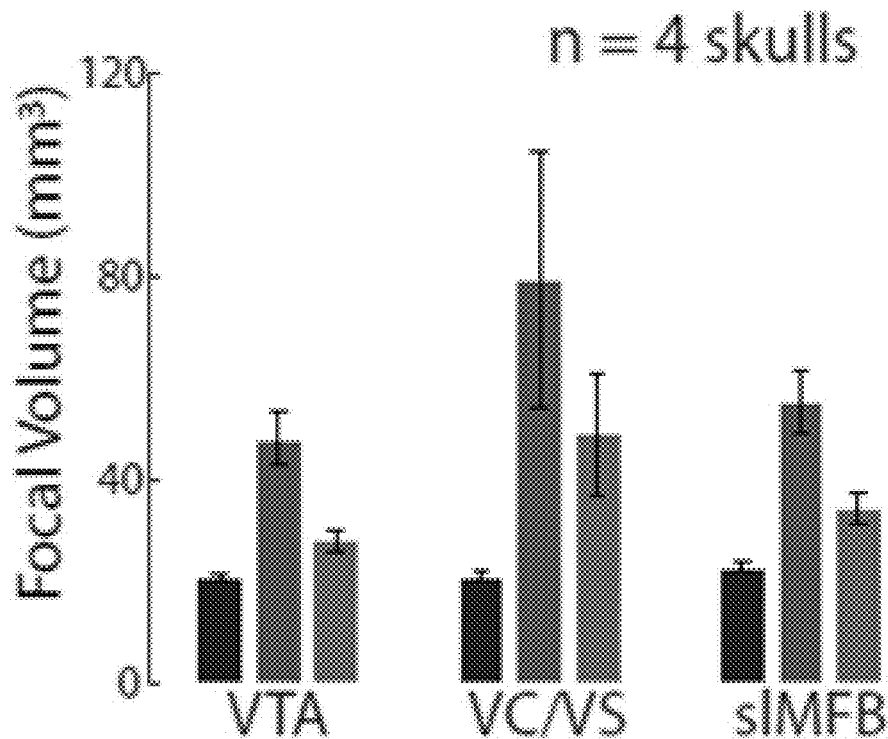
FIG. 14 is a graph illustrating variations in the focal volume of the region stimulated by the applied ultrasound waves due to distortions by the skull and the compensation of the ultrasound wave according to the method of FIG. 9.

FIGS. 13 and 14 illustrate the results of yet another stimulation experiment using a head-worn transducer array device. FIG. 13 illustrates the measured peak pressure at each of three different target sites (ventral tegmental area (VTA), ventral capsule/ventral striatum (VC/VS), superolateral branch of the medial frontal bundle (slMFB)) for the free field measurements (i.e., "Intended (when no skull)"), the uncompensated through-target measurements (i.e., "Actual (due to skull)"), and the compensated through-target measurements (i.e., "Compensated (US Correction)"). This figure confirms the notion of FIGS. 10-12 that the compensation procedure described in FIG. 9 is critical for the delivery of deterministic and effective ultrasound dose. FIG. 14 illustrates a quantification of the focal volume for the same three target areas under the same three stimulation conditions. As illustrated by FIG. 14, the presence of the skull within the ultrasound path not only attenuates the ultrasound wave, but also increases the focal volume of the stimulation provided by the superpositioned ultrasound beams. However, FIG. 14 also illustrates that the focal volume can be reduced by applying the compensation according to the method of FIG. 9. Accordingly, FIG. 14 demonstrates that, in addition to compensating for attenuation and phase shift caused by obstacles in the ultrasound path, the methods described above in reference to the example of FIG. 9 can also be adapted to adjust and tune the focal volume of the applied stimulus. In some implementations, the controller 101 is configured to coordinately optimize the adjusted compensation applied to the transmitted ultrasound beams to bring both the corrected peak pressure and the focal volume as close to the intended values as possible. Under some conditions, an adjustment that brings the focal volume closer to the target may move the corrected peak pressure further from the peak pressure target, various different optimization techniques may be employed by the controller 101 to determine an optimized solution for balancing deviations from the peak pressure and focal volume targets when both targets cannot be achieved simultaneously.

Figure 15:
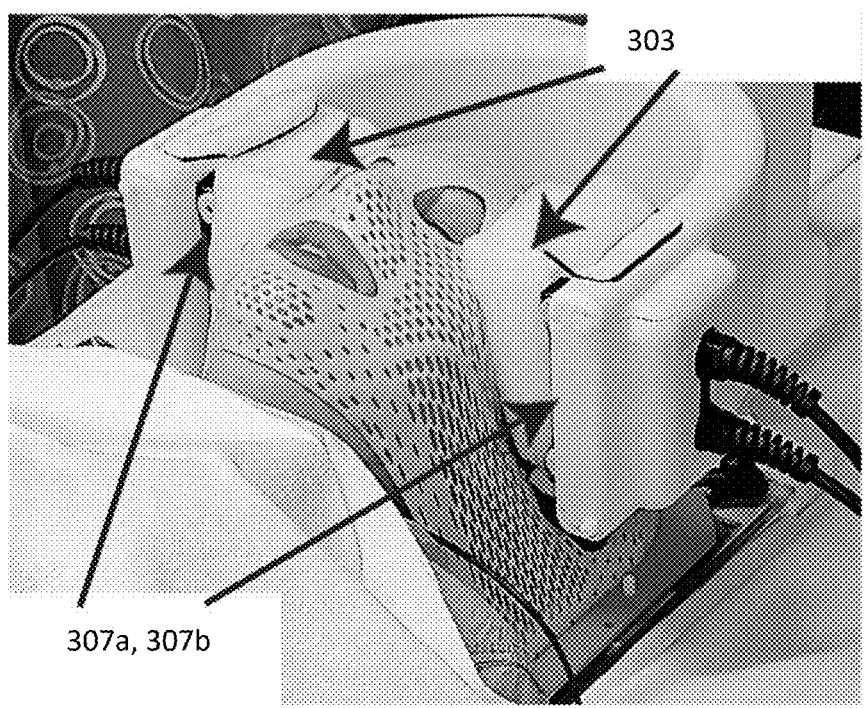
FIG. 15 is a perspective view of one example of a head worn transducer array device of the system of FIG. 1 applied to a patient.

FIG. 15 illustrates an alternative example of a head-worn transducer array device 301. In this example, the head-worn device includes a frame sized to be worn around the head of the subject and includes two separate transducer arrays (black) positioned on opposite sides of the frame. As shown in FIG. 3, the ultrasound transducer arrays are positioned on opposite sides of the head of the subject when the head-worn device is worn by the subject. In the example of FIG. 3, the head-worn device 301 also includes an adjustable support mechanism that is configured for adjustable positioning. In some implementations, the head-worn transducer array device (e.g., the head-worn device 201 or the head-worn device 301) is constructed from MRI-compatible materials and cabling, and as illustrated in FIG. 17C-G and FIG. 33, the use of the head-worn transducer array during MM does not cause any detectable image distortion in the captured MR images. In addition, in some implementations, the head-worn transducer array device may be waterproof.

Example 1: Demonstrating Effective Neuromodulation Using Head-Worn Device in Humans The device was applied to a patient with treatment-resistant depression to modulate a deep brain structure, the subgenual cingulate cortex. The engagement of the target using fMRI BOLD was validated. Moreover, the modulation of the target improved the patient's mood states. The effects were specific to the stimulated target and were not observed during sham stimulation, which delivered into the brain stimuli of same pressure and waveforms but in an unfocused manner.

Figure 16:
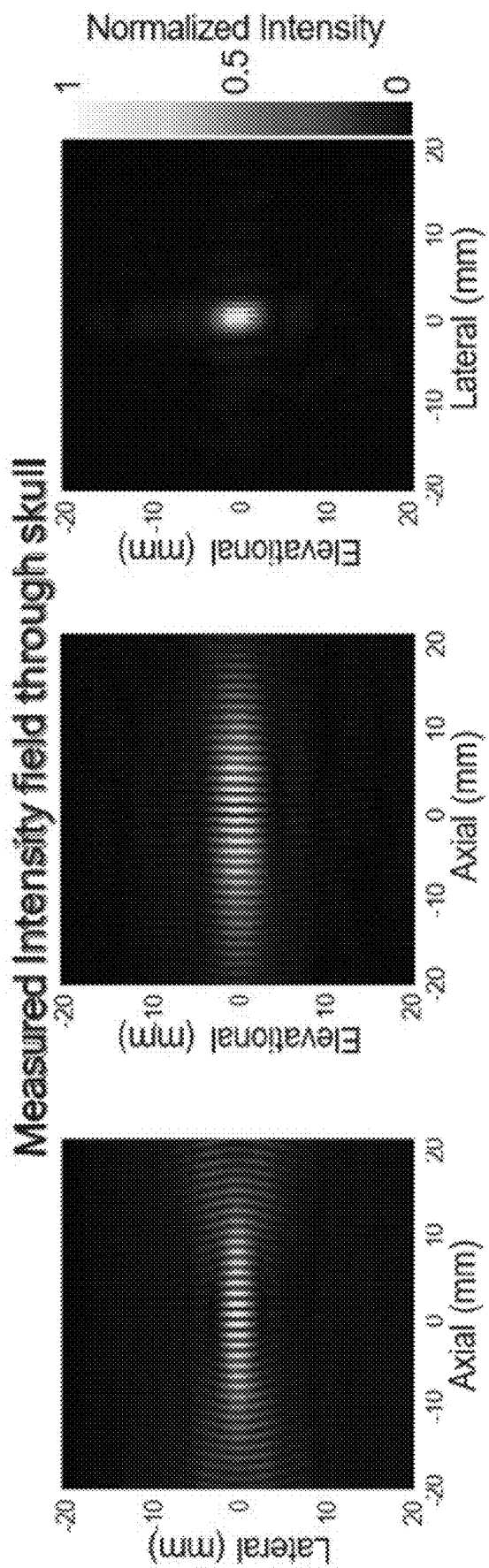
FIG. 16 illustrates that the head worn transducer array device produces spatially focused intensity field through skull. Intensity fields of the device's focus measured through an ex-vivo human skull.

The head-worn device 301 shown in FIG. 5B was applied to the patient (see FIG. 15). The device included two sets of 126 element phased array transducers positioned at opposite sides of the patient's head. The transmit receive capability of each transducer array element enables ultrasound-based correction for the attenuation (and dephasing) of each ultrasonic beam. A single pre-op MRI and mechanical registration was used to guide the transcranial application of focused ultrasound to multiple areas of the brain in the patient. When focusing at the target of subgenual cingulate cortex, the arrays produce an intensity field (see FIG. 16) with focal dimensions 20.4 mm axial, 2.4 mm lateral, and 3.6 mm elevational for a total volume of 142.71 $mm^3$, the equivalent volume of a sphere with diameter 6.48 mm.

Figure 17A:
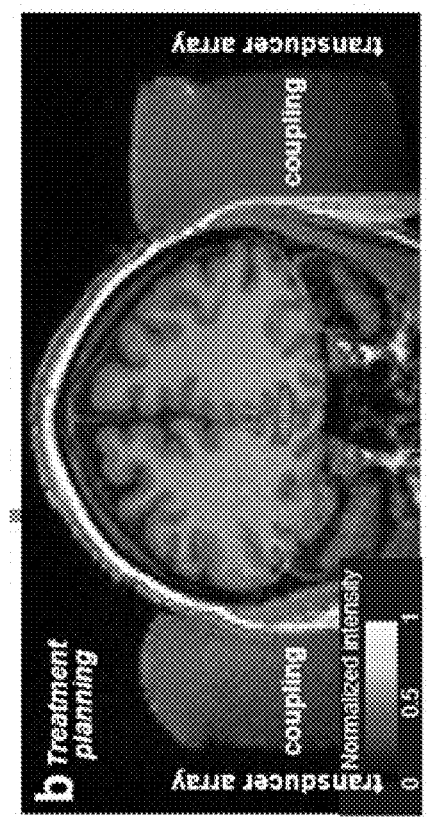
FIGS. 17A and 17B illustrate intensity fields produced by the transducer arrays overlaid on the subject's brain anatomy for scale.
Figure 17B:
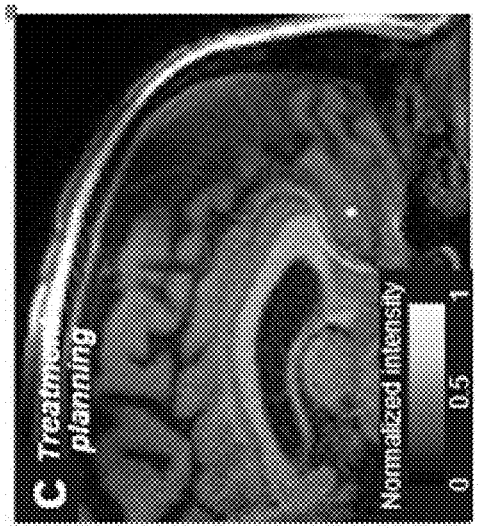
Figure 23:
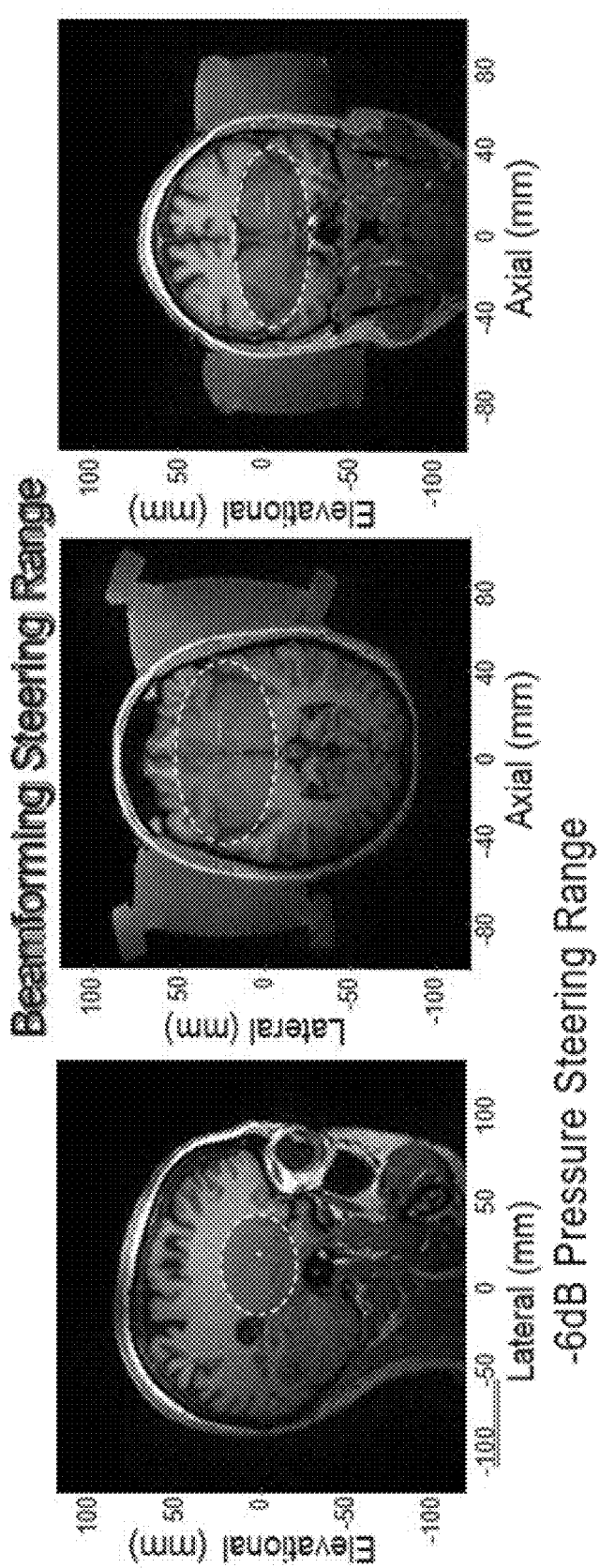
FIG. 23 are images where the blue region indicates the electronic steering range available to the head worn transducer array device. The device's focus through an ex-vivo human skull is overlaid onto the MRI image for scale. The focus can be beamformed to any location within this region in microseconds without physical motion of the device.

FIGS. 17A-B show the intensity fields produced by the arrays overlaid on the subject's brain anatomy for scale. The phased array geometry allows for flexible, electronic steering of the focus by ±45 mm, ±25 mm, and ±15 mm in the axial, lateral, and elevational dimensions, respectively (FIG. 23). The MRI compatible, plastic frame (shown in FIG. 15) holds the arrays and slides on horizontal and vertical tracks; allowing the arrays to be translated and then locked into position anywhere over the sides of the subject's head.

Figure 17C:
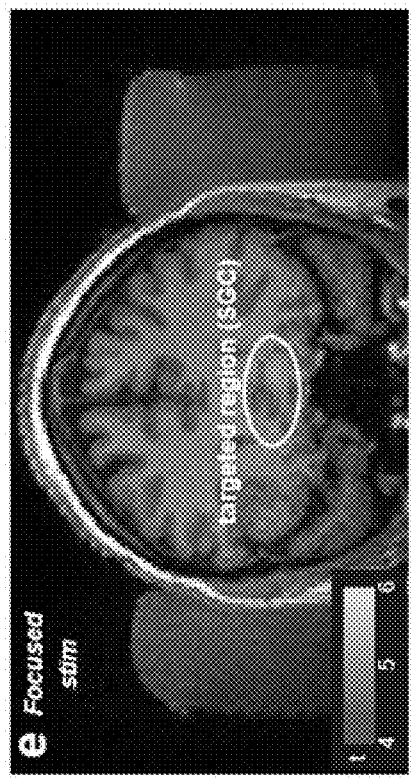
FIGS. 17C and 17D illustrate stimulation produced fMRI BOLD response at a targeted region.
Figure 17E:
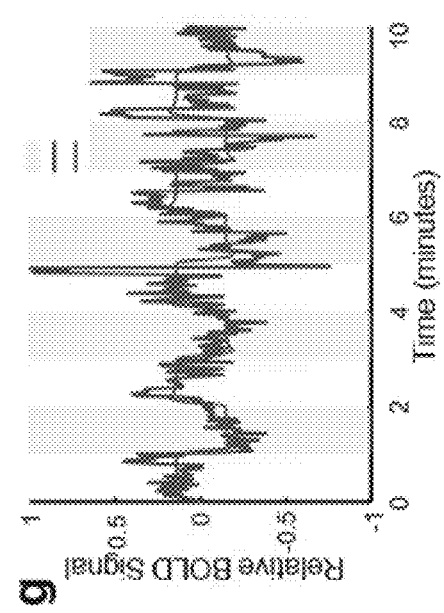
FIG. 17E illustrates fMRI BOLD response at target was time-locked to stimulation onset.
Figure 17D:
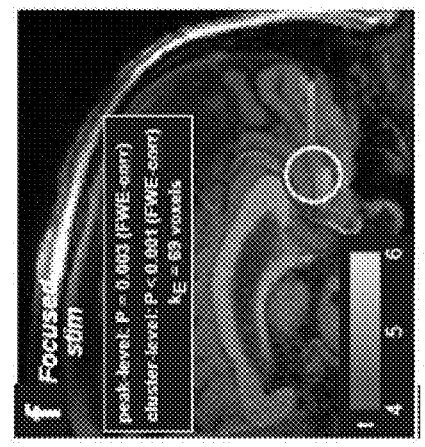
Figure 17F:
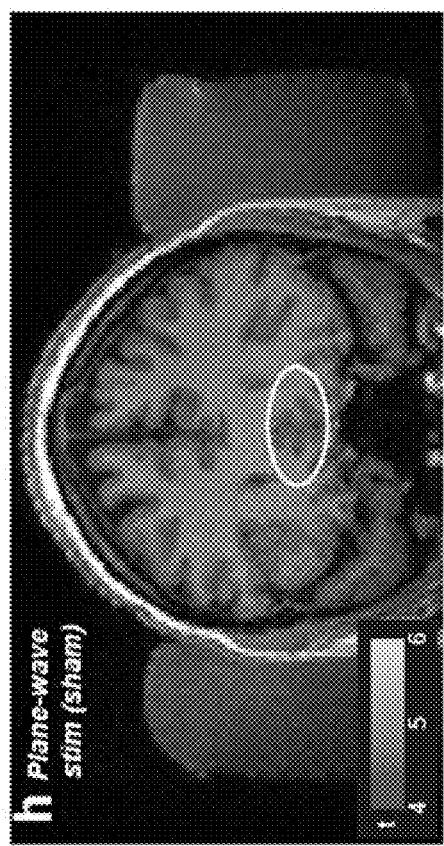
FIGS. 17F and 17G illustrate active sham stimulation with same stimulation parameters but arrays focused outside the subject head (plane wave) did not elicit BOLD response at target.
Figure 17G:
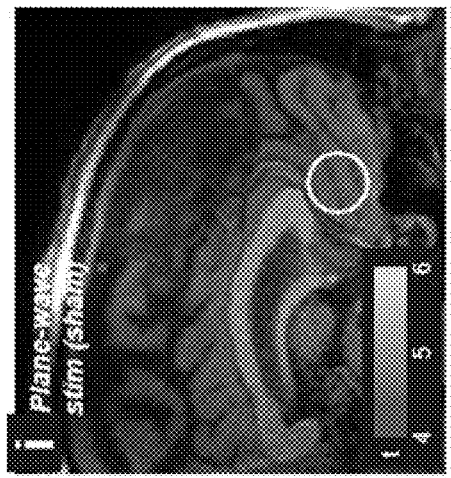

Following registration and ultrasound-based correction for the skull, the subgenual cingulate cortex of the brain was sonicated while measuring fMRI BOLD response FIGS. 17C-G. FIGS. 17C and 17D show significant bold activation at the targeted region (peak level: p=0.003, t=5.52, ZE=5.37, cluster-level p<0.001 (Family weighted error corrected, kE=69 voxels)). This fMRI BOLD activity was specific to the onset of the ultrasound stimulus (FIG. 17E). The contrast estimate of BOLD activity in this region from ultrasound off to ultrasound on conditions show a large effect size of 3.07±0.56 (mean±s.e.m.). The subject, blind to stimulus type, was also presented with active sham stimulation of unfocused, plane wave ultrasound as a negative control. The unfocused beam included the same stimulation parameters and intensity, but with phase delays adjusted to focus the energy far outside the subject's head. Under this active sham condition no significant BOLD activity was measured near the target (FIGS. 17F-G).

Figure 18:
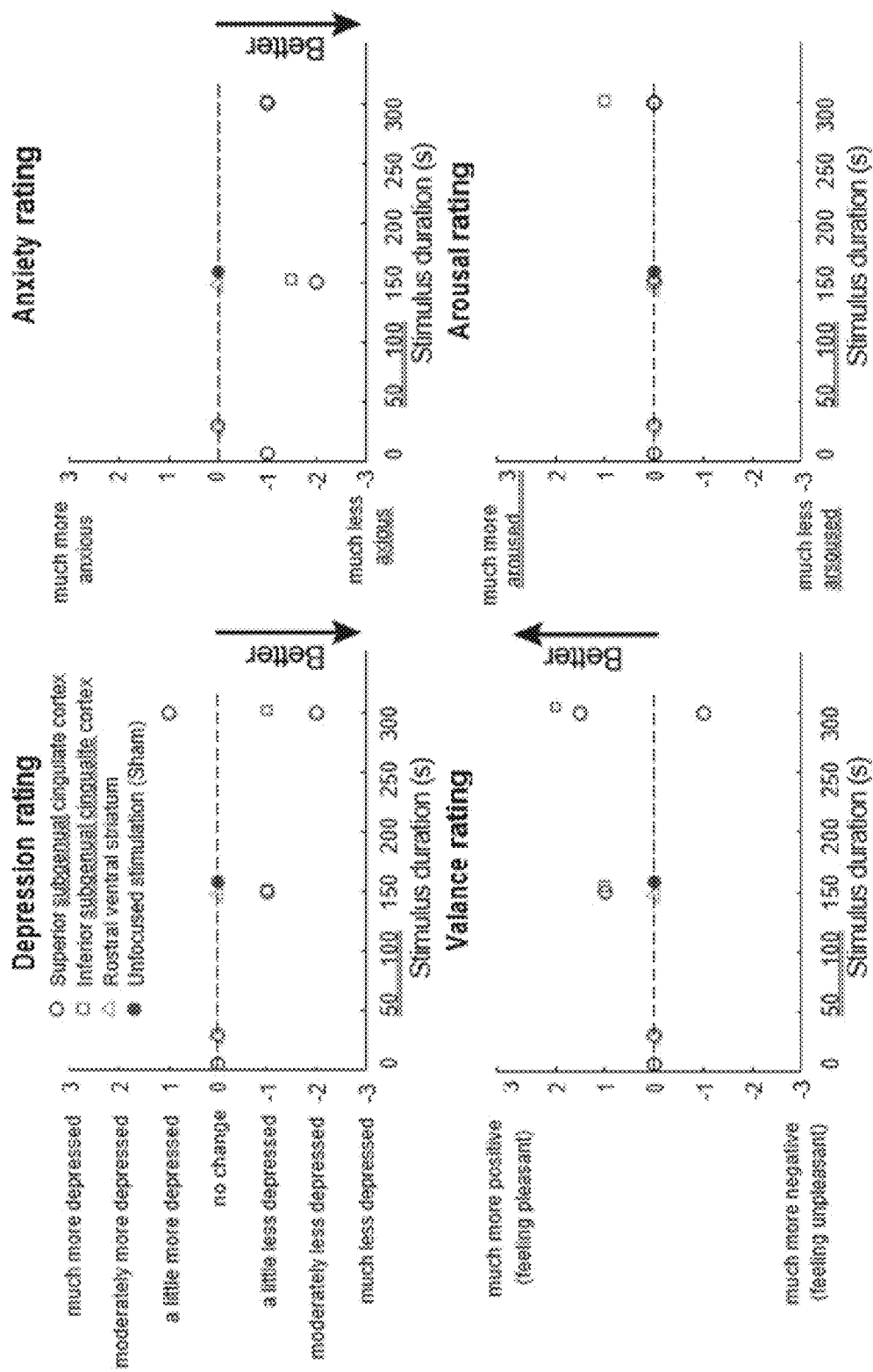
FIG. 18 illustrates in chart form that stimulation improves mood states in a depressed patient. Self-reported mood scores following each stimulation show decreases to anxiety and depression as well as increased feelings of pleasantness. Sham stimulation did not elicit any changes to the subject's mood ratings.
Figure 19:
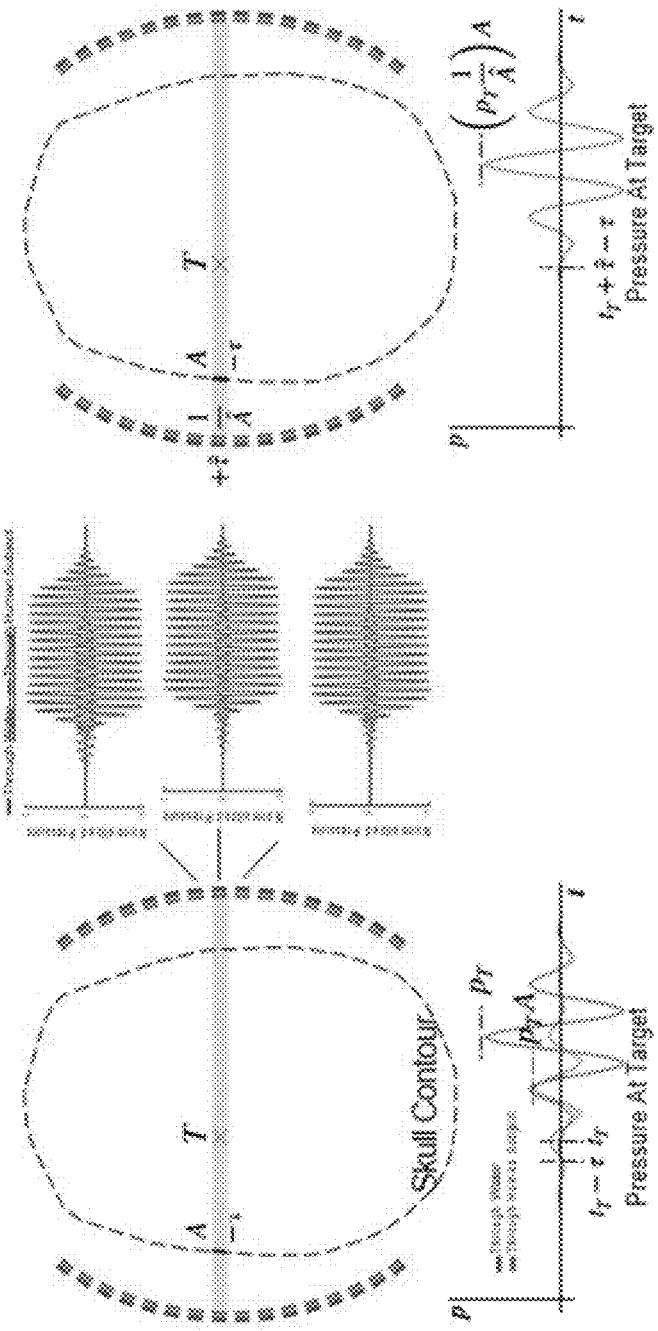
FIG. 19 illustrates an example correction method. The method uses through transmit measurements from all pairs of elements to solve for the attenuation and speedup encountered in front of each element, then adjusts stimulation parameters to correct for these distortions.

Outside the MRI scanner, the subject with 10 sonications of varying stimulation duration and focus location at a pressure of 1 MPa, pulse duration of 30 ms on, and pulse interval of 4 seconds was presented. Improvements in the subject's self-reported depression, anxiety and valance ratings when sonicating subgenual cingulate for durations of 150 and 300 seconds (FIG. 18) were observed. The subject did not report changes in mood when sonicating rostral ventral striatum or sonicating with the unfocused, plane wave stimulation of the same intensity. The effects were also specific to stimulus duration: changes in mood scores increased with increased stimulus duration. Stimulations with duration less than 150 s produced almost no changes in mood scores. Outside of these effects on mood, the subject reported subjective experiences of being able to hold a longer train of thought while under stimulation and feeling hopeful about events in the future for the first time in two weeks. Importantly, the subject reported no adverse effects across three ninety-minute-long sonication sessions (Table 1).

TABLE 1

| Adverse Effects Related To Treatment | Session 1 | Session 2 | Session 3 | Adverse Effects Related To Treatment | Session 1 | Session 2 | Session 3 |
| --- | --- | --- | --- | --- | --- | --- | --- |
| Headache | No | No | No | Skin rash or itching | No | No | No |
| Dry mouth | No | No | No | Tendency to develop bruises | No | No | No |
| Dizziness | No | No | No | Fever, increased temperature | No | No | No |
| Chest pain | No | No | No | Abnormal sweating | No | No | No |
| Palpitations | No | No | No | Hot flashes | No | No | No |
| Breathing problems | No | No | No | Convulsions or seizures | No | No | No |
| Circulation problems | No | No | No | Fatigue, loss of energy | No | No | No |
| Abdominal pain | No | No | No | Tremor | No | No | No |

TABLE 1-continued

| Adverse Effects Related To Treatment | Session 1 | Session 2 | Session 3 | Adverse Effects Related To Treatment | Session 1 | Session 2 | Session 3 |
|---|---|---|---|---|---|---|---|
| Nausea | No | No | No | Insomnia, sleeping problems | No | No | No |
| Vomiting | No | No | No | Back pain | No | No | No |
| Constipation | No | No | No | Muscle pain | No | No | No |
| Diarrhea | No | No | No | Joint pain | No | No | No |
| Reduced appetite | No | No | No | Agitation | No | No | No |
| Increased appetite | No | No | No | Irritability, nervousness | No | No | No |
| Difficulty urinating | No | No | No | Depressed mood | No | No | No |
| Sexual problems | No | No | No | Thoughts about suicide | No | No | No |
| Painful or irregular menstruation | No | No | No | Anxiety, fearfulness | No | No | No |

Figure 20:
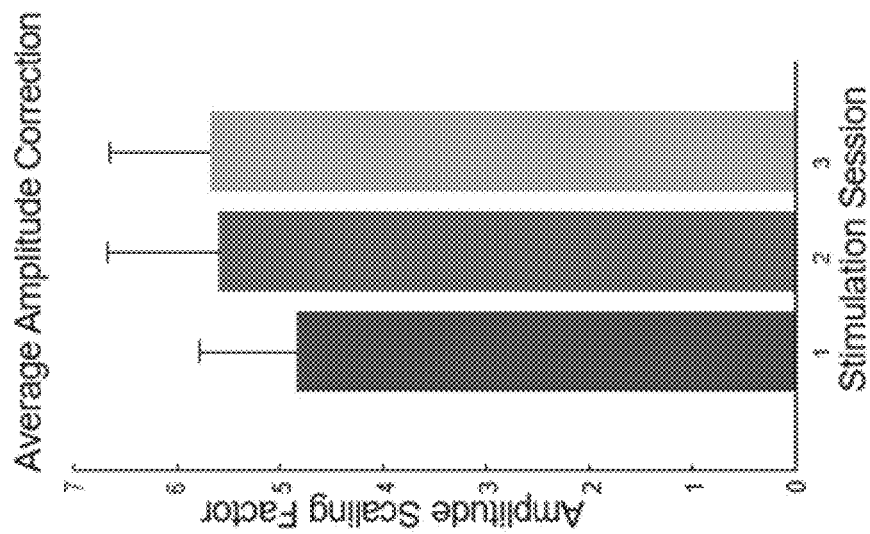
FIG. 20 is a chart illustrating average attenuation correction across sessions. Variability was observed between sessions due to quality of acoustic coupling between the transducers and subject's head. Elements that were not properly coupled (had an average pressure transmission <12%) were turned off.

Before sonicating a particular target, through transmit measurements on the subject were acquired, attenuation and phase delay were estimated in front of each element compared to water, and stimulation parameters were adjusted to correct for these ultrasound aberrations. FIGS. 5A-C, 6, 7, 8A-B, and 19 show the steps involved in the correction and example through transmit waveforms taken through water and through the subject. The entire through transmit scan across all 252 elements takes less than one second to capture. Critically, the scans measure attenuation from all sources on the beam path: coupling, hair, local air pockets, skull, and brain. The immediate measurement of pressure transmission through the skull on each element informed operators of the acoustic coupling quality, and allowed them fix uncoupled elements before sonicating. FIG. 20 shows the average amplitude scaling factor applied to the transducer elements to compensate for the estimated attenuation. The average amplitude scaling factor was 4.84±0.94 (mean±S.D.) for stimulation session 1, 5.59±1.09 for session 2, and 5.68±0.97 session 3. Any element that had an estimated pressure transmission less than 12% was turned off and the remaining elements increased their amplitude to compensate for that element's lost contribution.

Figure 21:
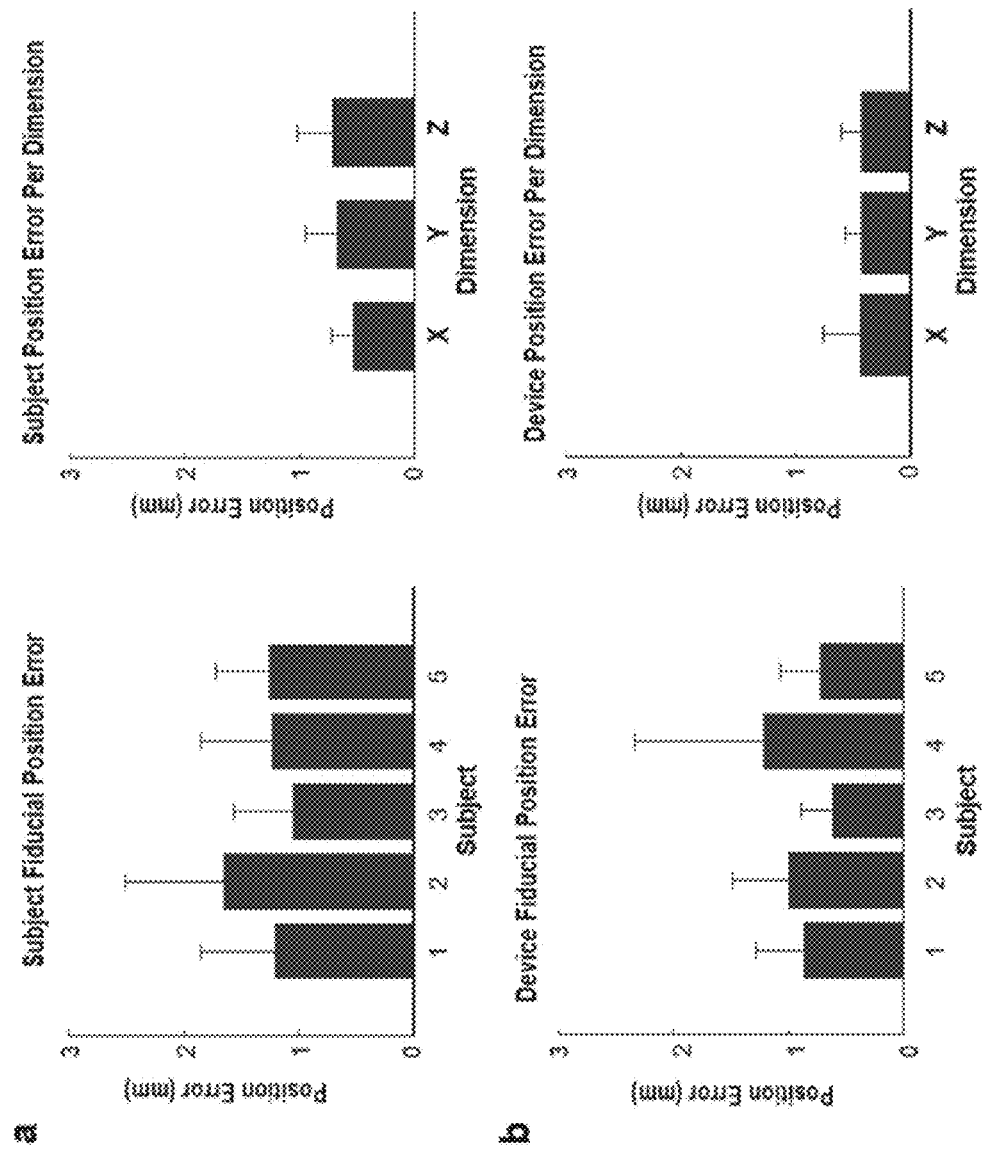
FIG. 21 are charts indicating that mechanical registration provides reproducible targeting across sessions. a. Deviation between location of ultrasound focus and brain target across five human subjects. b. Targeting error delineated by spatial dimension.
Figure 22:
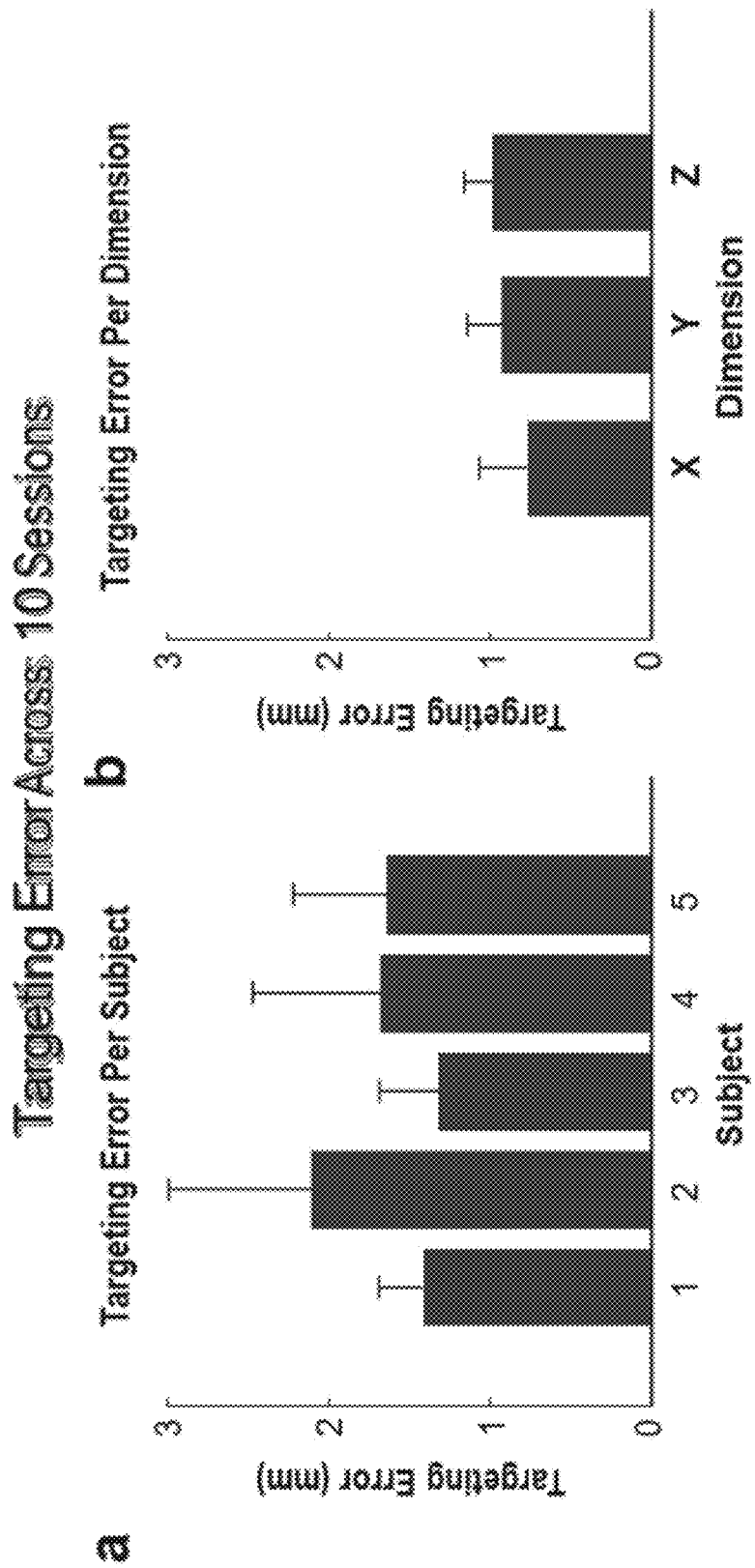
FIG. 22 are charts indicating that mechanical registration provides reproducible targeting across sessions. a. Deviation between location of ultrasound focus and brain target across five human subjects. b. Targeting error delineated by spatial dimension.

Finally, to assess targeting reproducibility, the device's targeting error was measured across multiple sessions and subjects. The plastic frame allowed for repeatable positioning of the ultrasound transducers. Across all sessions and subjects, the ultrasound transducer position varied by 0.89±0.64 (mean±S.D.) total and 0.45±0.32, 0.43±0.14, and 0.44±0.17 in the x, y, and z dimensions. The thermoplastic mask reliably fixed the subject's head in the same position across sessions. Fiducial markers on the subject varied in position by an average of 1.28±0.66 total and 0.53±0.19, 0.68±0.27, and 0.71±0.31 in the x, y, and z dimensions across all subjects and trials (FIG. 21). Targeting error—the deviation between the location of a hypothetical ultrasound focus and a brain target of interest—was assessed by measuring the average difference in position between fiducials on the subject and fiducials on the ultrasound transducer. In total, the device had an average targeting error of 1.64±0.66 across subjects and 0.77±0.50, 0.93±0.41, 0.99±0.49 across the x, y, and z dimensions, respectively (FIG. 22).

Figure 33:
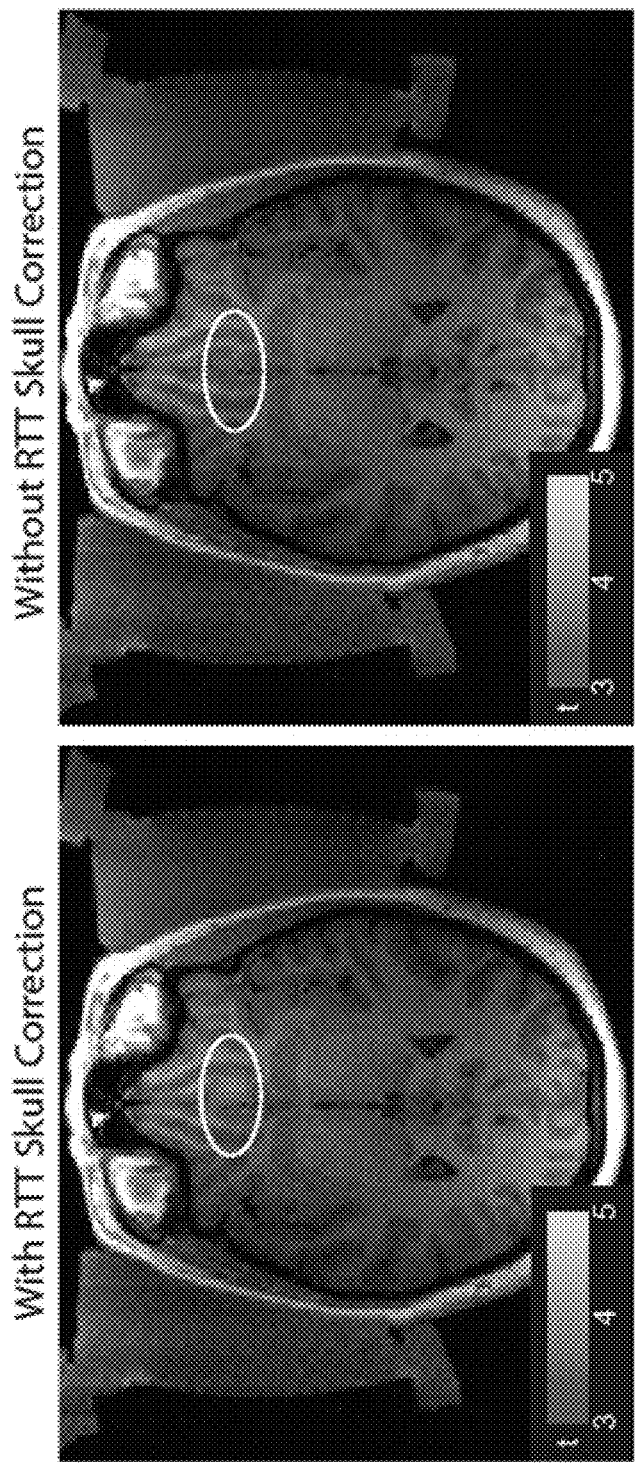
FIG. 33 shows that the compensation for the ultrasound attenuation by the head is critical for effective neuromodulation. The figure shows the statistical significance of fMRI BOLD signals modulation by ultrasound at a deep brain target when the correction is applied (left) and not applied (right).

This study described in this example validated the effectiveness of the device by eliciting significant changes in fMRI BOLD activity at the targeted area. The device improves on current ultrasound neuromodulation technologies by correcting for attenuation and phase shifts caused by the subject's skull, hair, and acoustic coupling; thereby delivering effective and safe intensity at target. FIG. 33, (at left), demonstrates that this function is critical for effective ultrasonic neuromodulation. When not applied (FIG. 33, right), which has been the case with existing ultrasonic devices, there is no neuromodulation effect.

The mechanical frame and phased array system can flexibly focus energy into spatially specific targets throughout the deep brain. Using a novel mechanical registration approach, the device enables reproducible targeting of deep brain areas across subjects and treatment sessions outside the MRI scanner without the need for expensive neuronavigation systems.

This device provides effective neuromodulation in humans that can be monitored via fMRI BOLD measurements. Clear fMRI bold response at target was elicited when stimulating subgenual cingulate cortex in a human subject. Changes in fMRI BOLD activity were time locked to the ultrasound stimulus and absent during sham stimulation. Together, these data provide strong evidence that the device focally activates deep brain targets and the response is specific to ultrasound stimulation. The fMRI BOLD readout available to this MM compatible device gives valuable feedback on neuromodulation amplitude, polarity, and targeting accuracy. With the stimulation parameters in the MRI scanner, it was discovered that the stimulation was on target and inhibited activity in the subgenual cingulate cortex.

The modulation of subgenual cingulate cortex effectively induced positive changes in the subject's mood states. Specifically, improvements to subject's self-reported scores of depression, anxiety and valence were observed. The subject did not report changes in mood in response to sham stimulation, stimulation of rostrial ventral striatum, or majority of stimulations with duration less than one minute. Overall, the changes in mood were specific to both targeted area (subgenual cingulate) and stimulation parameters (duration greater than one minute). Stimulation from the device was safe and well tolerated. The subject reported no adverse effects across three ninety-minute sessions of stimulation.

The device's ability to measure attenuation of the ultrasound beam is important for both safety and effectiveness (FIG. 33). Ultrasound attenuation varied across sessions. Due to the repeatable positioning of the device over the same section of the skull, these differences are likely due to variability in coupling of the transducers with the subject's head. A safety feature of the device was to turn off elements that experience especially high attenuation—which could be a result of local air pockets or particularly thick areas of skull. In either case sonication could result in dangerous cavitation or heating effects. Regarding effectiveness, the substantial amplitude scaling factors applied to the array elements as well as phase correction was critical for stimulation. When titrating the dose, several sonications were delivered at 0.4 MPa of delivered pressure through the skull and saw no changes in mood scores. Given the average pressure amplitude scaling factor for this particular subject of 5.37, if correction for the skull did not occur, less than 1.09 W/cm$^2$ (0.18 MPa) would have been delivered when the intended intensity was 33.78 W/cm$^2$ (1 MPa). CT corrections for the skull, which are effective for measuring skull induced dephasing but not attenuation cannot account for attenuation due to hair, entrapped bubbles, and variability in acoustic coupling. These additional barriers are substantial, attenuating the transmitted intensity by ~0-64% due to coupling by ~20% due to hair and by up to 100% due to a local bubble or air pocket. For instance, in some sessions it was discovered that as many as 60 of the 252 elements were not acoustically coupled to the subject before sonicating, and this coupling issue had to be corrected before sonicating. The remaining uncoupled elements were turned off. This feedback is absent with CT corrections and would have lead to potentially dangerous sonication of local air pockets and less than effective pressure at target.

The flexible and reproducible targeting of the device allows for interventions into numerous areas across the brain (FIG. 23). To engage the subgenual cingulate in this subject, the beam was steered electronically 17 mm laterally and 9 mm elevationally from the geometric center of the arrays. With the arrays locked in place and using electronic beamforming, the superior and inferior sections of the subgenual cingulate cortex, ventral striatum, were sonicated, and steered the beam outside the head for sham stimulation all in the same stimulation session. With the ability to beamform to different targets in microseconds, hundreds of unique brain areas can be stimulated per minute by the phased array system. Other areas of the brain—such as thalamic nuclei, the amygdala, the cingulate cortex, the insular cortex, nucleus accumbens, ventral tegmental area, etc. —can be addressed through a combination of physical movement of the arrays and beamforming the focus to a given target. This fast, flexible targeting is unique to phased array systems. Devices for neuromodulation have typically used single element transducers that are MM guided or use optical neuro-navigation for targeting. The mechanical registration method allows for accurate targeting of deep brain areas inside and outside of an MRI scanner and without the need for these more costly registration tools.

While robust fMRI BOLD activity in response to stimulation has been shown in animal studies, only two groups have reported fMRI measurements in humans. These results are extended by showing a first demonstration of fMRI BOLD response to ultrasonic stimulation of subgenual cingulate, a comparatively deep area, as well as a relatively strong effect size. The strong fMRI activation is due to increased pressure at target gained from correcting for skull aberrations (FIG. 33). Overall, these significant, time locked BOLD responses to ultrasound stimulation demonstrate a critical feature of the device to monitor neuromodulation effect size, polarity, and targeting accuracy.

This study also demonstrates for the first time tFUS stimulation of subgenual cingulate cortex improves mood states in a treatment resistant depression patient. Previous studies have similarly shown improvements to mood with FUS stimulation of ventro-lateral prefrontal cortex and inferior frontal gyrus. Immediate improvements in mood were observed as well as subjective effects such as hopefulness for future events. The rationale for targeting subgenual cingulate is derived from previous DBS studies and neuroscientific literature showing this area implicated in major depressive disorder. Results of this study support the notion that SGC regulates mood states and is a promising target for longer duration FUS stimulation.

The fMRI and mood response results of this study were limited to a single subject of an ongoing clinical trial with 20 subjects total. However, the fMRI results were statistically significant from baseline and the mood effects reproducible across sessions and robust to sham; thus these data demonstrate proof of concept in the first human subject of this trial. Stimulation targets in this first subject were limited to ventral striatum and subgenual cingulate cortex. Due to the fast and flexible beamforming of ultrasound, the medial forebrain bundle, ventral tegmental area, and multiple targets within anterior cingulate cortex, which are unique brain targets, can be sonicated nearly simultaneously in rapid sequence. The device is limited to sonicating through areas of the skull in which a through transmit path can be established; namely the left and right sides of the head. Thus, while the device has access to nearly the entire subcortical volume of the brain through mechanical translation of the arrays and phased array steering, it has limited access to cortical brain targets.

A non-invasive device capable of controlled delivery of ultrasound for safe and effective deep brain stimulation has been described herein. The pairing of ultrasound stimulation with fMRI enables straightforward monitoring of neuromodulation. Regarding practicality, a single T1 MRI of the patient's head inside the device is needed for accurate targeting in all subsequent applications of the ultrasound. Additionally, no shaving of the head is required. The phased array system can adjust the stimulation location within the brain in microseconds with millimeter accuracy and stimulate hundreds of unique brain targets per minute. Compared with existing FUS brain stimulation (e.g., BXPulsar, NeuroFUS®) or surgical (e.g., EXABLATE® Neuro) devices, this is the only device with the capability to compensate for the attenuation of the human skull, hair, and variable acoustic coupling. This ability is critical, as each barrier distorts and attenuates ultrasound severely and unpredictably. Any future low-intensity application of ultrasound to the brain must address this issue so that the ultrasonic intensity delivered into a target is safe, effective, and reproducible from patient to patient. The device's accurate correction for these distortions is expected to greatly improve safety and efficacy of not just neuromodulation but other low-intensity applications of transcranial focused ultrasound such as local drug delivery and blood-brain barrier opening, which, like ultrasound neuromodulation, are highly dependent on the delivered ultrasound intensity.

Example 2: Testing Accuracy and Effectiveness of RTT

Figure 24:
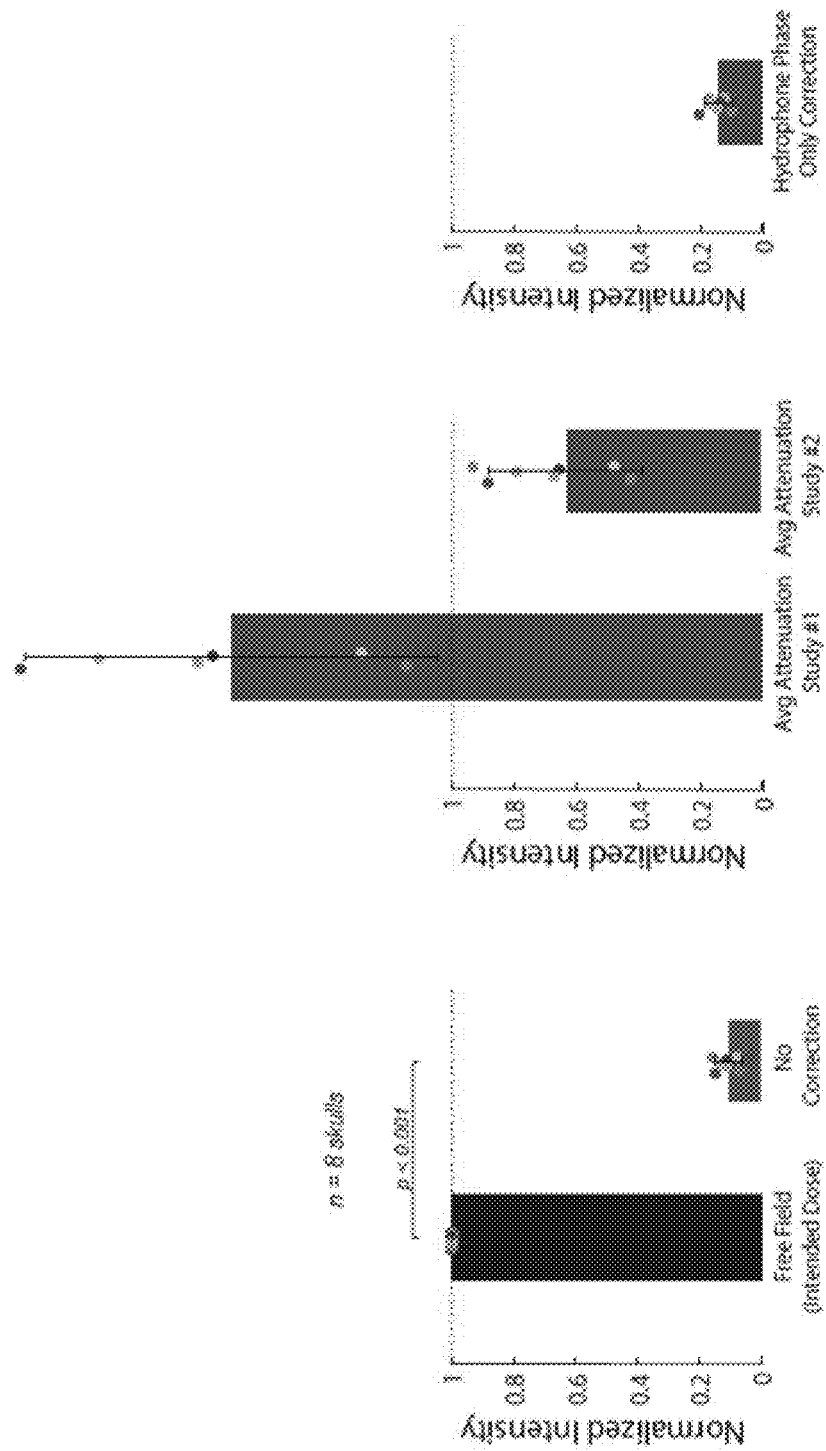
FIG. 24 illustrates ultrasound attenuation of the human skull.

FIG. 24A demonstrates the severity of acoustic attenuation by the skull. Across 8 ex-vivo skulls, it was discovered that the ultrasound intensity delivered into a deep brain location is attenuated by a factor of 11.4±6.8 (mean±S.D.), which replicates previous findings. In principle, the attenuation could be estimated using tabulated values (e.g., 20, 21), but the high variability of the attenuation across individuals makes such estimates inaccurate and uncertain (FIG. 24B). For example, using the values of those two studies would over- and under-estimate the average value by a factor of 1.7±0.67 and 0.63±0.25, respectively, and lead to high variability (pooled standard deviation equal to 0.47, compared to the normalized intensity of 1.0). A compensation for the dephasing of the ultrasound, which can be obtained using existing methods is useful for ultrasound-based surgeries and to an extent also for the present purpose of delivering deterministic intensity into specified targets for repeated applications (FIG. 24C). Nonetheless, even the hypothetically ideal correction for the phase based on ground-truth measurements (FIG. 24C) leaves an average discrepancy of 85% between the intended and actual intensities delivered into a brain target.

The system of FIG. 1A and device illustrated in FIG. 5A was utilized to test the accuracy of RTT described above, when ultrasound was focused into specific targets inside human ex-vivo skulls. The induced fields using a hydrophone were measured. The measured intensities in four conditions were assessed. First, the intensities in free-field were measured, which presents no obstacles for ultrasound. This intensity corresponds to the intensity intended to be delivered into the target by the operator. Second, skulls were positioned between the device and the hydrophone, and the resulting intensities were measured. This case presented the worst-case scenario of no correction for the skull. Third, the hypothetical ideal correction for the skull was evaluated. To do that, the hydrophone was used to measure the attenuation and dephasing for each element of the device, thus obtaining ground-truth values. These ground-truth values were used to compensate for these aberrations, scaling the magnitude of the emitted ultrasound from each element and delaying it accordingly, as if no skull was present. And fourth, the RTT correction was applied.

Figure 25:
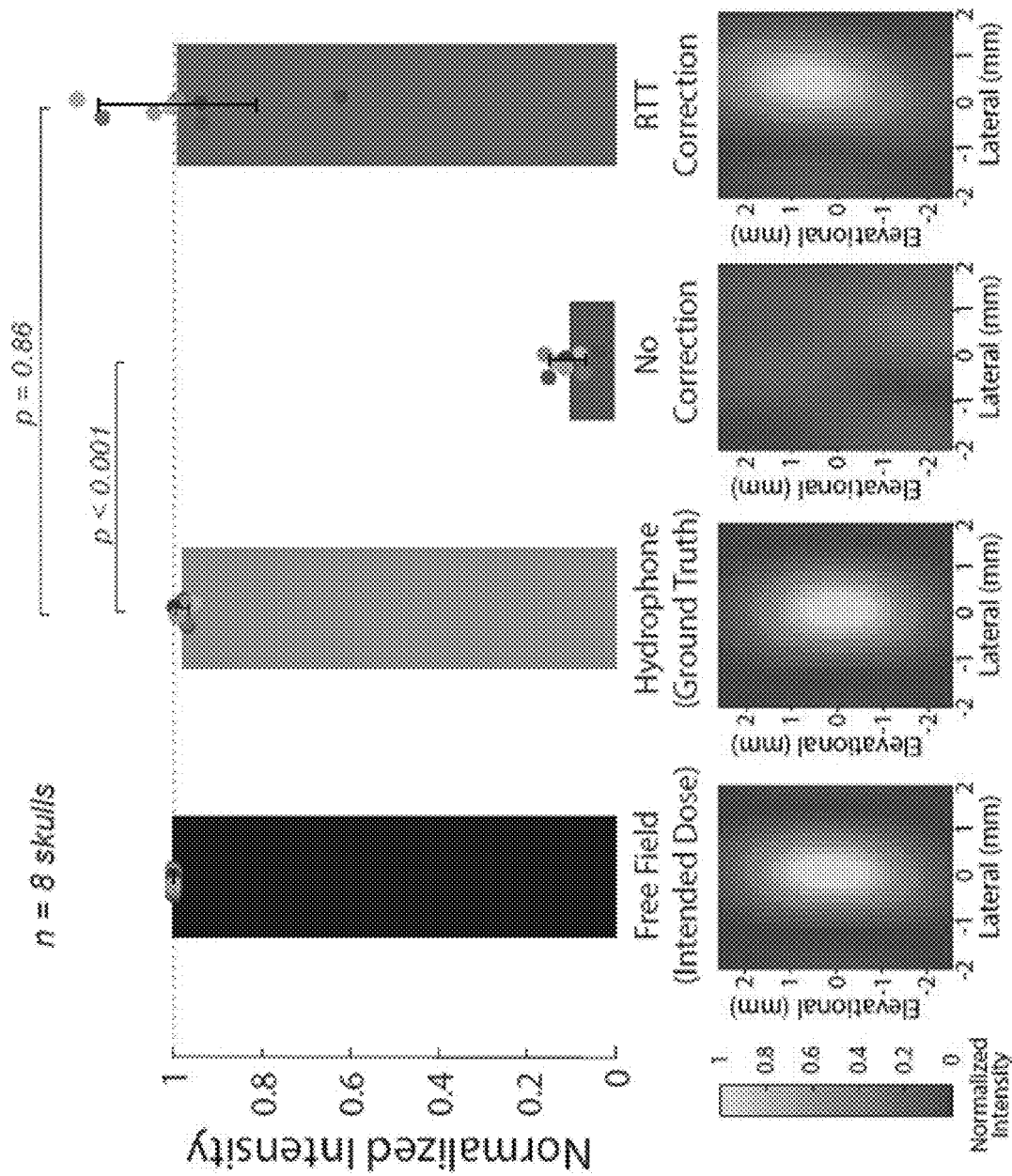
FIG. 25 illustrates that RTT accurately compensates for each skull and restores the intended intensity at target. Ultrasound fields obtained inside ex-vivo human skulls (n=8), separately for the hypothetical ideal correction (gray), no correction (red), and RTT (green). The top bars show the spatial peak intensities of the field for each case. The bottom plots provide the corresponding spatial distribution of the ultrasonic fields with respect to the target.

These measurements were performed inside 8 water-immersed, degassed human ex-vivo skulls. FIG. 25 shows the spatial peak intensity and the associated field for a target positioned at the center of the two transducers. The figure reinforces the notion that human skulls severely dampen the intensity delivered into the brain (red). Compared with the free-field values, the ultrasound intensity through the skull was attenuated by a factor of 11.4±6.8 (mean±S.D.), degrading it to 10.7±4.2% of the intended intensity. The difference between the free-field and through-skull values was significant ($t7=60.7$, $p=8.6\times10^{-11}$, paired two-tailed t-test).

RTT using the phased arrays was next applied. FIG. 25 shows that RTT restores the intended intensity values (green). The RTT-compensated intensity constituted 98.8±17.8% (mean±S.D.) of the intended values in free-field, and there was no significant difference between the mean of two conditions ($t7=0.18$, $p=0.86$, paired two-tailed t-test). The average value was also not significantly different than the hypothetical, best-possible correction based on the hydrophone ground-truth measurements inside the skull (black bar; $t7=0.17$, $p=0.86$, paired two-tailed t-test). One skull (purple datapoint) attenuated the ultrasound severely (a factor of 26.9 attenuation). This was likely due to visually present outgrowths possibly related to hyperostosis, as assessed by a neurosurgeon. For this skull, the RTT correction was less accurate, achieving a factor of 0.62 of the intended intensity.

Figure 26:
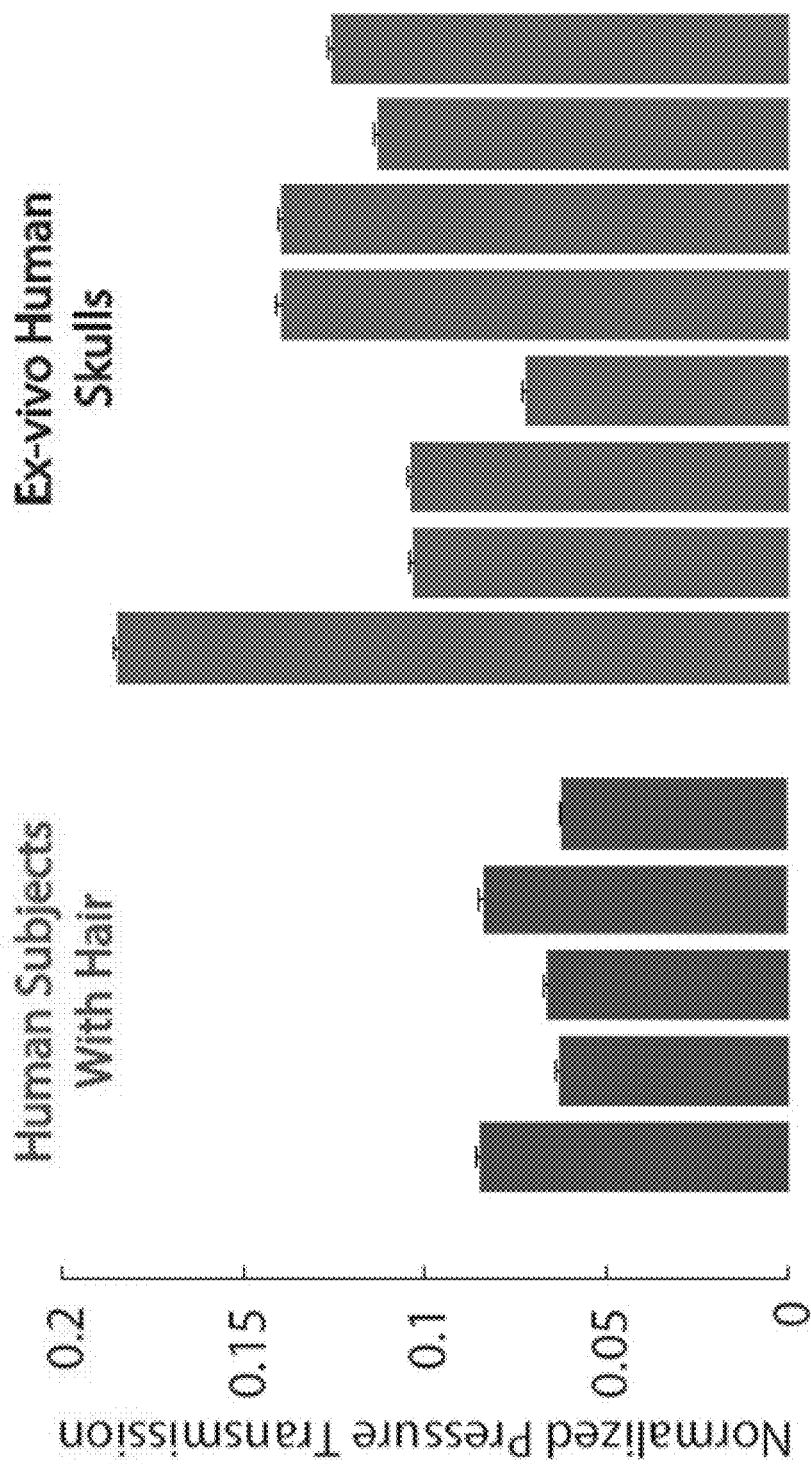
FIG. 26 illustrates the effects of RTT applied though the human head. Average through transmit attenuation value across all elements in 5 human subjects and 8 ex-vivo human skulls. No hair shaving was necessary to obtain robust through-transmit signals.

Next assessed was whether RTT could be applied to the human head, which presents additional key barriers for transcranial ultrasound including hair, scalp, acoustic coupling, and the brain. This test also evaluated the safety of the method. RTT was designed to be safe. The RTT scan consists of brief (<100 µs) low-intensity (average peak pressure of 80 kPa in free field) pulses of ultrasound. The RTT scan takes less than one second to complete. Subjects (n=5) did not feel any discomfort during the procedure. FIG. 26 blue shows the average through transmit attenuation through both sides of the head, separately for each subject. The figure demonstrates that the method offers through-transmit quality comparable to the ex-vivo skulls (gray). Specifically, the receiving elements on the opposite side of the head recorded an average of 7.3±4.8% (mean±SD, n=5 subjects) of the signal amplitude when RTT was applied through the human skull, and 12.6±8.2% for the characterized ex-vivo human skulls (mean±SD, n=8 skulls). The additional factor of 1.7 attenuation was expected because the application of ultrasound through the human head incurs additional attenuation by hair, scalp, coupling, bubbles or air pockets in between, as well as tissues inside the skull. No subject reported side effects at 1 week follow-up. Thus, RTT can be safely applied to the head of humans and directly measures the attenuation by all obstacles within the ultrasound path.

Figure 27:
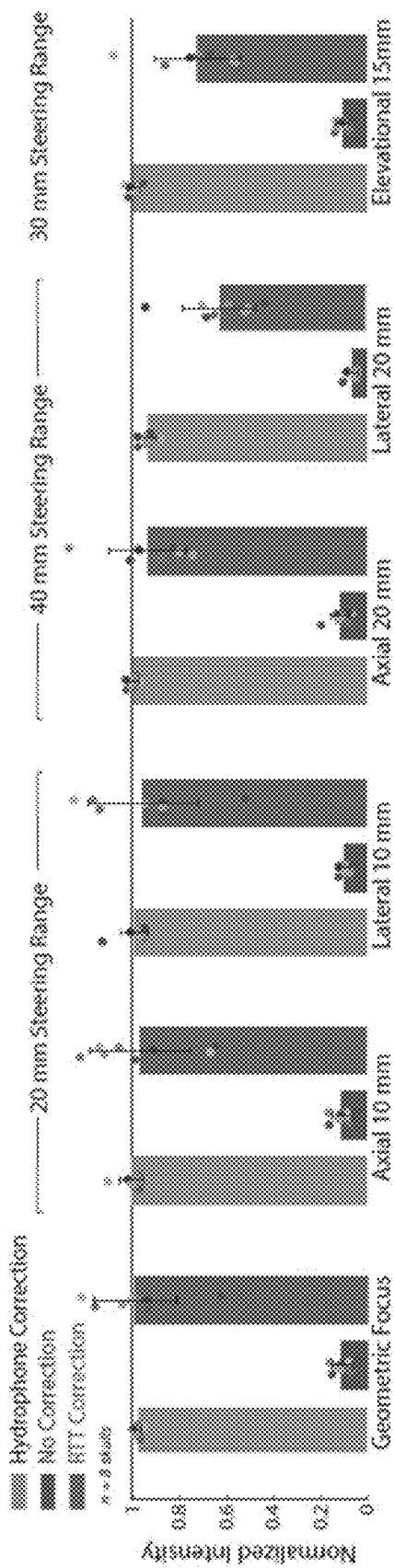
FIG. 27 illustrates RTT performance as a function of the range of action. Includes targets comprising the full steering range of the array: 10 mm axial, 20 mm axial, 10 mm lateral, 20 mm lateral, and 15 mm elevational to the central target. Axial refers to the line connecting the centers of the two transducers.

The robustness of RTT with respect to brain target location was next tested. To do so, the phased arrays were used to refocus the ultrasound into targets covering the full steering range of the device: 10 mm axial, 20 mm axial, 10 mm lateral, 20 mm lateral, and 15 mm elevational to the central target (FIG. 27). RTT correction brought the delivered intensity to 96.3±21.4%, 94.8±23.2%, 92.8±16.4%, 62.5±15.7%, and 71.6±18.03% of the intended value in each target respectively. There was no statistical difference between the mean of intended peak intensities and the RTT-compensated peak intensities at the central target ($t7=0.18$, $p=0.86$, paired two-tailed t-test), 10 mm axial ($t7=0.48$, $p=0.64$, paired two-tailed t-test), 10 mm lateral ($t7=0.42$, $p=0.55$, paired two-tailed t-test), and 20 mm axial ($t7=1.23$, $p=0.26$, paired two-tailed t-test). There was a significant difference in the average delivered intensity at the target 20 mm lateral ($t7=6.748$, $p=0.0002$, paired two-tailed t-test) and 15 mm elevational ($t7=4.5$, $p=0.003$, paired two-tailed t-test).

Figure 28:
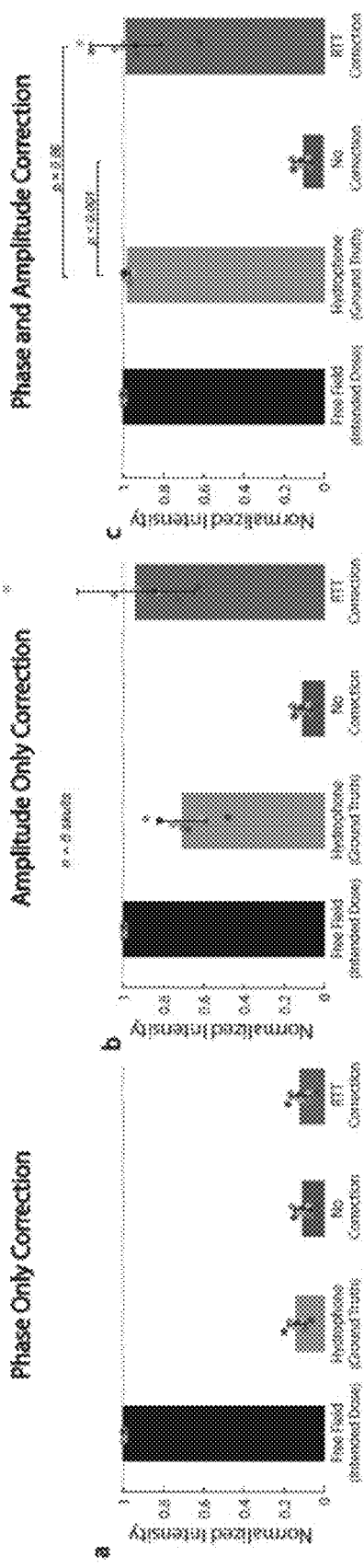
FIG. 28 illustrates that correction for phase is insufficient to account for the skull attenuation. Spatial peak intensity at the central target using the phase correction component (a), amplitude component (b) and both components (c) of RTT.

Subsequently, the relative contribution of the two key components of the ultrasound aberration by the skull—the attenuation and dephasing were tested. FIG. 28 shows the spatial peak intensity following the engagement of each correction type in isolation as well as their joint application. At the central target, phase-only correction resulted in average intensity of 13.8±4.3% (mean±S.D.) for the ideal hydrophone correction (gray) and 11.9±4.9% for RTT (green). The no correction value (red) was 10.7±4.2% of the free field intensity. The amplitude-only correction brought the peak spatial intensity to 71±12.5 for the hydrophone and 93.8±28.9 for RTT. Thus, the correction for the attenuation (i.e., for the amplitude of the received signals) constitutes the key factor in the delivered ultrasound intensity. The inclusion of the correction for the phase is additionally desirable in that the resulting joint correction (FIG. 28 (at c)) brings the average delivered intensity to 98.8±17.8%.

Figure 29:
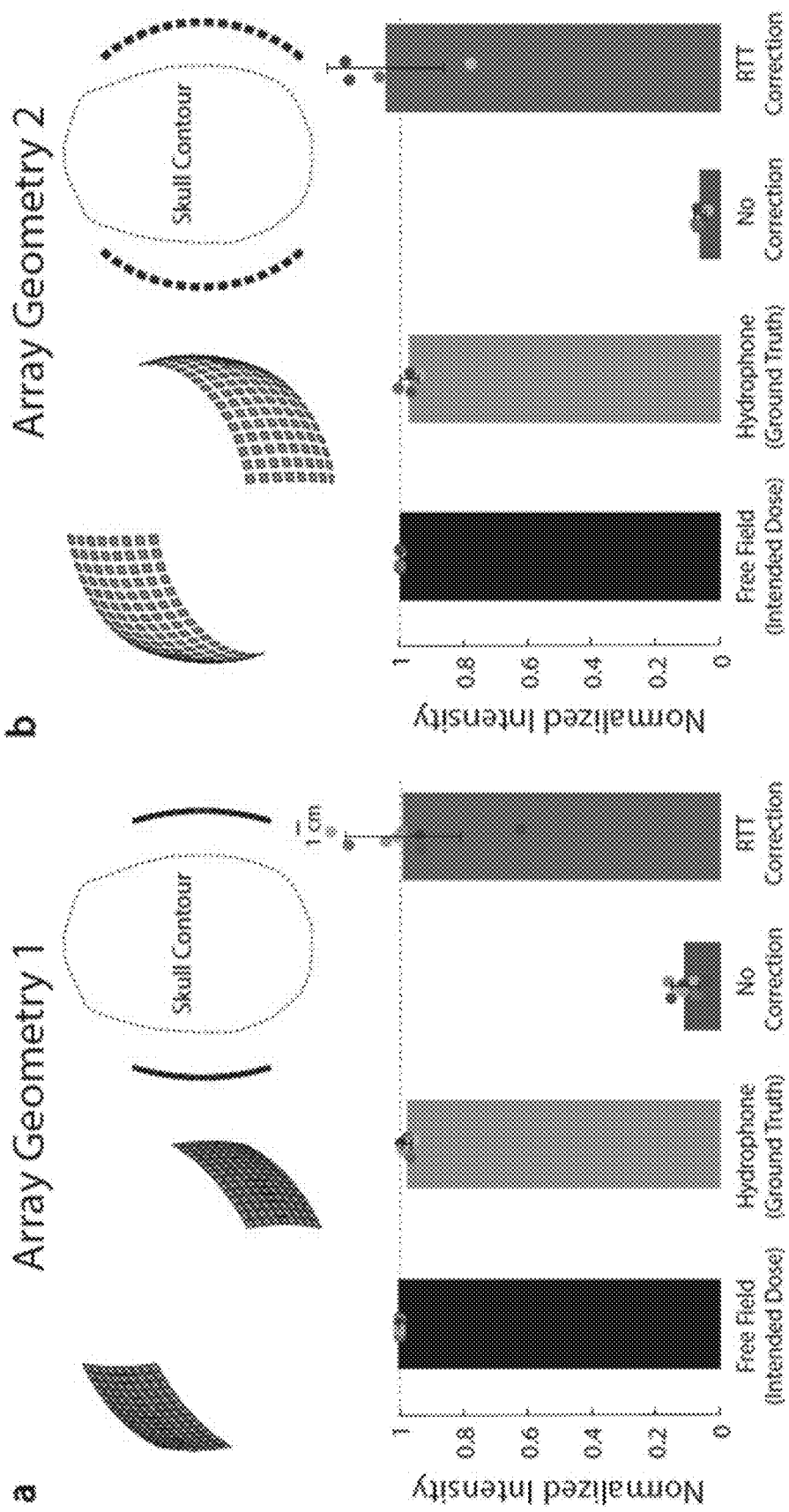
FIG. 29 illustrates that RTT is robust across distinct hardware. (a) Array geometry of the head-worn transducer array device. The associated correction values are the same data as in FIG. 25. The correction performed relatively poorly in subject 8 (purple marker), which had the thickest skull with bone outgrowths and possible hyperostosis. (b) Array geometry of the head-worn transducer array device with a larger aperture and the associated correction data.

The robustness of RTT with respect to specific hardware was further tested. In particular, RTT was implemented on arrays that had the same number of elements but much larger aperture (FIG. 29). For this configuration, skulls (n=4 specimens) degraded the intensity at the geometric center to 6.3±1.7% of the intended, free-field value, in line with FIG. 24.

The RTT compensation recovered the intensity at the target to 104±18.1% of the intended value. Following the compensation, there was no significant difference between the intended and mean RTT-recovered intensities ($t3=0.47$, $p=0.67$, paired two-tailed t-test).

Example 3: Demonstrating Effective Application of Transcranial Ultrasound for Neuromodulation Using Head-Worn Device in Humans To test effects on nerves within intact biological tissues, 11 human subjects were instructed to place their thumb into a holder at the central target inside an ev-vivo skull. The subjects' responsiveness to the ultrasound when RTT was applied and when it was absent (see Methods) was quantified. The target received a 300 ms stimulus of specific pressure levels, and the effects on the subjects' nociceptive responses was assessed. Nociceptive responses indicate stimulation of nerves or nerve endings in the tissue. It was discovered that RTT was critical for effective stimulation (FIG. 30 (at a)). Without RTT, there was no significant stimulation (red; t11=1.00, p=0.34, one-sample two-tailed t-test). Following RTT, the response rate of subjects to the stimuli reached 62.7%. This level was statistically equivalent (t10=0.58, p=0.57, paired two-tailed t-test) to a 66.3% response rate obtained with the hypothetical best-possible ground-truth correction, which is as good as if no skull was present. FIG. 31 shows individual responses to each correction of all subjects.

To control for potential confounds that could be associated with ultrasonic stimulation, a sham stimulus that delivered the ultrasound 10 mm below the target with hydrophone correction was randomly interleaved. This off-target stimulation produced no significant stimulation (yellow, p=0.19, one-sample two-tailed t-test, t11=1.39). This controls for a potential artifactual effect and confirms the spatial specificity of the stimulation.

The dose dependence of the stimulatory effects was further investigated.

Specifically, the stimulation across three intensity levels were varied. An increase in stimulation effectiveness with increasing level of the ultrasound (FIG. 30 (at b)) was discovered. The response frequency reached 62.7% for the strongest (1.8 MPa) stimulus, and was significant also for the weakest stimulus tested (1.3 MPa; t10=7.63, p=1.7×10-5, one-sample two-tailed t-test). The effect of the stimulation level was highly significant (two-way ANOVA, F2,60=25.24, p=1.1×10-8). The responses were statistically indistinguishable from the hypothetical ideal correction (green versus black; two-way ANOVA, F1,60=0.41, p=0.52), and there was no significant interaction between the two factors (F2,60=0.20, p=0.98).

Figure 30:
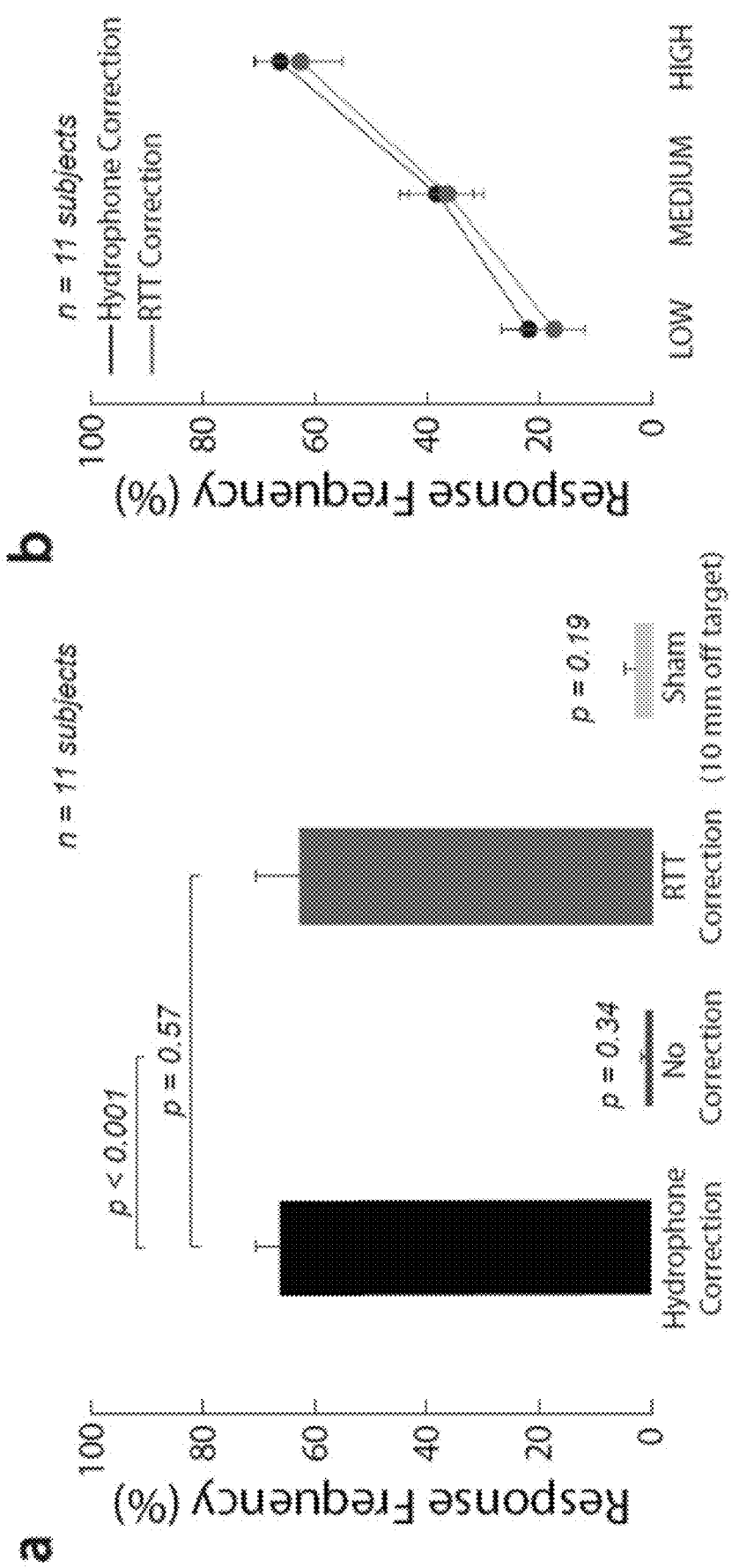
FIG. 30 illustrates that RTT enables effective ultrasonic stimulation through the skull. (a) RTT enables effective modulation of peripheral nerves through skull. The arrays targeted nerves in the thumb of 11 participants. The thumb was secured in the central target inside an ex-vivo skull. The arrays delivered into the target a 300 ms stimulus at a frequency of 650 kHz and pressure amplitude of 1.8 MPa. The data were collected with the ideal correction (black), without any correction (red), and after applying RTT (green). A sham condition delivered the stimulus 10 mm below the finger (yellow). The individual conditions were presented randomly every 8-12 s, for a total of 10 repetitions. Subjects reported any nociceptive response, which indicates stimulation of nerves and nerve endings. Response frequency represents the proportion of trials in which subjects reported a nociceptive response. (b) Dose-response relationship of the stimulation. There was a significant modulation by the ultrasound pressure but no significant difference in the responses following the ideal (black) and RTT (green) corrections (see text for details). The LOW, MEDIUM, and HIGH labels correspond to an intended peak pressure of 1.3, 1.55, and 1.8 MPa, as measured in free-field. The error bars represent the s.e.m.
Figure 31:
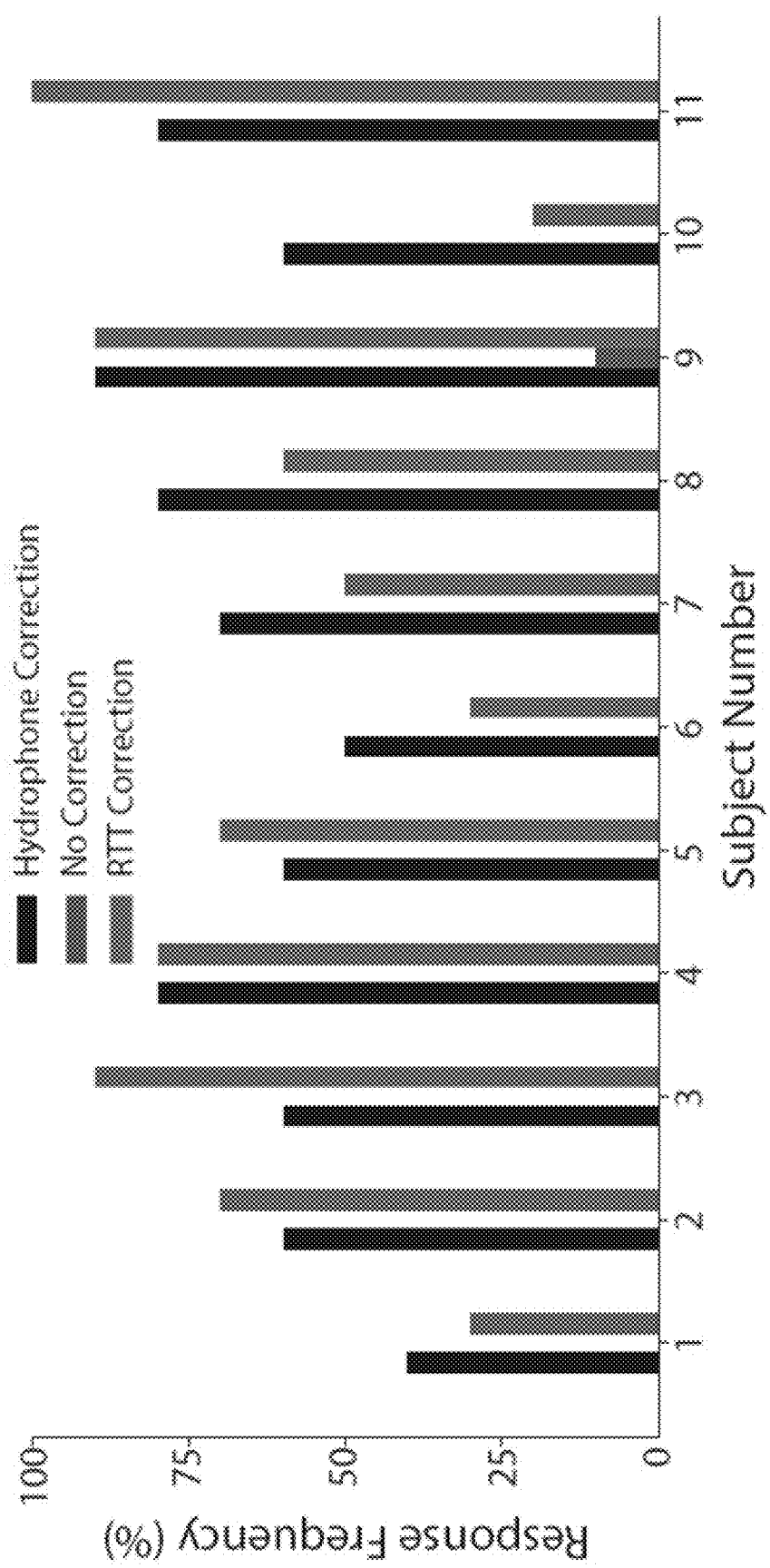
FIG. 31 illustrates the nerve stimulation in each subject. Mean response rates for the ideal (black) and RTT (green) correction for each individual subject. When RTT was not applied, there was no significant ultrasonic nerve stimulation (red; t11=1.00, p=0.34, one-sample t-test).

Therefore, the accurate compensation for the delivered intensities into brain targets (FIG. 25, FIG. 27) also translates into restored stimulation effectiveness with response levels not attainable without the RTT method described herein (FIG. 30).

The measurement and compensation for the human head described herein is critical for effective ultrasonic neuromodulation in the human brain. FIG. 33, left, shows that the compensation for the head enables strong ultrasonic neuromodulation. FIG. 33, right, shows that when this compensation is not applied, as has been the case with existing devices and approaches, there is no significant ultrasonic neuromodulation.

Example 4: Demonstrating Effective Application of Transcranial Ultrasound for Drug Release Using Head-Worn Device in Humans RTT was tested whether it could be used to release therapeutics (e.g., any hydrophobic drug, such as, propofol, mycophenolate motefil, and ketamine) at clinically-relevant and deterministic doses in specific locations inside the skull. In one example, ultrasound-sensitive nanoparticle carriers were devised and the neuromodulatory drug propofol was encapsulated in the nanoparticles at a concentration of 0.063 mg/ml. How the nanoparticles responded to ultrasound when RTT correction was applied and when it was not applied, was tested in a manner analogous to FIG. 30. It was discovered that RTT was critical to mediate effective release when ultrasound was applied through the skull (FIG. 32 (at a)). Without RTT (red), the amount of detected drug was no different (t14=0.30, p=0.77, two-sample two-tailed t-test) from the no stimulation case (purple). The application of RTT (green) nearly tripled the release effectiveness (factor of 2.9 increase), releasing 31.6% of the encapsulated propofol. This level was statistically equivalent (t18=0.08, p=0.94, paired two-tailed t-test) to the 31.8% release obtained with the hypothetical best-possible correction (black).

Figure 32:
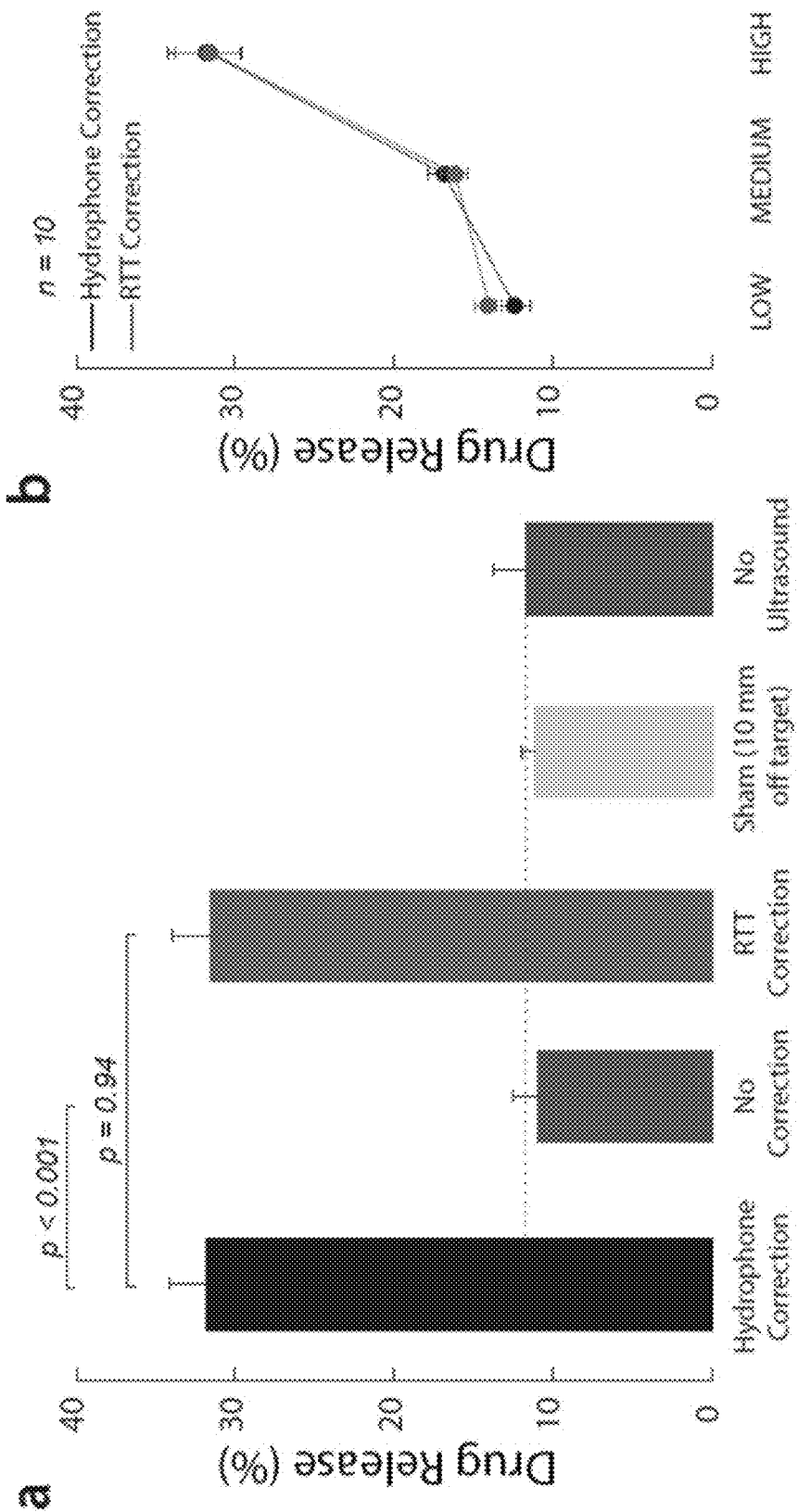
FIG. 32 illustrates that RTT enables effective and dose-dependent local drug release. (a) RTT enables effective drug release from nanoparticle carriers. Safe, biocompatible nanoparticle carriers encapsulated the neuromodulatory drug propofol. The nanoparticles release their drug load when impacted by low to medium intensity ultrasound. Vials with the nanoparticles were positioned within a central location of an ex-vivo skull, analogously to FIG. 30. Ultrasound, delivered through the skull, impacted the nanoparticles in 100 ms pulses delivered every 1 s for 60 s, at a frequency of 650 kHz and pressure amplitude of 1.8 MPa. The data were collected under the hypothetical ideal correction for the skull (black), without any correction (red), and after applying RTT (green). A sham condition delivered the stimulus 10 mm below the vial (yellow). A second sham condition placed the vial at target but delivered no ultrasound (purple). The dotted line represents the baseline when no ultrasound is applied. The baseline can be non-zero due to free (unencapsulated) drug or due to the nanoparticles being partially leaky. Analogously to FIG. 30, the individual conditions were randomly interleaved. The bars comprise n=10 distinct samples, with the exception of the No Ultrasound case, which used n=6. The error bars represent the s.e.m. (b) Dose-response relationship. The LOW, MEDIUM, and HIGH labels correspond to an intended peak pressure of 1.2, 1.5, and 1.8 MPa, as measured in free-field. All datapoints comprised n=10 distinct samples. The error bars represent the s.e.m.

The spatial specificity of the release was confirmed using a sham condition in which the ultrasound was focused 10 mm below each vial (FIG. 32 (at a)). In this case, the amount of detected drug was no different (t14=0.30, p=0.77) from the case in which no ultrasound was applied (purple).

The dose dependence of the release was also investigated. To do so, the delivered ultrasound intensity was varied across the same levels as in FIG. 30. An increase in stimulation effectiveness with increasing level of the ultrasound (FIG. 32 (at b)) was observed. The effect of the stimulation level was highly significant (two-way ANOVA, F2,54=84.53, p=2.3×10-17). The release levels were statistically indistinguishable from the hypothetical ideal correction (green versus black; two-way ANOVA, F1,54=0.02, p=0.89), and there was no significant interaction between the two factors (F2,54=0.35, p=0.7).

Therefore, the accurate compensation for the delivered intensities into brain targets (FIG. 25, FIG. 27) also translates into restored stimulation effectiveness with response levels not attainable without this method (FIG. 30). In other words, the intended ultrasonic intensity is sufficient to activate microbubbles and thus transiently disrupt the blood-brain barrier for localized delivery of drugs, genes, and stem cells across the blood-brain barrier.

Accordingly, in various different implementations, the disclosure provides, among other things, systems and methods for using ultrasound to apply focused ultrasound to a location in the brain and to use ultrasound itself to accurately compensate for the attenuation, phase shift, and/or changes in focal volume due to the presence of the head in the ultrasound path. Additional features and advantages of the invention are set forth in the following claims and the accompanying drawings.

What is claimed is:

1. A method for applying ultrasound to a target brain location, the method comprising:
   driving at least one transmitting ultrasound transducer to generate ultrasound waves to achieve an intended ultrasonic stimulation intensity at a target location in a free-field volume, the target location in the free-field volume corresponding to the target brain location;
   measuring the ultrasound waves using at least one receiving ultrasound transducer positioned at a fixed distance and orientation relative to the at least one transmitting ultrasound transducer on an opposite side of the free-field volume;
   positioning the at least one transmitting ultrasound transducer and the at least one receiving ultrasound transducer on opposite sides of a head, wherein a stationary distance and orientation of the at least one receiving ultrasound transducer relative to the at least one transmitting ultrasound transducer remains fixed;
   driving the at least one transmitting ultrasound transducer to generate the ultrasound waves into the head, wherein the ultrasound waves into the head are the same as the ultrasound waves generated to achieve the intended ultrasonic stimulation intensity at the target location in a free-field volume;
   measuring altered ultrasound waves exiting the head using the at least one receiving ultrasound transducer, wherein the altered ultrasound waves are attenuated and phase-shifted due at least in part to a presence of the head in an ultrasound path between the at least one transmitting ultrasound transducer and the at least one receiving ultrasound transducer;

determining one or more adjusted ultrasound waves based on differences between the measured ultrasound waves through the free-field volume and the measured altered ultrasound waves through the head, wherein the one or more adjusted ultrasound waves are adjusted to compensate for the attenuation and the phase-shift due to obstacles in the ultrasound path in order to cause an actual ultrasonic stimulation intensity at the target brain location to approach the intended ultrasonic stimulation intensity at the target brain location; and driving the at least one transmitting ultrasound transducer to generate the one or more adjusted ultrasound waves into the head at the intended ultrasonic stimulation intensity at the target brain location.

2. The method of claim 1, further comprising identifying a set of ultrasound transducers from an ultrasound transducer array, wherein the ultrasound transducer array includes a plurality of ultrasound transducers each positioned and oriented to project an ultrasound beam along a different ultrasound path, wherein the identified set of ultrasound transducers includes ultrasound transducers with respective ultrasound paths that intersect at the target brain location, and wherein driving the at least one transmitting ultrasound transducer to generate the ultrasound waves to achieve the intended ultrasonic stimulation intensity at the target brain location includes driving the ultrasound transducers of the identified set of ultrasound transducers to transmit ultrasound waves that in combination produce the intended ultrasonic stimulation intensity by superposition at the target brain location.

3. The method of claim 1, further comprising determining the attenuation and the phase-shift due to ultrasound waves passing through the head once based in part on a difference between the measured ultrasound waves through the free-field volume and the measured altered ultrasound waves through the head, wherein the difference is indicative of attenuation and phase shift caused by the ultrasound waves passing through each segment of the head.

4. The method of claim 1, further comprising determining a head attenuation of a first ultrasound wave transmitted by a first ultrasound transducer of the at least one transmitting ultrasound transducer, wherein the head attenuation is an attenuation due to ultrasound waves passing through the head once based at least in part on the measured altered ultrasound waves, wherein determining the one or more adjusted ultrasound waves includes scaling an amplitude of the first ultrasound wave by a factor of a multiplicative inverse of the determined head attenuation for the first ultrasound transducer.

5. The method of claim 4, wherein determining the head attenuation of the first ultrasound wave includes calculating the head attenuation of the first ultrasound wave according to:

$$\ln A_{ij} = k_{ij} \ln A_i + k_{ji} \ln A_j$$

where $A_{ij}$ is an attenuation of the first ultrasound wave due to the first ultrasound wave passing through both sides of the head, $A_{ij}$ is the head attenuation of the first ultrasound wave due to the first ultrasound wave passing into the head through a first side of the head, $A_{ij}$ is an attenuation of the first ultrasound wave due to the first ultrasound wave exiting the head through a second side of the head, and $k_{ij}$ is a multiplicative inverse of a cosine of an angle of an ultrasound beam emitted by the first ultrasound transducer.

6. The method of claim 1, wherein driving the at least one transmitting ultrasound transducer includes driving a plurality of ultrasound transducers, the method further comprising determining a plurality of head attenuation values, the plurality of head attenuation values including a determined head attenuation value for each ultrasound transducer of the plurality of ultrasound transducers, wherein each head attenuation value of the plurality of head attenuation values is indicative of an attenuation due to ultrasound waves transmitted by a respective ultrasound transducer of the plurality of ultrasound transducers passing through the head once, wherein determining the one or more adjusted ultrasound waves includes scaling an amplitude of an ultrasound wave of the ultrasound waves transmitted by each ultrasound transducer of the plurality of ultrasound transducers by a factor of a multiplicative inverse of the determined skull head attenuation value corresponding to the ultrasound transducer.

7. The method of claim 1, wherein the altered ultrasound waves exiting the head include amplitudes and phases that are scaled and delayed such that the altered ultrasound waves received during the through-head measurements approach the ultrasound waves received during the free-field measurements.

8. An ultrasound delivery system comprising:

a device configured to be removably coupled to a head, the device including at least one array of ultrasound transducers, wherein the at least one array of ultrasound transducers includes ultrasound transducers configured to be positioned on opposite sides of a volume; and a controller configured to determine a first set of ultrasound waves to be transmitted by a first set of ultrasound transducers of the at least one array of ultrasound transducers in order to achieve an intended ultrasonic stimulation intensity at a target location within the volume, the target location corresponding to a target brain location, drive the first set of ultrasound transducers according to the determined first set of ultrasound waves, capture a free field measurement of ultrasound waves using a second set of ultrasound transducers on an opposite side of the volume from the first set of ultrasound transducers while the device is not applied to the head, capture a through-transmit measurement of ultrasound waves using the second set of ultrasound transducers while the device is applied to the head, compare the free field measurement and the through-transmit measurement to determine attenuation and phase shift in the ultrasound waves used to capture the through-transmit measurement due at least in part to a presence of the head in an ultrasound path between the first set of ultrasound transducers and the second set of ultrasound transducers, determine an adjusted set of ultrasound waves to be transmitted by the first set of ultrasound transducers, wherein the adjusted set of ultrasound waves compensates for the determined attenuation and the determined phase shift to achieve the intended ultrasonic stimulation intensity at the target brain location while the device is applied to the head; and drive the first set of ultrasound transducers according to the determined adjusted set of ultrasound waves while the device is applied to the head.

9. The ultrasound delivery system of claim 8, wherein the at least one array of ultrasound transducers includes a plurality of ultrasound transducers each positioned and oriented to project an ultrasound beam along a different ultrasound path,
wherein the controller is further configured to identify the first set of ultrasound transducers by identifying ultrasound transducers with ultrasound paths that will intersect at the target location, and
wherein the controller is configured to determine the first set of ultrasound waves to be transmitted by the first set of ultrasound transducers in order to achieve the intended ultrasonic stimulation intensity at the target location by determining a combination of ultrasound waves that will combine to produce the intended ultrasonic stimulation intensity by superposition when the ultrasound paths intersect at the target location.

10. The ultrasound delivery system of claim 8, wherein the controller is further configured to determine the attenuation and the phase-shift due to ultrasound waves passing through the head once based in part on a difference between the measured ultrasound waves through the free-field volume and the measured through-transmit ultrasound waves through the head, wherein the difference is indicative of attenuation and phase shift caused by the ultrasound waves passing through each segment of the head.

11. The ultrasound delivery system of claim 8, wherein the controller is further configured to determine a plurality of head attenuation values, the plurality of head attenuation values including a determined head attenuation value for each ultrasound transducer of the first set of ultrasound transducers, wherein each head attenuation value of the plurality of head attenuation values is indicative of an attenuation due to the ultrasound wave transmitted by a respective ultrasound transducer of the first set of ultrasound transducers passing through the head once, and
wherein the controller is configured to determine the adjusted set of ultrasound waves by scaling an amplitude of the ultrasound wave transmitted by each ultrasound transducer of the first set of ultrasound transducers by a factor of a multiplicative inverse of the determined head attenuation value corresponding to the respective ultrasound transducer.

12. The ultrasound delivery system of claim 11, wherein determining the plurality of head attenuation values includes calculating the head attenuation value for each ultrasound transducer of the first set of ultrasound transducers according to:

$$\ln A_{ij} = k_{ij} \ln A_i + k_{ji} \ln A_{ij}$$

where $A_{ij}$ is an attenuation of the ultrasound wave due to the ultrasound wave passing through both sides of the head, $A_{ij}$ is the skull attenuation for the ultrasound transducer due to the first ultrasound wave passing into the head through a first side of the head, $A_{ij}$ is an attenuation of the ultrasound wave due to the ultrasound wave exiting the head through a second side of the head, and $k_{ij}$ is a multiplicative inverse of a cosine of an angle of an ultrasound beam emitted by the first ultrasound transducer of the first set of ultrasound transducers.

13. The ultrasound delivery system of claim 8, wherein the at least one array of ultrasound transducers includes a first ultrasound transducer array and a second ultrasound transducer array, wherein the device includes a frame coupling the first ultrasound transducer array and the second ultrasound transducer array to the device on opposite sides of the volume.

14. The ultrasound delivery system of claim 8, wherein the head-worn device includes a crown-shaped body with a first opening sized to receive the head and a second opening opposite the first opening through which a top of the head remains exposed when the device is applied to the head.

15. The ultrasound delivery system of claim 8, wherein the device includes an adjustable support mechanism configured to position and support the device on the head when worn.

* * * * *